United States Patent
Woodruff et al.

(10) Patent No.: US 10,933,049 B2
(45) Date of Patent: Mar. 2, 2021

(54) MOBILIZING AGENTS AND USES THEREFOR

(71) Applicant: The University of Queensland, St Lucia (AU)

(72) Inventors: Trent Woodruff, Carindale (AU); Barbara Rolfe, Holland Park West (AU)

(73) Assignee: The University of Queensland, Brisbane (AU)

( * ) Notice: Subject to any disclaimer, the term of this patent is extended or adjusted under 35 U.S.C. 154(b) by 357 days.

(21) Appl. No.: 15/579,339

(22) PCT Filed: Jun. 1, 2016

(86) PCT No.: PCT/AU2016/050435
§ 371 (c)(1),
(2) Date: Dec. 4, 2017

(87) PCT Pub. No.: WO2016/191811
PCT Pub. Date: Dec. 8, 2016

(65) Prior Publication Data
US 2018/0185328 A1 Jul. 5, 2018

(30) Foreign Application Priority Data
Jun. 3, 2015 (AU) .............................. 2015902140

(51) Int. Cl.
| | |
|---|---|
| *A61K 31/395* | (2006.01) |
| *A61K 45/06* | (2006.01) |
| *C07K 14/72* | (2006.01) |
| *C12N 5/09* | (2010.01) |
| *A61P 35/00* | (2006.01) |
| *A61K 35/28* | (2015.01) |
| *A61K 38/19* | (2006.01) |
| *A61K 35/12* | (2015.01) |

(52) U.S. Cl.
CPC ............ *A61K 31/395* (2013.01); *A61K 35/28* (2013.01); *A61K 38/193* (2013.01); *A61K 45/06* (2013.01); *A61P 35/00* (2018.01); *C07K 14/723* (2013.01); *C12N 5/0693* (2013.01); *A61K 2035/124* (2013.01)

(58) Field of Classification Search
None
See application file for complete search history.

(56) References Cited

U.S. PATENT DOCUMENTS

| | | |
|---|---|---|
| 2006/0035829 A1 | 2/2006 | Bridger et al. |
| 2007/0043012 A1 | 2/2007 | Bridger |
| 2009/0035319 A1 | 2/2009 | Rosen |
| 2012/0315279 A1 | 12/2012 | Medof et al. |

FOREIGN PATENT DOCUMENTS

| | | |
|---|---|---|
| WO | WO 2007/034277 A1 | 3/2007 |
| WO | WO 2008/019371 A1 | 2/2008 |
| WO | 2009/108931 | 9/2009 |
| WO | WO 2010/088398 A1 | 8/2010 |
| WO | WO 2010/092571 A2 | 8/2010 |
| WO | WO 2014/134539 A1 | 9/2014 |
| WO | WO 2015/019284 A2 | 2/2015 |

OTHER PUBLICATIONS

Ratajczak, J. et al., Blood 2004, vol. 103, pp. 2071-2078.*
International Search Report for PCT/AU2016/050435, four pages, dated Aug. 9, 2016.
Written Opinion of the ISA for PCT/AU2016/050435, four pages, dated Aug. 9, 2016.
Ames et al. "Identification of a selective nonpeptide antagonist of the anaphylatoxin C3a receptor that demonstrates anti-inflammatory activity in animal models" *Journal of Immunology*, vol. 166, No. 10, pp. 6341-6348 (May 2001).
Honczarenko et al. "Complement C3a enhances CXCL12 (SDF-1)-mediated chemotaxis of bone marrow hematopoietic cells independently of C3a receptor" *Journal of Immunology*, vol. 175, No. 6, pp. 3698-3706 (Sep. 2005).
Ratajczak et al. "Mobilization studies in mice deficient in either C3 or C3a receptor (C3aR) reveal a novel role for complement in retention of hematopoietic stem/progenitor cells in bone marrow" *Blood*, vol. 103, No. 6, pp. 2071-2078 (Mar. 2004).
L. B. To et al. "How I treat patients who mobilize hematopoietic stem cells poorly" vol. 118, No. 17, Aug. 10, 2011.
Int'l Preliminary Report on Patentability for PCT/AU2016/050435, five pages, dated Dec. 5, 2017.

* cited by examiner

*Primary Examiner* — Heidi Reese
(74) *Attorney, Agent, or Firm* — Nixon & Vanderhye, PC

(57) ABSTRACT

The present invention discloses the use of a complement 3a receptor (C3aR) antagonist and a mobilizer of hematopoietic stem cells and/or progenitor cells in methods and compositions for stimulating or enhancing the development, mobilization, proliferation and/or differentiation of a neutrophil-containing leukocyte population that inhibits growth and/or spread of a tumor and for treating or preventing a hyperproliferative cell disorder.

8 Claims, 19 Drawing Sheets
Specification includes a Sequence Listing.

MOBILIZING AGENTS AND USES THEREFOR

This application is the U.S. national stage of International Application No. PCT/AU2016/050435, filed 1 Jun. 2016, which designated the U.S. and claims priority benefit of Australian Provisional Application No. (AU) 2015902140, filed 3 Jun. 2015; the entire contents of each of which are incorporated herein by reference in their entirety.

FIELD OF THE INVENTION

This invention relates generally to the use of a complement 3a receptor (C3aR) antagonist and a mobilizer of hematopoietic stem cells and/or progenitor cells in methods and compositions for stimulating or enhancing the development, mobilization, proliferation and/or differentiation of a neutrophil-containing leukocyte population that inhibits growth and/or spread of a tumor and for treating or preventing a hyperproliferative cell disorder.

BACKGROUND OF THE INVENTION

Melanoma is the most aggressive form of skin cancer, and the fourth most common cancer reported in Australia, with over 12,500 new cases diagnosed each year. It is the most common cancer in young Australians (15-39 years old), and in this age group is responsible for more deaths than any other cancer. Despite recent advances in treatment of advanced melanoma (Finn, 2012), metastatic melanoma remains an incurable disease with a 5-year survival rate below 10%, and median survival of only 4-6 months (Boyle, 2011).

An essential part of the innate immune system, the complement system is comprised of plasma and membrane-bound proteins whose overall function is to regulate inflammation, facilitate immune defense mechanisms and maintain tissue homeostasis (Ricklin et al., 2010). Complement activation leads to the production of the complement peptides C3a and C5a and the membrane attack complex (C5b-9; MAC), through which the complement system exerts many of its effects (Klos et al., 2013). The detection of complement activation products in tumor tissue (Ajona et al., 2013; Niculescu et al., 1992) is evidence that the complement system is activated in response to tumor cells. Up-regulated levels of serum C3a have been reported in many cancers including breast, colorectal and esophageal cancer (Maher et al., 2011; Medina-Echeverz et al., 2014), and gene expression data identifies the up-regulation of C3a receptor (C3aR) by some tumors, including melanoma (Xu et al., 2008). Despite the evidence for C3a and C3aR expression by tumor tissue, the majority of studies to date have focused on the role of C5a (Corrales et al., 2012; Gunn et al., 2012; Kim et al., 2005; Markiewski et al., 2008; Nunez-Cruz et al., 2012).

C3aR is expressed by cells of myeloid origin (including neutrophils, mast cells, monocytes, macrophages and dendritic cells) as well as non-immune cells in lung, liver, muscle and other tissues. Activation of C3aR can induce both pro- and anti-inflammatory effects, depending on the cell type and disease context (Coulthard and Woodruff, 2015).

SUMMARY OF THE INVENTION

The present invention is based in part on the determination that C3aR deficiency or antagonism leads to increased tumor infiltration by a neutrophil-containing leukocyte population that inhibits growth and/or spread (i.e., metastasis) of the tumor. The present inventors have also found that the size and effect of this anti-tumor leukocyte population can be significantly enhanced by co-administration of a stem cell-mobilizing agent (also referred to herein as "mobilizer" or "mobilizer of hematopoietic stem cells and/or progenitor cells") such as granulocyte-colony stimulating factor (G-CSF). Based on this determination, the present inventors propose that C3aR antagonists and mobilizers of hematopoietic stem cells and/or progenitor cells are useful in compositions and methods for treating tumors, including non-metastatic and metastatic tumors, as described hereafter.

Accordingly, in one aspect, the present invention provides compositions that comprise, consist or consist essentially of a C3aR antagonist and a mobilizer of hematopoietic stem cells and/or progenitor cells. The C3aR antagonist is selected, without limitation, from agents that inhibit C3aR signaling including agents that inhibit the interaction between C3a and C3aR, illustrative examples of which include agents that bind to C3aR and block interaction of C3aR with C3a, agents that bind to C3a and block its interaction with C3aR, agents that inhibit expression of C3aR and combinations thereof. In some embodiments, the C3aR antagonist is a selective C3aR antagonist. In other embodiments, the C3aR antagonist is a non-selective C3aR antagonist. In some embodiments, the mobilizer is selected from a growth factor, a cytokine, a chemokine or a polysaccharide. Suitably, the mobilizer is characterized by its ability to decrease or block the expression, synthesis or function of CXCL12 or is characterized by its ability to block or antagonize CXCR4. In specific embodiments, the mobilizer is selected from a colony stimulating factor such as G-CSF, a CXCR4 antagonist such as Plerixafor, or a combination thereof. In some embodiments, the compositions further comprise a pharmaceutically acceptable carrier. In some embodiments, the compositions further comprise at least one ancillary agent selected from a chemotherapeutic agent (e.g., a cytotoxic agent), a radiosensitizing agent, an E-selectin antagonist, an anemia medicament, a thrombocytopenia medicament, a neutropenia medicament, an agranulocytosis medicament and an anti-infective agent.

The compositions of the present invention are useful for enhancing an immune response to a tumor, for stimulating or enhancing the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or spread of a tumor and for treating or preventing a hyperproliferative cell disorder. Accordingly, in a related aspect, the present invention provides a use of a C3aR antagonist and a mobilizer of hematopoietic stem cells and/or progenitor cells for enhancing an immune response to a tumor. Suitably, the immune response comprises infiltration of the tumor by a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of the tumor. In yet another related aspect, the present invention provides a use of a C3aR antagonist and a mobilizer of hematopoietic stem cells and/or progenitor cells for stimulating or enhancing the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or spread of a tumor.

In still another related aspect, the present invention provides a use of a C3aR antagonist and a mobilizer of hematopoietic stem cells and/or progenitor cells for treating a hyperproliferative cell disorder (e.g., a cancer, including a non-metastatic cancer or a metastatic cancer). In some embodiments, the C3aR antagonist and the mobilizer are prepared or manufactured as medicaments for those applications.

Another aspect of the present invention provides methods for enhancing an immune response (e.g., an enhanced neutrophil-containing leukocyte response, and suitably a T lymphocyte response such as a $CD4^+$ T lymphocyte response and/or a $CD8^+$ T lymphocyte response) to a tumor in a subject. These methods generally comprise, consist or consist essentially of concurrently administering to the subject a C3aR antagonist and a mobilizer of hematopoietic stem cells and/or progenitor cells in effective amounts to enhance the immune response to the tumor. The tumor is generally a cell surface positive tumor and includes precancerous, non-metastatic, metastatic, and cancerous tumors (e.g., early stage cancer). In specific embodiments, the C3aR antagonist is administered locally to the tumor. In illustrative examples of this type, the mobilizer is administered systemically to the subject. Representative cancers are selected from carcinoma, lymphoma, blastoma, sarcoma, neuroendocrine tumors, mesothelioma, schwannoma, meningioma, adenocarcinoma, melanoma, leukemia, and lymphoid malignancies. In some embodiments, the cancer is selected from lung cancer, hepatocellular cancer, gastric or stomach cancer, pancreatic cancer, glioblastoma, cervical cancer, ovarian cancer, liver cancer, bladder cancer, hepatoma, breast cancer, colon cancer, rectal cancer, colorectal cancer, endometrial and uterine carcinoma, salivary gland carcinoma, kidney cancer, prostate cancer, vulval cancer, thyroid cancer, hepatic carcinoma, anal carcinoma, penile carcinoma, testicular cancer, esophageal cancer, tumors of the biliary tract, and head and neck cancer. In specific embodiments, the tumor is of an epithelial origin, non-limiting examples of which include cancer of the lung, colon, prostate, ovary, breast, and skin (e.g., melanoma and squamous cell carcinoma (SCC)). Suitably, the immune response comprises infiltration of the tumor by a neutrophil-containing leukocyte population (e.g., one that comprises neutrophils and suitably further comprises T lymphocytes such as $CD4^+$ T lymphocytes) that inhibits growth and/or metastasis of the tumor.

In a related aspect, the present invention provides methods for stimulating or enhancing the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of a tumor in a subject. These methods generally comprise, consist or consist essentially of concurrently administering to the subject a C3aR antagonist and a mobilizer of hematopoietic stem cells and/or progenitor cells in effective amounts to stimulate or enhance the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of the tumor.

In another related aspect, the present invention provides methods for reducing the incidence of a hyperproliferative cell disorder (e.g., a cancer, including a non-metastatic cancer or a metastatic cancer) in a subject, wherein the methods generally comprise, consist or consist essentially of concurrently administering to the subject a C3aR antagonist and a mobilizer of hematopoietic stem cells and/or progenitor cells in effective amounts to reduce the incidence of the hyperproliferative cell disorder.

In yet another related aspect, the present invention provides methods for reducing recurrence of a hyperproliferative cell disorder (e.g., a cancer, including a non-metastatic cancer or a metastatic cancer) in a subject, wherein the methods generally comprise, consist or consist essentially of concurrently administering to the subject a C3aR antagonist and a mobilizer of hematopoietic stem cells and/or progenitor cells in effective amounts to reduce recurrence of the hyperproliferative cell disorder.

In still another related aspect, the present invention provides methods for treating or preventing a hyperproliferative cell disorder (e.g., a cancer, including a non-metastatic cancer or a metastatic cancer) in a subject, wherein the methods generally comprise, consist or consist essentially of concurrently administering to the subject a C3aR antagonist and a mobilizer of hematopoietic stem cells and/or progenitor cells in effective amounts to treat or prevent the hyperproliferative cell disorder.

Suitably, the C3aR antagonist and the mobilizer are administered in synergistically effective amounts.

Yet another aspect of the present invention provides methods for treating or preventing a hyperproliferative cell disorder (e.g., a cancer, including a non-metastatic cancer or a metastatic cancer) in a subject. These methods generally comprise, consist or consist essentially of concurrently administering to the subject (1) a C3aR antagonist and (2) a mobilizer of hematopoietic stem cells and/or progenitor cells in effective amounts to stimulate or enhance the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of a tumor associated with the cancer, and (3) an ancillary therapy or agent that inhibits the proliferation, survival or viability of the tumor, to thereby treat or prevent the hyperproliferative cell disorder. In some embodiments, the ancillary therapy or agent is selected from radiotherapy, surgery, chemotherapy, hormone ablation therapy, pro-apoptosis therapy and immunotherapy. In illustrative examples of this type, the ancillary therapy or agent targets rapidly dividing cells or disrupts the cell cycle or cell division. In some embodiments, the methods further comprise administering an E-selectin antagonist for delaying hematopoietic stem cell turnover and/or for protecting hematopoietic stem cells and/or progenitor cells from medical treatments that target rapidly dividing cells and/or for enhancing mobilization of hematopoietic stem cells and/or progenitor cells by the mobilizer. In illustrative examples of this type, the E-selectin antagonist is administered to the subject prior to the administration of the ancillary therapy or agent. In other examples, the E-selectin antagonist is concurrently administered to the subject with the ancillary therapy or agent. In some embodiments, the methods further comprise administering (e.g., concurrently administering) a medicament that treats, prevents or otherwise ameliorates an immunocompromised condition resulting for example from the ancillary therapy or agent illustrative examples of which include an anemia medicament, a thrombocytopenia medicament, a neutropenia medicament, an agranulocytosis medicament and an anti-infective agent.

Suitably, the C3aR antagonist, the mobilizer and the ancillary therapy or agent are administered in synergistically effective amounts.

Still another aspect of the present invention provides methods for treating or preventing a hyperproliferative cell disorder (e.g., a cancer, including a non-metastatic cancer or a metastatic cancer) in a subject. These methods generally comprise, consist or consist essentially of concurrently administering to the subject (1) a C3aR antagonist and (2) a mobilizer of hematopoietic stem cells and/or progenitor cells in effective amounts to stimulate or enhance the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of a tumor associated with the cancer, and (3) an E-selectin antagonist for delaying hematopoietic stem cell turnover and/or protecting hematopoietic stem cells and/or progenitor cells from medical treatments that target rapidly dividing cells and/or for enhancing mobilization of hematopoietic stem cells and/or progenitor cells by the mobilizer. In some embodiments, the methods further comprise administering an ancillary therapy or agent that inhibits the proliferation, survival or viability of the tumor, to thereby treat or prevent the hyperproliferative cell disorder. In illustrative examples of this type, the ancillary therapy or agent is administered to the subject after the administration of the E-selectin antagonist. In other examples, the ancillary therapy or agent is concurrently administered to the subject with the E-selectin antagonist. In some embodiments, the ancillary therapy or agent is selected from radiotherapy, surgery, chemotherapy, hormone ablation therapy, pro-apoptosis therapy and immunotherapy. In illustrative examples of this type, the ancillary therapy or agent targets rapidly dividing cells or disrupts the cell cycle or cell division. In some embodiments, the methods further comprise administering a medicament that treats, prevents or otherwise ameliorates an immunocompromised condition resulting for example from the ancillary therapy or agent illustrative examples of which include an anemia medicament, a thrombocytopenia medicament, a neutropenia medicament, an agranulocytosis medicament and an anti-infective agent.

Suitably, the C3aR antagonist, the mobilizer and the E-selectin antagonist are administered in synergistically effective amounts.

Typically, at least one (e.g., 1, 2 or all) of the C3aR antagonist, the mobilizer, the ancillary therapy or agent, and the E-selectin antagonist are administered on a routine schedule, for example, every day, at least twice a week, at least three times a week, at least four times a week, at least five times a week, at least six times a week, every week, every other week, every third week, every fourth week, every month, every two months, every three months, every four months, and every six months.

In some embodiments, the ancillary therapy or agent is likely to expose the subject to a higher risk of infection with a pathogenic organism. Accordingly, in these embodiments, the methods may further comprise administering simultaneously, sequentially or separately with the C3aR antagonist and the mobilizer and optionally the ancillary therapy/agent at least one anti-infective agent that is effective against an infection that develops or that has an increased risk of developing by administration of the cancer therapy or agent, wherein the anti-infective agent is selected from antimicrobials, antibiotics, antivirals, antifungals, anthelmintics, antiprotozoals and nematocides.

In some embodiments of the methods described above in which the subject is exposed to an ancillary therapy or agent that targets rapidly dividing cells or disrupts the cell cycle or cell division, the hematopoietic stem cells and/or progenitor cells, which are suitably mobilized through use of the mobilizer, are isolated from a subject or from another subject (e.g., a donor subject) prior to exposing the subject with the ancillary therapy or agent. In some embodiments, the subject or the donor subject is concurrently administered the C3aR antagonist with the mobilizer. The isolated hematopoietic stem cells and/or progenitor cells can be infused or transplanted into the subject after treatment of the subject with the ancillary therapy or agent. In some embodiments, the isolated hematopoietic stem cells and/or progenitor cells are exposed to the C3aR antagonist prior to the infusion or transplantation, in order to stimulate or enhance the development, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of a tumor. Alternatively, the isolated hematopoietic stem cells and/or progenitor cells are concurrently administered to the subject with a C3aR antagonist.

BRIEF DESCRIPTION OF THE DRAWINGS

(FIG. 1A and FIG. 1B) Tumor area and excised weight 14 days post-tumor induction in C57BL/63 (wild-type; WT •) and C3aR deficient ($C3aR^{-/-}$ □) mice (n=32/group). Representative of 4 independent experiments. (FIG. 1C) Photographs show representative tumors from mice WT and $C3aR^{-/-}$ mice. (FIG. 1D) Kaplan-Meier curve shows increased survival of $C3aR^{-/-}$ compared with wild-type mice; the terminal event is euthanasia once tumors reach maximal size (n=11/group). (FIG. 1E and FIG. 1F) Tumor areas and weight of excised tumors from WT or $C3aR^{-/-}$ mice treated from day 7 with either saline (vehicle; WT •, $C3aR^{-/-}$ □) or C5aR antagonist, PMX53 (1 mg/kg/day; WT ▲, $C3aR^{-/-}$ ∆) (n=7/group). Data expressed as mean±SD; $p<0.01$, *$p<0.0005$, ****$p<0.0001$, Permutation test (FIG. 1A and FIG. 1E), log-rank (Mantel-Cox) test (FIG. 1D), Mann-Whitney test (FIG. 1B) and Kruskal Wallis test followed by Dunn's multiple comparisons test (FIG. 1F).

(FIG. 2A and FIG. 2B) Tumor areas and weight of excised tumors from C57Bl/6J mice treated from day 7 with either saline (vehicle, •) or selective C3aR antagonist (C3aRA; SB290157, 1 mg/kg/day, ■) (n=28/group). Representative of 3 independent experiments. (FIG. 2C) Photographs show representative tumors from mice treated with vehicle alone or C3aR antagonist. (FIG. 2D) Kaplan-Meier curve shows increased survival of mice treated with C3aRA compared with vehicle alone; the terminal event is euthanasia once tumors reach maximal size; (n=7/group). Data expressed as mean±SD; $p<0.01$, **$p<0.0001$, Permutation test (FIG. 2A), Mann-Whitney test (FIG. 2B) and log-rank (Mantel-Cox) test (FIG. 2D).

(FIG. 3A) Photomicrographs show immunostaining of cultured B16 melanoma cells and J774 macrophages with Alexa-647 conjugated anti-mouse C3aR (orange); nuclei are counterstained with Hoechst 33342

(blue); scale bar=25 μm. (FIG. 3B) Representative FACS profiles for cultured B16 melanoma (blue line) and J774 (orange line) cells stained with anti-C3aR or isotype control (red line). (FIG. 3C) Representative immunoblots show levels of phosphorylated ERK1/2 or phosphorylated AKT following stimulation of B16 cells with recombinant human C3a (hC3a; $10^{-8}$ mol/L) for 0-60 min. Immunoblotting for total ERK or AKT was used as loading control. Densitometry of bands shows ERK or AKT activation relative to the untreated control (0 min). (FIG. 3D) Histogram shows B16 cell migration following treatment with DMEM alone or containing C3a agonist (C3a-A; WWGKKYRASKLGLAR [SEQ ID NO: 5], $10^{-6}$ mol/L) or 5% FCS for 24 hours. One-way ANOVA (FIG. 3D). Data expressed as mean±SD, *$p<0.05$, ****$p<0.0001$.

(FIG. 4A and FIG. 4B) Immunostaining of B16 tumors from WT and C3aR$^{-/-}$ mice shows CD45 cells (green) encapsulating the tumor tissue (dotted line indicates leukocyte 'capsule'). (FIG. 4C and FIG. 4D) Immunostaining of B16 tumors from WT and C3aR$^{-/-}$ mice shows CD45$^+$ cells within tumor tissue. (FIG. 4E and FIG. 4F) Many tumor infiltrating cells are neutrophils (Ly6G$^+$; green), but (FIG. 4G and FIG. 4H) macrophages (F4/80+; red), and (FIG. 4I and FIG. 4J) T lymphocytes (CD3+; green), are also present. (FIG. 4K) Tissue stained with an isotype control antibody. Nuclei are stained with Hoechst 33342 (blue).

(FIG. 5A to FIG. 5C) Percentages of leukocyte sub-populations in tumor tissue, draining lymph nodes (DLN) and spleen from WT and C3aR$^{-/-}$ mice: total leukocytes (CD45$^+$), monocytes (CD11b+Ly6C+), neutrophils (CD11b$^+$Ly6G$^+$), myeloid-derived suppressor cells (MDSCs) (CD11b$^+$GR1$^+$), macrophages (F4/80$^+$), total (CD3$^+$), CD4$^+$ and CD8$^+$ T lymphocytes; results of 2 independent experiments, n=16/group. CD4$^+$ T lymphocyte subsets, Treg (CD4$^+$CD25$^+$FoxP3$^+$), Th1 (CD4$^+$IFNγ$^+$), Th2 (CD4$^+$IL4$^+$) and Th17 (CD4$^+$IL17$^+$); results of one experiment, n=7-8/group. Data expressed as % positive cells (mean±SD); *$p<0.05$, $p<0.01$, *$p<0.001$, ****$p<0.0001$, Mann Whitney test. See also FIGS. 6A-6B.

(FIG. 6A and FIG. 6B) Percentages of leukocyte sub-populations in bone marrow and blood from WT and C3aR$^{-/-}$ mice: total leukocytes (CD45$^+$), monocytes (CD11b+Ly6C+), neutrophils (CD11b$^+$Ly6G$^+$), MDSCs (CD11b$^+$GR1$^+$), macrophages (F4/80$^+$), total (CD3$^+$), CD4$^+$ and CD8$^+$ T lymphocytes; results of 2 independent experiments, n=16/group. CD4$^+$ T lymphocyte subsets, Treg (CD4$^+$CD25$^+$FoxP3$^+$), Th1 (CD4$^+$IFNγ$^+$), Th2 (CD4$^+$IL4$^+$) and Th17 (CD4$^+$IL17$^+$); results of one experiment, n=7-8/group. Data expressed as % positive cells (mean±SD); *$p<0.05$, $p<0.01$, *$p<0.001$, ****$p<0.0001$, Mann Whitney test.

(FIG. 7A, FIG. 7B, and FIG. 7C) Percentages of leukocyte sub-populations in tumor tissue, draining lymph nodes (DLN) and spleen from WT mice treated with SB209157 (1 mg/kg/day) or vehicle commencing once tumors became palpable: total leukocytes (CD45$^+$), monocytes (CD11b$^+$Ly6C$^+$), neutrophils (CD11b$^+$Ly6G$^+$), MDSCs (CD11b$^+$GR1$^+$), macrophages (F4/80$^+$), total (CD3$^+$), CD4$^+$ and CD8$^+$ T lymphocytes; results of 2 independent experiments, n=16-17/group. CD4$^+$ T lymphocyte subsets, Treg (CD4$^+$CD25$^+$FoxP3$^+$), Th1 (CD4$^+$IFNγ$^+$), Th2 (CD4$^+$IL4$^+$) and Th17 CD4$^+$ (CD4$^+$IL17$^+$); results of 1 experiment, n=9-10/group. Data expressed as % positive cells (mean±SD); *$p<0.05$, $p<0.01$, *$p<0.001$, ****$p<0.0001$, Mann-Whitney test.

(FIG. 8A and FIG. 8B) Percentages of leukocyte sub-populations in bone marrow and blood from WT mice treated with SB209157 (1 mg/kg/day) or vehicle commencing once tumors became palpable: total leukocytes (CD45$^+$), monocytes (CD11b$^+$Ly6C$^+$), neutrophils (CD11b$^+$Ly6G$^+$), MDSCs (CD11b$^+$GR1$^+$), macrophages (F4/80$^+$), total (CD3$^+$), CD4$^+$ and CD8$^+$ T lymphocytes; CD4$^+$ T lymphocyte subsets, Treg (CD4$^+$CD25$^+$FoxP3$^+$), Th1 (CD4$^+$IFNγ$^+$), Th2 (CD4$^+$IL4$^+$) and Th17 CD4$^+$ (CD4$^+$IL17$^+$); results of 1 experiment, n=9-10/group. Data expressed as % positive cells (mean±SD); *$p<0.05$, ****$p<0.0001$, Mann-Whitney test.

(FIG. 9A) FACS results verifying neutrophil depletion in blood. (FIG. 9B and FIG. 9C) Tumor area and excised tumor weights for WT and C3aR$^{-/-}$ mice treated with neutrophil depleting anti-Ly6G (1A8) or isotype control (2A3). (FIG. 9D) Tumor infiltrating leukocyte populations for WT and C3aR$^{-/-}$ mice treated with neutrophil depleting anti-Ly6G (1A8) or isotype control (2A3). Data expressed as % positive cells (mean±SD); *$p<0.05$, $p<0.01$, *$p<0.001$, ****$p<0.0001$, Kruskal Wallis test followed by Dunn's multiple comparisons test (FIG. 9A, FIG. 9C, and FIG. 9D) or Permutation Test (FIG. 9B).

(FIG. 11A) tumor area and (FIG. 11B) excised tumor weight for SM1WT1 melanoma grown in WT (•) and C3aR$^{-/-}$ (☐) mice (n=7-10/group). (FIG. 11C) tumor area and (FIG. 11D) excised tumor weight for MC38 colon carcinoma grown in WT and C3aR$^{-/-}$ mice (n=6/group). (FIG. 11E) tumor area and (FIG. 11F) excised tumor weight for 4T1 mammary carcinoma grown in female BALB/c mice and treated by daily i.p. injection of either saline (veh, •) or selective C3aR antagonist (C3aRA; SB290157, 1 mg/kg/day) from day 0 (n=6/group). Data expressed as mean±SD,  $p<0.01$ *$p<0.005$, ****$p<0.0001$, Permutation test (FIG. 11A, FIG. 11C, and FIG. 11E) and Mann-Whitney test (FIG. 11B, FIG. 11D, and FIG. 11F).

DETAILED DESCRIPTION OF THE INVENTION

I. Definitions

Figure 1:
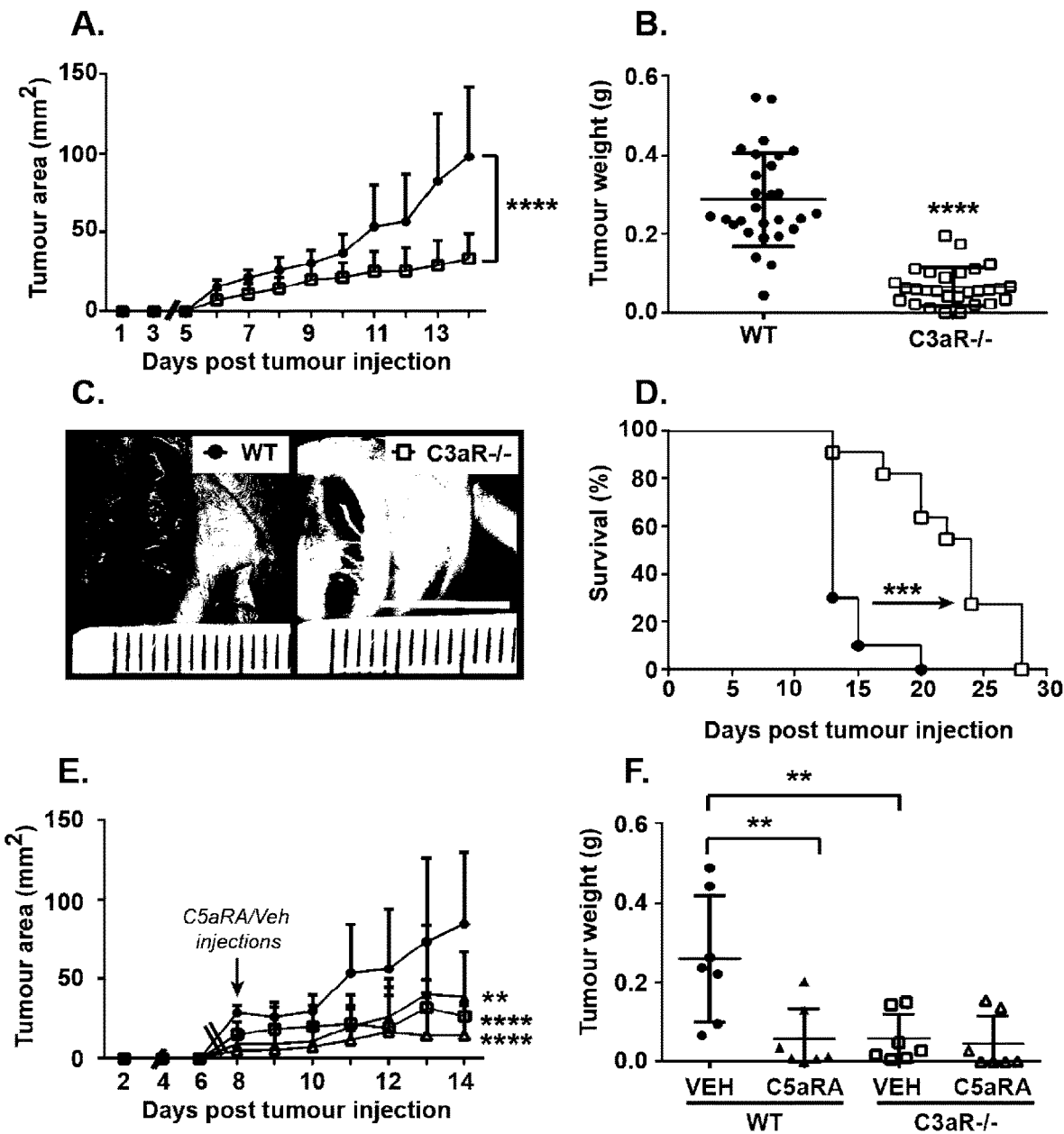
FIGS. 1A to 1F are a graphical representation showing that C3aR deficiency retards B16 melanoma growth.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "a mobilizer of hematopoietic stem cells and/or progenitor cells" means one mobilizer of hematopoietic stem cells and/or progenitor cells or more than one mobilizer of hematopoietic stem cells and/or progenitor cells.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

The terms "administration concurrently" or "administering concurrently" or "co-administering" and the like refer to the administration of a single composition containing two or more active agents, or the administration of each active agent as separate compositions and/or delivered by separate routes either contemporaneously or simultaneously or sequentially within a short enough period of time that the effective result is equivalent to that obtained when all such active agents are administered as a single composition. For example, a C3aR antagonist may be administered together with a mobilizer of hematopoietic stem cells and/or progenitor cells in order to increase in peripheral blood the numbers of leukocytes, which include neutrophils and suitably further include T lymphocytes such as CD4$^+$ T lymphocytes and/or CD8$^+$ T lymphocytes, and which inhibit growth and/or metastasis of a tumor. In another example, C3aR antagonist and a mobilizer of hematopoietic stem cells and/or progenitor cells are administered together with a cancer therapy or agent that inhibits the proliferation, survival or viability of the tumor, to enhance the effects of the C3aR antagonist and the mobilizer. By "sequential" administration is meant a time difference of from seconds, minutes, hours or days between the administration of the two types of molecules or active agents. These molecules or active agents may be administered in any order. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. In certain embodiments, the C3aR antagonist and the mobilizer are administered within about 60 minutes, about 50 minutes, about 40 minutes, about 30 minutes, about 20 minutes, about 10 minutes, about 5 minutes, or about 1 minute of each other or separated in time by about 1 hour, about 2 hours, about 4 hours, about 6 hours, about 10 hours, about 12 hours, about 24 hours, about 36 hours, or about 72 hours, or more. When administered contemporaneously, the agents are suitably administered at the same site on the subject. The term "same site" includes the exact location, but can be within about 0.5 to about 15 centimeters, usually from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell which is capable of producing and secreting polypeptides referred to herein as well as a polynucleotide comprising a nucleotide sequence that encodes this polypeptide. Thus, the term "agent" extends to nucleic acid constructs including vectors such as viral or non-viral vectors, expression vectors and plasmids for expression in and secretion in a range of cells.

An "agranulocytosis medicament" as used herein refers to a composition of matter which reduces the symptoms related to agranulocytosis, prevents the development of agranulocytosis, or treats existing agranulocytosis.

As used herein, the term "alkyl" refers to a straight chain, branched or cyclic saturated hydrocarbon group having 1 to 10 carbon atoms. Where appropriate, the alkyl group may have a specified number of carbon atoms, for example, C1-6alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl, decyl, cyclopropyl, cyclobutyl, cyclopentyl, cyclohexyl and cycloheptyl.

As used herein, the term "alkenyl" refers to a straight-chain, branched or cyclic hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, cyclopentenyl, cyclohexenyl and cyclohexadienyl.

As used herein, "and/or" refers to and encompasses any and all possible combinations of one or more of the associated listed items, as well as the lack of combinations when interpreted in the alternative (or).

An "anemia medicament" as used herein refers to a composition of matter which reduces the symptoms related to anemia, prevents the development of anemia, or treats existing anemia.

The term "antibody" herein is used in the broadest sense and specifically covers monoclonal antibodies, polyclonal antibodies, multispecific antibodies (e.g., bispecific antibodies), antibody fragments, or any other antigen-binding molecule so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target (e.g., a target antigen), wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al. (1991) *Nature* 352:624-628; Marks et al. (1991) *J. Mol. Biol.* 222:581-597; Sidhu et al. (2004) *J. Mol. Biol.* 338(2):299-310; Lee et al. (2004) *J. Mol. Biol.* 340(5):1073-1093; Fellouse (2004) *Proc. Nat. Acad. Sci. USA* 101(34):12467-12472; and Lee et al. (2004) *J. Immunol. Methods* 284(1-2):119-132, and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al. (1993) *Proc. Natl. Acad. Sci. USA* 90:2551; Jakobovits et al. (1993) *Nature* 362:255-258; Bruggemann et al. (1993) *Year in Immuno.* 7:33; U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al. (1992) *Bio/Technology* 10: 779-783; Lonberg et al. (1994) *Nature* 368: 856-859; Morrison (1994) *Nature*, 368: 812-813; Fishwild et al. (1996) *Nature Biotechnology* 14: 845-851; Neuberger (1996) *Nature Biotechnology* 14: 826; and Lonberg and Huszar (1995) *Intern. Rev. Immunol.* 13: 65-93).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855). Chimeric antibodies of interest herein include "primatized" antibodies comprising variable domain antigen-binding sequences derived from a non-human primate (e.g., Old World Monkey, Ape etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) Nature 332:323-329; and Presta (1992) *Curr. Op. Struct. Biol.* 2:593-596.

"Antibody fragments" comprise a portion of an intact antibody, suitably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragment(s).

An antibody "that binds" an antigen of interest (e.g., a surface antigen such as a C3aR of a tumor or a cell of myeloid origin (including neutrophils, mast cells, monocytes, macrophages and dendritic cells) or a non-immune cell) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$)CH$_2$phenyl, and the like and derivatives thereof.

As used herein, "aromatic" or "aryl" is intended to mean any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

In certain instances, substituents may be defined with a range of carbons that includes zero, such as (C$_0$-C$_6$)alkylene-aryl. If aryl is taken to be phenyl, this definition would include phenyl itself as well as, for example, —CH$_2$Ph, —CH$_2$CH$_2$Ph, CH(CH$_3$)CH$_2$CH(CH$_3$)Ph.

It will also be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

Reference herein to "bacteria" or "bacterial infection" includes any bacterial pathogen including emerging bacterial pathogen of vertebrates. Representative bacterial pathogens include without limitation species of: *Acinetobacter, Actinobacillus, Actinomycetes, Actinomyces, Aeromonas, Bacillus, Bacteroides, Bordetella, Borrelia, Brucella* (brucellosis), *Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria, Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague).

As used herein, the term "C3aR antagonist" refers to an agent, the presence of which results in a decrease in the magnitude of a biological activity of C3aR (e.g., a pro-inflammatory function of C3aR, including stimulation of cytokine expression from monocytes such as macrophages, and/or an immunomodulatory function of C3aR such as reducing granulocyte levels, including, for example reducing levels of mobilized neutrophils, levels of neutrophils infiltrating tissues, and activity levels of neutrophils). C3aR antagonists include and encompass any agent that decreases the activity, activation or function of C3aR. In some embodiments, a C3aR antagonist binds to C3aR. In some embodiments, a C3aR antagonist prevents or inhibits the binding of C3a to C3aR. In other embodiments, a C3aR antagonist reduces expression of C3aR. In some embodiments, a C3aR antagonist results in a loss of function of the C3aR. In certain embodiments, the C3aR antagonist binds to C3aR to form a complex that is ineffective in eliciting a physiological response of that receptor, in the same manner as an unoccupied receptor, and optionally does not alter the equilibrium between inactive and active receptor.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

The term "differentiation" of hematopoietic stem cells and/or hematopoietic progenitors as used herein refers to both the change of hematopoietic stem cells into hematopoietic progenitors and the change of hematopoietic progenitors into unipotent hematopoietic progenitors and/or cells having characteristic functions, namely mature cells including leukocytes (e.g., neutrophils and suitably T lymphocytes such as $CD4^+$ T lymphocytes and/or $CD8^+$ T lymphocytes). Differentiation of hematopoietic stem cells into a variety of blood cell types involves sequential activation or silencing of several sets of genes. Hematopoietic stem cells typically choose either a lymphoid or myeloid lineage pathway at an early stage of differentiation.

By "effective amount", in the context of stimulating or enhancing the development, mobilization, proliferation and/or differentiation of a neutrophil-containing leukocyte population (e.g., one that comprises neutrophils and suitably further comprises T lymphocytes such as $CD4^+$ T lymphocytes and/or $CD8^+$ T lymphocytes) that inhibits growth and/or metastasis of a tumor, or of reducing the incidence of a hyperproliferative cell disorder, or of reducing recurrence of a hyperproliferative cell disorder, or of treating or preventing a hyperproliferative cell disorder, is meant the administration of an amount of C3aR antagonist and an amount of a mobilizer of hematopoietic stem cells and/or progenitor cells to an individual, either in a single dose or as part of a series, that is effective for that application; i.e., stimulating or enhancing the development, mobilization, proliferation and/or differentiation of the neutrophil-containing leukocyte population (e.g., one that comprises neutrophils and suitably further comprises T lymphocytes such as $sCD4^+$ T lymphocytes and/or $CD8^+$ T lymphocytes), reducing the incidence of the hyperproliferative cell disorder, reducing recurrence of the hyperproliferative cell disorder, or treating or preventing the hyperproliferative cell disorder, including the prevention of incurring a symptom, holding in check such symptoms, and/or treating existing symptoms, of the hyperproliferative cell disorder. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, the term "function" refers to a biological, enzymatic, or therapeutic function.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "group" as applied to chemical species refers to a set of atoms that forms a portion of a molecule. In some instances, a group can include two or more atoms that are bonded to one another to form a portion of a molecule. A group can be monovalent or polyvalent (e.g., bivalent) to allow bonding to one or more additional groups of a molecule. For example, a monovalent group can be envisioned as a molecule with one of its hydrogen atoms removed to allow bonding to another group of a molecule. A group can be positively or negatively charged. For example, a positively charged group can be envisioned as a neutral group with one or more protons (i.e., $H^+$) added, and a negatively charged group can be envisioned as a neutral group with one or more protons removed. Non-limiting examples of groups include, but are not limited to, alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups. Groups such as alkyl, alkenyl, alkynyl, aryl, and heterocyclyl, whether used alone or in a compound word or in the definition of a group may be optionally substituted by one or more substituents. "Optionally substituted," as used herein, refers to a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, phenylamino, diphenylamino, benzylamino, dibenzylamino, hydrazino, acyl, acylamino, diacylamino, acyloxy, heterocyclyl, heterocycloxy, heterocyclamino, haloheterocyclyl, carboxy ester, carboxy, carboxy amide, mercapto, alkylthio, benzylthio, acylthio and phosphorus-containing groups. As used herein, the term "optionally substituted" may also refer to the replacement of a $CH_2$ group with a carbonyl (C=O) group. Non-limiting examples of optional substituents include alkyl, preferably $C_{1-8}$ alkyl (e.g., $C_{1-6}$ alkyl such as methyl, ethyl, propyl, butyl, cyclopropyl, cyclobutyl, cyclopentyl or cyclohexyl), hydroxy $C_{1-8}$ alkyl (e.g., hydroxymethyl, hydroxyethyl, hydroxypropyl), alkoxyalkyl (e.g., methoxymethyl, methoxyethyl, methoxypropyl, ethoxymethyl, ethoxyethyl, ethoxypropyl etc.) $C_{1-8}$ alkoxy, (e.g., $C_{1-6}$ alkoxy such as methoxy, ethoxy, propoxy, butoxy, cyclopropoxy, cyclobutoxy), halo (fluoro, chloro, bromo, iodo), monofluoromethyl, monochloromethyl, monobromomethyl, difluoromethyl, dichloromethyl, dibromomethyl, trifluoromethyl, trichloromethyl, tribromomethyl, hydroxy, phenyl (which itself may be further substituted, by an optional substituent as described herein, e.g., hydroxy, halo, methyl, ethyl, propyl, butyl, methoxy, ethoxy, acetoxy, amino), benzyl (wherein the $CH_2$ and/or phenyl group may be further substituted as described herein), phenoxy (wherein the $CH_2$ and/or phenyl group may be further substituted as described herein), benzyloxy (wherein the $CH_2$ and/or phenyl group may be further substituted as described herein), amino, $C_{1-8}$ alkylamino (e.g., $C_{1-6}$ alkyl, such as methylamino, ethylamino, propylamino), di $C_{1-8}$ alkylamino (e.g., $C_{1-6}$ alkyl, such as dimethylamino, diethylamino, dipropylamino), acylamino (e.g., $NHC(O)CH_3$), phenylamino (wherein phenyl itself may be further substituted as described herein), nitro, formyl, —C(O)—$C_{1-8}$ alkyl (e.g., $C_{1-6}$ alkyl, such as acetyl), O—C(O)-alkyl (e.g., $C_{1-6}$ alkyl, such as acetyloxy), benzoyl (wherein the $CH_2$ and/or phenyl group itself may be further substituted), replacement of $CH_2$ with C=O, $CO_2H$, $CO_2$ $C_{1-8}$ alkyl (e.g., $C_{1-6}$ alkyl such as methyl ester, ethyl ester, propyl ester, butyl ester), $CO_2$phenyl (wherein phenyl itself may be further substituted), $CONH_2$, CONHphenyl (wherein phenyl itself may be further substituted as described herein), CONHbenzyl (wherein the $CH_2$ and/or phenyl group may be further substituted as described herein), CONH $C_{1-8}$ alkyl (e.g., $C_{1-6}$ alkyl such as methyl amide, ethyl amide, propyl amide, butyl amide), CONH $C_{1-8}$ alkylamine (e.g., $C_{1-6}$ alkyl such as aminomethyl amide, aminoethyl amide, aminopropyl amide, aminobutyl amide), —C(O)heterocyclyl (e.g., —C(O)-1-piperidine, —C(O)-1-piperazine, —C(O)-4-morpholine), —C(O)heteroaryl (e.g., —C(O)-1-pyridine, —C(O)-1-pyridazine, —C(O)-1-pyrimidine, —C(O)-1-pyrazine), CONHdi $C_{1-8}$ alkyl (e.g., $C_{1-6}$alkyl).

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "hematopoietic stem cells" as used herein refers to multipotent stem cells that are capable of differentiating into all blood cells including erythrocytes, leukocytes and platelets. For instance, the term "hematopoietic stem cells" includes and encompasses those contained not only in bone marrow but also in umbilical cord blood derived cells.

The term "hematopoietic progenitors," which is used interchangeably with the term "hematopoietic precursors," refers to those progenitor or precursor cells which are differentiated further than hematopoietic stem cells but have yet to differentiate into progenitors or precursors of respective blood cell lineages (unipotent precursor cells). Thus, "progenitor cell(s)" or "precursor cell(s)" are defined as cells that are lineage-committed, i.e., an individual cell can give rise to progeny limited to a single lineage such as the myeloid or lymphoid lineage. They do not have self-renewal properties. They can also be stimulated by lineage-specific growth factors to proliferate. If activated to proliferate, progenitor cells have life-spans limited to 50-70 cell doublings before programmed cell senescence and death occurs. For example, "hematopoietic progenitors" as used herein include granulocyte/macrophage associated progenitors (colony-forming unit granulocyte, macrophage, CFU-GM), erythroid associated progenitors (burst-forming unit erythroid, BFU-E), megakaryocyte associated progenitors (colony-forming unit megakaryocyte, CFU-Mk), and myeloid associated stem cells (colony-forming unit mixed, CFU-Mix). Hematopoietic progenitor cells possess the ability to differentiate into a final cell type directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage, as daughter cells become differentiated. The isolation of populations of mammalian bone marrow cell populations which are enriched to a greater or lesser extent in pluripotent stem cells has been reported (see for example, C. Verfaillie et al., J. Exp. Med., 172, 509 (1990)).

"Heteroaralkyl" group means alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

The term "heteroaryl" or "heteroaromatic", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, bezofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heterocyclyl" and "heteroaryl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene" refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —$CH_2$pyrrolidin-1-yl, —$(CH_2)_2$piperidin-1-yl, and the like, and derivatives thereof.

The term "lower alkyl" refers to straight and branched chain alkyl groups having from 1 to 6 carbon atoms, such as methyl, ethyl, n-propyl, iso-propyl, n-butyl, tert-butyl, secbutyl, n-pentyl, n-hexyl, 2-methylpentyl, and the like. In some embodiments, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 2-methyl-pentoxy, and the like. Usually, the lower alkoxy group is methoxy or ethoxy.

As used herein the terms "homolog", "homolog" or "homologous" refer to the level of similarity between two or more nucleic acid sequences in terms of percent of sequence identity. Generally, homologs, homologous sequences or sequences with homology refer to nucleic acid sequences that exhibit at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to one another. Alternatively, or in addition, homologs, homologous sequences or sequences with homology refer to nucleic acid sequences that hybridize under medium or high stringency conditions to one another.

The term "hydrocarbyl" as used herein includes any radical containing carbon and hydrogen including saturated, unsaturated, aromatic, straight or branched chain or cyclic including polycyclic groups. Hydrocarbyl includes but is not limited to $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar ($C_1$-$C_8$)alkyl such as benzyl, any of which may be optionally substituted.

As used herein, the term "hyperproliferative cell disorder" refers to a disorder in which cellular hyperproliferation causes or contributes to the pathological state or symptoms of the disorder. Illustrative hyperproliferative cell disorders include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. Exemplary hyperproliferative cell disorders include: cancers; blood vessel proliferative disorders such as restenosis, atherosclerosis, in-stent stenosis, vascular graft restenosis, etc.; fibrotic disorders; psoriasis; inflammatory disorders, e.g., arthritis, etc.; glomerular nephritis; endometriosis; macular degenerative disorders; benign growth disorders such as prostate enlargement and lipomas; autoimmune disorders; and scarring disorders such as post-operative scarring, hypertrophic scarring, keloid scarring and glial scarring. In some embodiments, the hyperproliferative cell disorder is a precancer or a precancerous condition. A "precancer cell" or "precancerous cell" is a cell manifesting a hyperproliferative cell disorder that is a pre-cancer or a precancerous condition. In other embodiments, the hyperproliferative cell disorder is a cancer. The term "cancer" includes primary and metastatic cancer and is used interchangeably herein with the term "neoplastic" to refer to a disease or condition involving cells that metastasize or have the potential to metastasize to distal sites and exhibit phenotypic traits that differ from those of non-neoplastic cells, for example, formation of colonies in a three-dimensional substrate such as soft agar or the formation of tubular networks or web-like matrices in a three-dimensional basement membrane or extracellular matrix preparation, such as Matrigel™. Non-neoplastic cells do not form colonies in soft agar and form distinct sphere-like structures in three-dimensional basement membrane or extracellular matrix preparations. Neoplastic cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. Thus, "non-neoplastic" means that the condition, disease, or disorder does not involve cancer cells. Exemplary cancers includes solid tumors, as well as, hematologic tumors and/or malignancies. A "cancer cell," "cancerous cell" or "neoplastic cell" is a cell manifesting a hyperproliferative cell disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers. Representative cancers contemplated by the present invention include, but are not limited to, sarcomas, melanomas, adenomas, carcinomas of solid tissue (e.g., breast, ovary, prostate, colon, lung, skin, kidney, bladder, pancreas, head and neck) including squamous cell carcinomas of the mouth, throat, larynx, and lung; hypoxic tumors; hematopoietic cancers; nervous system cancers; benign lesions such as papillomas; leukemias, and lymphomas, illustrative examples of which include carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma. In some embodiments, the hyperproliferative cell disorder is a non-neoplastic disorder in which cellular hyperproliferation causes or contributes to the pathological state or symptoms of the disorder.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The term "immunocompromised" as used herein refers to a subject with an innate, acquired, or induced inability to develop a normal immune response. An immunocompromised subject, therefore, has a weakened or impaired immune system relative to one of a normal subject. A subject with a weakened or impaired immune system has an "immunodeficiency" or "immunocompromised condition," which is associated with a primary or secondary deficiency, induced or non-induced, in one or more of the elements of the normal immune defense system. An immunocompromised condition is commonly due to a medical treatment, e.g., radiation therapy, chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection. However, it will be understood that the phrase "risk of acquiring an immunocompromised condition resulting from a medical treatment" refers only to medical treatments that leads to or confers an immunocompromised condition, especially chemotherapy or other immunosuppressing treatment, such as induced by treatment with radiation, steroids, cyclophosphamide, azathioprine, methotrexate, cyclosporine or rapamycin. The presence of an immunocompromised condition in a subject can be diagnosed by any suitable technique known to persons of skill the art. Strong indicators that an immunocompromised condition may be present is when rare diseases occur or the subject gets ill from organisms that do not normally cause diseases, especially if the subject gets repeatedly infected. Other possibilities are typically considered, such as recently acquired infections—for example, HIV, hepatitis, tuberculosis, etc. Generally, however, definitive diagnoses are based on laboratory tests that determine the exact nature of the immunocompromised condition. Most tests are performed on blood samples. Blood contains antibodies, lymphocytes, phagocytes, and complement components—all of the major immune components that might cause immunodeficiency. A blood cell count will determine if the number of phagocytic cells or lymphocytes is below normal. Lower than normal counts of either of these two cell types correlates with an immunocompromised condition. The blood cells are also checked for their appearance. Occasionally, a subject may have normal cell counts, but the cells are structurally defective. If the lymphocyte cell count is low, further testing is usually conducted to determine whether any particular type of lymphocyte is lower than normal. A lymphocyte proliferation test may be conducted to determine if the lymphocytes can respond to stimuli. The failure to respond to stimulants correlates with an immunocompromised condition. Antibody levels and complement levels can also be determined for diagnosing the presence of an immunocompromised condition. However, it shall be understood that the methods of the present invention are not predicated upon diagnosing the absence of an immunocompromised condition in the subjects to be treated.

Reference herein to "immuno-interactive" includes reference to any interaction, reaction, or other form of association between molecules and in particular where one of the molecules is, or mimics, a component of the immune system.

Reference herein to an "infectious agent," "infectious organism," "microbe" or "pathogen" includes any one or more species or subspecies of bacterium, fungus, virus, algae, parasite, (including ecto- or endo-parasites) prion, oomycetes, slime, moulds, nematodes, *mycoplasma* and the like. The present invention is particularly suited to treating or preventing mixed infections by more than one microbe. Pathogenic algae include Prototheca and Pfiesteria. Also includes within the scope of these terms are prion proteins causing conditions such as Creutzfeldt-Jakob disease. As the skilled artisan will appreciate, pathogenicity or the ability of a classically non-pathogenic agent to infect a subject and cause pathology can vary with the genotype and expression profile of the infectious agent, the host and the environment. Fungal pathogens include without limitation species of the following genera: *Absidia, Acremonium, Aspergillus, Basidiobolus, Bipolaris, Blastomyces, Candida* (yeast), *Cladophialophora, Coccidioides, Cryptococcus, Cunninghamella, Curvularia, Epidermophyton, Exophiala, Exserohilum, Fonsecaea, Fusarium, Geotrichum, Histoplasma, Hortaea, Lacazia, Lasiodiplodia, Leptosphaeria, Madurella, Malassezia, Microsporum, Mucor, Neotestudina, Onychocola, Paecilomyces, Paracoccidioides, Penicillium, Phialophora, Piedraia, Piedra, Pityriasis, Pneumocystis, Pseudallescheria, Pyrenochaeta, Rhizomucor, Rhizopus, Rhodotorula, Scedosporium, Scopulariopsis, Scytalidium, Sporothrix, Trichophyton, Trichosporon* and *Zygomycete*. Pathogenic conditions include any deleterious condition that develops as a result of infection with an infectious organism.

As used herein, the term "interact" includes close contact between molecules that results in a measurable effect, e.g., the binding or association of one molecule to another or a reaction of one molecule with another.

By "isolated" is meant material that is substantially or essentially free from components that normally accompany it in its native state.

The term "loss-of-function", as used herein, refers to a diminishment in the level of expression of a gene that leads to a reduction or abrogation of the function of that gene.

As used herein, a "mobilizer of hematopoietic stem cells and/or progenitor cells," "mobilizing agent" or "mobilizer" are used interchangeably to refer to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of hematopoietic stem cells or hematopoietic progenitor/precursor cells in the peripheral blood.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

A "neutropenia medicament" as used herein refers to a composition of matter which reduces the symptoms related to neutropenia, prevents the development of neutropenia, or treats existing neutropenia.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably connected" or "operably linked" as used herein refers to a juxtaposition wherein the components so described are in a relationship permitting them to function in their intended manner. For example, a transcriptional control sequence "operably linked" to a coding sequence or non-coding sequence refers to positioning and/or orientation of the transcriptional control sequence relative to the coding or non-coding sequence to permit expression of the coding or non-coding sequence under conditions compatible with the transcriptional control sequence.

The term "pharmaceutically acceptable" as used herein refers to a compound or combination of compounds that will not impair the physiology of the recipient human or animal to the extent that the viability of the recipient is compromised. Suitably, the administered compound or combination of compounds will elicit, at most, a temporary detrimental effect on the health of the recipient human or animal.

By "pharmaceutically acceptable carrier" is meant a pharmaceutical vehicle or solvent comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like. Illustrative vehicles or solvents include without limitation water, saline, physiological saline, ointments, creams, oil-water emulsions, gels, or any other vehicle/solvent or combination of vehicles/solvents and compounds known to one of skill in the art that is pharmaceutically and physiologically acceptable to the recipient human or animal. "Pharmaceutically acceptable carriers" also include within their scope drug delivery systems such as nanoparticles, hydrogels, microspheres, liposomes, dendrimers, polymers, and micelles.

Similarly, a "pharmacologically acceptable" salt, ester, amide, prodrug or derivative of a compound as provided herein is a salt, ester, amide, prodrug or derivative that this not biologically or otherwise undesirable.

Pathogenic "protozoa" include, without limitation, *Trypanosoma, Leishmania, Giardia, Trichomonas, Entamoeba, Naegleria, Acanthamoeba, Plasmodium, Toxoplasma, Cryptosporidium, Isospora* and *Balantidium*.

Larger pathogenic "parasites" include those from the phyla Cestoda (tapeworms), Nematoda and Trematoda (flukes). Pathogenic trematodes are, for example, species of the following genera; *Schistosoma, Echinostoma, Fasciolopsis, Clonorchis, Fasciola, Opisthorchis* and *Paragonimus*. Cestode pathogens include, without limitation, species from the following orders; Pseudophyllidea (e.g., *Diphyllobothrium*) and Cyclophyllidea (e.g., *Taenia*). Pathogenic nematodes include species from the orders; Rhabditida (e.g., *Strongyloides*), Strongylida (e.g., *Ancylostoma*), Ascaridia (e.g., *Ascaris, Toxocara*), Spirurida (e.g., *Dracunculus, Brugia, Onchocerca, Wucheria*) and Adenophorea (e.g., *Trichuris* and *Trichinella*).

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

As used herein, "racemate" refers to a mixture of enantiomers.

As used herein, "recurrence of a hyperproliferative cell disorder" refers to a return of a hyperproliferative cell disorder following treatment, and includes return of the hyperproliferative cell disorder in the primary organ, as well as distant recurrence, where the hyperproliferative cell disorder returns outside of the primary organ.

The term "reducing the incidence" refers to inhibiting the development and/or reducing the progression, or magnitude, of a condition (e.g., a hyperproliferative cell disorder).

"Reducing recurrence" refers to a reduction in frequency, severity and/or quantity of one or more recurrent symptoms in a subject with a condition (e.g., a hyperproliferative cell disorder).

The terms "salts," "derivatives" and "prodrugs" includes any pharmaceutically acceptable salt, ester, hydrate, or any other compound which, upon administration to the recipient, is capable of providing (directly or indirectly) a compound of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicyclic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl, and butyl chlorides, bromides and iodides; dialkyl sulfates like dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs and derivatives can be carried out by methods known in the art. For example, metal salts can be prepared by reaction of a compound of the invention with a metal hydroxide. An acid salt can be prepared by reacting an appropriate acid with a compound of the invention.

The term "selective" refers to compounds that inhibit or display antagonism towards C3aR without displaying substantial inhibition or antagonism towards another complement receptor (e.g., $C_5aR$). Accordingly, a compound that is selective for C3aR exhibits inhibition or antagonism of C3aR that is greater than about 2-fold, 5-fold, 10-fold, 20-fold, 50-fold or greater than about 100-fold with respect to inhibition or antagonism of complement receptor (e.g., $C_5aR$). In some embodiments, selective compounds display at least 50-fold greater inhibition or antagonism towards C3aR than towards another complement receptor (e.g., $C_5aR$). In still other embodiments, selective compounds inhibit or display at least 100-fold greater inhibition or antagonism towards C3aR than towards another complement receptor (e.g., $C_5aR$). In still other embodiments, selective compounds display at least 500-fold greater inhibition or antagonism towards C3aR than towards another complement receptor (e.g., $C_5aR$). In still other embodiments, selective compounds display at least 1000-fold greater inhibition or antagonism towards C3aR than towards another complement receptor (e.g., $C_5aR$).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 1 below.

TABLE 1

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP. Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

As used herein a "small molecule" refers to a composition that has a molecular weight of less than 3 kilodaltons (kDa), and typically less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, less than 1.5 kilodaltons, or even less than about 1 kDa.

"Stem cells" refer to cells, which are not terminally differentiated and are therefore able to produce cells of other types. Stem cells are generally divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew as well as differentiate to regenerate adult tissues. "Multipotent stem cells" are also referred to as "unipotent" and can only become particular types of cells, such as blood cells or bone cells. The term "stem cells", as used herein, refers to pluripotent stem cells capable of self-renewal.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

"Subjects" contemplated in the present invention include any animal of commercial humanitarian or epidemiological interest including conveniently, primates, livestock animals (such as sheep, cows, horses, donkeys, pigs, fish and birds), laboratory test animals (such as mice, rabbits, guinea pigs and hamsters and the like), companion animals (such as dogs and cats), or captive wild animals. Avian species include poultry birds and caged avian species. In some embodiments the subject is a mammalian animal. In other embodiments, the subject is a human subject. The present composition and methods have applications in human and veterinary medicine, domestic or wild animal husbandry, cosmetic or aesthetic treatments for the skin after injury or surgery.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

As used herein, the term "synergistic" means that the therapeutic effect of a C3aR antagonist when administered in combination with a mobilizer of hematopoietic stem cells and/or progenitor cells (or vice-versa) is greater than the predicted additive therapeutic effects of the C3aR antagonist and the mobilizer when administered alone. The term "synergistically-effective amount" as applied to a C3aR antagonist and a mobilizer of hematopoietic stem cells and/or progenitor cells refers to the amount of each component in a composition (generally a pharmaceutical composition), which is effective for stimulating or enhancing the development, mobilization, proliferation and/or differentiation of a neutrophil-containing leukocyte population that inhibits growth and/or metastasis of a tumor and/or which is effective for stimulating or enhancing mobilization of hematopoietic stem cells and/or progenitor cells from the bone marrow into the peripheral blood, which stem cells or progenitor cells differentiate to form such a population, wherein the amounts of each component produces an effect which does not intersect, in a dose-response plot of the dose of C3aR antagonist versus a dose of the mobilizer versus stimulating or enhancing the development, mobilization, proliferation and/or differentiation of a neutrophil (e.g., neutrophil and/or T lymphocyte such as a $CD4^+$ T lymphocyte or $CD8^+$ T lymphocyte)-containing leukocyte population that inhibits growth and/or metastasis of a tumor, or reducing the incidence of a hyperproliferative cell disorder, or reducing recurrence of a hyperproliferative cell disorder, or treating or preventing a hyperproliferative cell disorder, either the dose C3aR antagonist axis or the dose mobilizer axis. The dose response curve used to determine synergy in the art is described for example by Sande et al. (see, p. 1080-1105 in A. Goodman et al., ed., the Pharmacological Basis of Therapeutics, MacMillan Publishing Co., Inc., New York (1980)). The optimum synergistic amounts can be determined, using a 95% confidence limit, by varying factors such as dose level, schedule and response, and using a computer-generated model that generates isobolograms from the dose response curves for various combinations of the C3aR antagonist and the mobilizer. In some embodiments, the highest mobilization of a neutrophil-containing leukocyte population that inhibits growth and/or metastasis of a tumor on the dose response curve correlates with the optimum dosage levels.

A "thrombocytopenia medicament" as used herein refers to a composition of matter which reduces the symptoms related to thrombocytopenia, prevents the development of thrombocytopenia, or treats existing thrombocytopenia.

As used herein, the term "transcriptional control sequence" refers to nucleic acid sequences, such as initiator sequences, enhancer sequences and promoter sequences, which induce, repress, or otherwise control the transcription of protein encoding nucleic acid sequences to which they are operably-linked.

By "treatment," "treat," "treated," "treating" and the like is meant to include both therapeutic and prophylactic treatment, including the administration of medicine or the performance of medical procedures with respect to a patient, for either prophylaxis (prevention) or to cure or reduce the extent of or likelihood of occurrence of the infirmity or malady or condition or event in the instance where the patient is afflicted.

The term "tumor," as used herein, refers to any neoplastic cell growth and proliferation, whether malignant or benign, and all pre-cancerous and cancerous cells and tissues. The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "early stage cancer" is meant a cancer that is not invasive or metastatic or is classified as a Stage 0, I, or II cancer. The term "late stage cancer" generally refers to a Stage III or Stage IV cancer, but can also refer to a Stage II cancer or a substage of a Stage II cancer. One skilled in the art will appreciate that the classification of a Stage II cancer as either an early stage cancer or a late stage cancer depends on the particular type of cancer. Illustrative examples of cancer include, but are not limited to, breast cancer, prostate cancer, ovarian cancer, cervical cancer, pancreatic cancer, colorectal cancer, lung cancer, hepatocellular cancer, gastric cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is breast cancer.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells, as well as well as preserved tumor samples, such as formalin-fixed, paraffin-embedded tumor samples or frozen tumor samples. The term encompasses cells that are the progeny of the patient's tumor cells, e.g., cell culture samples derived from primary tumor cells or circulating tumor cells. The term encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

Reference herein to "a virus" includes any virus or viral pathogen or emerging viral pathogen. Viral families contemplated include Adenoviridae, African swine fever-like viruses, Arenaviridae (such as viral hemorrhagic fevers, Lassa fever), Astroviridae (astroviruses) Bunyaviridae (La Crosse), Caliciviridae (Norovirus), Coronaviridae (Corona virus), Filoviridae (such as Ebola virus, Marburg virus), Parvoviridae (B19 virus), Flaviviridae (such as hepatitis C virus, Dengue viruses), Hepadnaviridae (such as hepatitis B virus, Deltavirus), Herpesviridae (herpes simplex virus, varicella zoster virus), Orthomyxoviridae (influenza virus) Papovaviridae (papilloma virus) Paramyxoviridae (such as human parainfluenza viruses, mumps virus, measles virus, human respiratory syncytial virus, Nipah virus, Hendra virus), Picornaviridae (common cold virus), Poxviridae (small pox virus, orf virus, monkey poxvirus) Reoviridae (rotavirus) Retroviridae (human immunodeficiency virus) Parvoviridae (parvoviruses) Papillomaviridae, (papillomaviruses) alphaviruses and Rhabdoviridae (rabies virus).

As used herein, underscoring or italicizing the name of a gene shall indicate the gene, in contrast to its protein product, which is indicated by the name of the gene in the absence of any underscoring or italicizing. For example, "C3aR" shall mean the C3aR gene, whereas "C3aR" shall indicate the protein product or products generated from transcription and translation and alternative splicing of the "C3aR" gene.

Each embodiment described herein is to be applied mutatis mutandis to each and every embodiment unless specifically stated otherwise.

2. Abbreviations

CFC=colony-forming cells
C3a=complement 3a
C3aR=complement 3a receptor
HSC=hematopoietic stem cells
HSPC=hematopoietic stem and progenitor cells
MDSC=myeloid-derived suppressor cells
d=day
h=hour
s=seconds
i.v.=intravenous
i.p.=intraperitoneal
s.c.=subcutaneous
rHu=recombinant human 3. Compositions and Methods for Enhancing Hematopoietic Function The present invention is based in part on the surprising discovery that antagonism, including loss of function, of C3aR leads to increased infiltration of a tumor by a leukocyte population in peripheral blood that inhibits growth and/or metastasis of the tumor. The present inventors have also found that a mobilizer of hematopoietic stem cells and/or progenitor cells mobilizes hematopoietic stem and progenitor cells (HSPCs) from the bone marrow into the peripheral blood, which, in the presence of the C3aR antagonist, give rise to the anti-tumor leukocyte population. The increased mobilization may also result in increased HSPCs mobilizing from the peripheral blood to particular tissues or organs such as the lymph nodes, the heart, the lung, the liver, the skin, the spleen, small and large intestines, the stomach, or the pancreas, in which a tumor may reside.

Increasing the number or mobility of HSPCs may increase the rate of differentiation of HSPCs into various cell lineages, including increasing the number of common myeloid progenitor cells in the bone marrow or the peripheral blood. The differentiation of HSPCs may also lead to an increase in the number of granulocyte/macrophage progenitor cells or megakaryocyte/erythrocyte progenitor cells in the bone marrow or peripheral blood. The HSPCs may differentiate into a common lymphoid precursor. The increase in number of common myeloid progenitor cells may lead to a differentiation into granulocyte/macrophage progenitor cells or megakaryocyte/erythrocyte progenitor cells. The granulocyte/macrophage progenitor cells may further differentiate into granulocytes such as neutrophils, eosinophils, basophils, tissue precursor cells, monocytes, and immature dendritic cells. In specific embodiments, the increase in number of common myeloid progenitor cells leads to a differentiation into granulocyte/macrophage progenitor cells, including the differentiation of neutrophils with anti-tumor activity.

Thus, in accordance with the present invention, methods and compositions are provided that take advantage of a C3aR antagonist and a mobilizer of hematopoietic stem cells and/or progenitor cells for stimulating or enhancing the development, mobilization, proliferation and/or differentiation of a neutrophil-containing leukocyte population that inhibits growth and/or metastasis of a tumor, for enhancing an immune response to a tumor, for reducing the incidence of a hyperproliferative cell disorder, for reducing recurrence of a hyperproliferative cell disorder, and/or for treating or preventing a hyperproliferative cell disorder.

3.1 C3aR Antagonists

C3aR antagonists that are useful in the methods and compositions of the present invention include and encompass any active agent that reduces the accumulation, function or stability of C3aR; or decrease expression of the C3aR gene, and such inhibitors include without limitation, small molecules and macromolecules such as nucleic acids, peptides, polypeptides, peptidomimetics, carbohydrates, polysaccharides, lipopolysaccharides, lipids or other organic (carbon containing) or inorganic molecules.

In some embodiments, the C3aR antagonist is an antagonistic nucleic acid molecule that functions to inhibit the transcription or translation of C3aR transcripts. Representative transcripts of this type include nucleotide sequences corresponding to any one the following sequences: (1) human C3aR nucleotide sequences as set forth for example in GenBank Accession Nos. NM_004054.2, BC020742.1, and Z73157.1; (2) nucleotide sequences that share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (1); (3) nucleotide sequences that hybridize under at least low, medium or high stringency conditions to the sequences referred to in (1); (4) nucleotide sequences that encode any one of the following amino acid sequences: human C3aR amino acid sequences as set forth for example in GenPept Accession Nos. NP_004045.1, AAH20742.1 and CAA97504.1; (5) nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity with any one of the sequences referred to in (4); and nucleotide sequences that encode an amino acid sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with any one of the sequences referred to in (4).

Illustrative antagonist nucleic acid molecules include antisense molecules, aptamers, ribozymes and triplex forming molecules, RNAi and external guide sequences. The nucleic acid molecules can act as effectors, inhibitors, modulators, and stimulators of a specific activity possessed by a target molecule, or the functional nucleic acid molecules can possess a de novo activity independent of any other molecules.

Antagonist nucleic acid molecules can interact with any macromolecule, such as DNA, RNA, polypeptides, or carbohydrate chains. Thus, antagonist nucleic acid molecules can interact with C3aR mRNA or the genomic DNA of C3aR or they can interact with a C3aR polypeptide. Often antagonist nucleic acid molecules are designed to interact with other nucleic acids based on sequence homology between the target molecule and the antagonist nucleic acid molecule. In other situations, the specific recognition between the antagonist nucleic acid molecule and the target molecule is not based on sequence homology between the antagonist nucleic acid molecule and the target molecule, but rather is based on the formation of tertiary structure that allows specific recognition to take place.

In some embodiments, anti-sense RNA or DNA molecules are used to directly block the translation of C3aR by binding to targeted mRNA and preventing protein translation. Antisense molecules are designed to interact with a target nucleic acid molecule through either canonical or non-canonical base pairing. The interaction of the antisense molecule and the target molecule may be designed to promote the destruction of the target molecule through, for example, RNAseH mediated RNA-DNA hybrid degradation. Alternatively the antisense molecule may be designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Non-limiting methods include in vitro selection experiments and DNA modification studies using DMS and DEPC. In specific examples, the antisense molecules bind the target molecule with a dissociation constant ($K_d$) less than or equal to $10^{-6}$, $10^{-8}$, $10^{-10}$, or $10^{-12}$. In specific embodiments, antisense oligodeoxyribonucleotides derived from the translation initiation site, e.g., between −10 and +10 regions are employed.

Aptamers are molecules that interact with a target molecule, suitably in a specific way. Aptamers are generally small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kds from the target molecule of less than $10^{-12}$ M. Suitably, the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is desirable that an aptamer have a $K_d$ with the target molecule at least 10-, 100-, 1000-, 10,000-, or 100,000-fold lower than the $K_d$ with a background-binding molecule. A suitable method for generating an aptamer to a target of interest (e.g., PHD, FIH-1 or vHL) is the "Systematic Evolution of Ligands by EXponential Enrichment" (SELEX™). The SELEX™ method is described in U.S. Pat. Nos. 5,475,096 and 5,270,163 (see also WO 91/19813). Briefly, a mixture of nucleic acids is contacted with the target molecule under conditions favorable for binding. The unbound nucleic acids are partitioned from the bound nucleic acids, and the nucleic acid-target complexes are dissociated. Then the dissociated nucleic acids are amplified to yield a ligand-enriched mixture of nucleic acids, which is subjected to repeated cycles of binding, partitioning, dissociating and amplifying as desired to yield highly specific high affinity nucleic acid ligands to the target molecule.

In other embodiments, anti-C3aR ribozymes are used for catalyzing the specific cleavage of C3aR RNA. The mechanism of ribozyme action involves sequence specific hybridization of the ribozyme molecule to complementary target RNA, followed by a endonucleolytic cleavage. There are several different types of ribozymes that catalyze nuclease or nucleic acid polymerase type reactions, which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Representative ribozymes cleave RNA or DNA substrates. In some embodiments, ribozymes that cleave RNA substrates are employed. Specific ribozyme cleavage sites within potential RNA targets are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base pairing. Triplex molecules are preferred because they can bind target regions with high affinity and specificity. It is generally desirable that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNAse P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In other embodiments, RNA molecules that mediate RNA interference (RNAi) of a C3aR gene or C3aR transcript can be used to reduce or abrogate gene expression. RNAi refers to interference with or destruction of the product of a target gene by introducing a single-stranded or usually a double-stranded RNA (dsRNA) that is homologous to the transcript of a target gene. RNAi methods, including double-stranded RNA interference (dsRNAi) or small interfering RNA (siRNA), have been extensively documented in a number of organisms, including mammalian cells and the nematode *C. elegans* (Fire et al., 1998. *Nature* 391, 806-811). In mammalian cells, RNAi can be triggered by 21- to 23-nucleotide (nt) duplexes of small interfering RNA (siRNA) (Chiu et al., 2002 *Mol. Cell*. 10:549-561; Elbashir et al., 2001. *Nature* 411:494-498), or by micro-RNAs (miRNA), functional short-hairpin RNA (shRNA), or other dsRNAs which are expressed in vivo using DNA templates with RNA polymerase III promoters (Zeng et al., 2002. *Mol. Cell* 9:1327-1333; Paddison et al., 2002. *Genes Dev.* 16:948-958; Lee et al., 2002. *Nature Biotechnol.* 20:500-505; Paul et al., 2002. *Nature Biotechnol.* 20:505-508; Tuschl, T., 2002. *Nature Biotechnol.* 20:440-448; Yu et al., 2002. *Proc. Natl. Acad. Sci. USA* 99(9):6047-6052; McManus et al., 2002. *RNA* 8:842-850; Sui et al., 2002. *Proc. Natl. Acad. Sci. USA* 99(6):5515-5520).

In specific embodiments, dsRNA per se and especially dsRNA-producing constructs corresponding to at least a portion of a C3aR gene are used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a C3aR gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts, which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In some embodiments, RNA molecules of about 21 to about 23 nucleotides, which direct cleavage of specific mRNA to which they correspond, as for example described by Tuschl et al. in U.S. 2002/0086356, can be utilized for mediating RNAi. Such 21- to 23-nt RNA molecules can comprise a 3' hydroxyl group, can be single-stranded or double stranded (as two 21- to 23-nt RNAs) wherein the dsRNA molecules can be blunt ended or comprise overhanging ends (e.g., 5', 3').

In some embodiments, the antagonist nucleic acid molecule is a siRNA. siRNAs can be prepared by any suitable method. For example, reference may be made to International Publication WO 02/44321, which discloses siRNAs capable of sequence-specific degradation of target mRNAs when base-paired with 3' overhanging ends, which is incorporated by reference herein. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER™ siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which is incorporated herein by reference.

Illustrative RNAi molecules including anti-C3aR siRNA and shRNA are available commercially from Santa Cruz Biotechnology, Inc. (Santa Cruz, Calif., USA) and OriGene Technologies, Inc. (Rockville, Md., USA).

Also contemplated as C3aR antagonists are antibody or antibody fragment that are immuno-interactive or directed against C3a or C3aR that can reduce C3a-C3aR interactions (e.g., anti-C3a or anti-C3aR antibodies or antibody fragments). Non-limiting examples of antibodies of the invention, include MAb anti-C3a from Quidel, San Diego, Calif., and anti-human C3aR antibodies hC3aRZ1 and hC3aRz2, as described in Kacani, L. et al., J. Immunol. (2001) 166:3410-3415. In specific embodiments, a C3aR antibody or antibody fragment are selected from antibodies and antibody fragments described by Rosen, C. A. in U.S. Publication No. 2009/0035319, which is hereby incorporated by reference herein in its entirety. Exemplary antibodies and antibody fragments of this type comprise:

(a) an amino acid sequence that is at least 90% identical to the amino acid sequence of the VH domain of the scFv amino acid sequence:

(i) [SEQ ID NO: 1]
EVQLVQSGAEVRKPGASVKVSCKASGYSFTNYGITWVRQAPGQGLEWMGW

ISGYNGDTNYAQKLQGRVTMTTDTSTNTAYMELRSLRSDDTAIYYCTRDL

PGLNWAYSYDYMDVWGRGTLVTVSSGGGGSGGGGSGGGGSAQAVLTQPSS

LSASPGTSASLTCTLRSGINVGTYRIYWYQQKPGSPPHFLLRYKSDSDKQ

QGSGVPSRFSGSKDASANAGILLISGLQSDDEADYYCMIWHSSAWVFGGG

TKVTVLG;
or (ii) [SEQ ID NO: 2]
QVQLVESGGGLVKPGGSLRLSCAASGFTFSDYYMSWIRQAPGKGLEWVSY

ISSSSSYTNYADSVKGRFTISRDNAKNSLYLQMNSLRAEDTAVYYCARGP

DYDSYDAFDIWGKGTLVTVSLGGGGSGGGGSGGGGSQSVLTQPPSVSAAP

GQKVTISCSGSTSNIGNNYVSWYQQHPGKAPKLMIYDVSKRPSGVPDRFS

GSKSGNSVSLDISGLQSEDEADYYCAAWDDSLSEFLFGTGTKLTVLG;

(b) an amino acid sequence that is at least 90% identical to the amino acid sequence of the VL domain of the scFv amino acid sequence set forth in SEQ ID NO: 1 or SEQ ID NO: 2; or (c) both (a) and (b).

The present invention also contemplates small molecule agents that antagonize the function of C3aR, non-limiting examples of which include the $N^2$-[(2,2-diphenylethoxy) acetyl]-1-arginine (SB 290157, as described for example in Ames et al., J Immunol 2001; 166:6341-6348), and the C3aR antagonists disclosed in U.S. Pat. Nos. 5,942,405 and 6,489,339, each of which is expressly incorporated herein by reference in its entirety.

In some embodiments, small molecule C3aR antagonists are selected from the aryl substituted imidazo [4,5-c] pyridine compounds, as disclosed for example by Butler, T. W. in International Publication WO 2007/034277, which is expressly incorporated herein by reference in its entirety. Compounds disclosed in WO 2007/034277 are represented by formula (I):

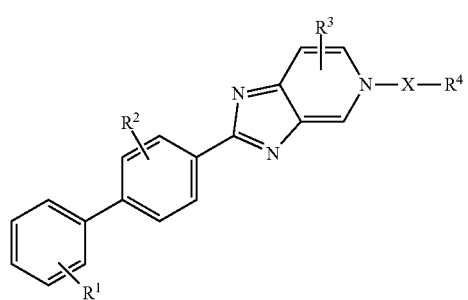

or a pharmaceutically acceptable salt thereof, wherein:

X represents a single bond or a $C_1$-$C_6$ alkylene optionally containing one or more heteroatoms selected from the group consisting of O, S, and N, with the proviso that the heteroatom is not linked to the pyridyl nitrogen of the imidazo[4, 5-c] pyridine core;

$R^1$ represents one or more substituents selected from the group consisting of hydrogen, halo, hydroxyl, C(O)R$_2$, C(O)OR$_2$, N(R$_2$)$_2$, NHR$_2$, C(O)NHR$_2$, C(O)(R$_7$J$_2$, cyano, nitro, optionally substituted ($C_1$-$C_6$) alkyl, optionally substituted ($C_3$-$C_{10}$) cycloalkyl, optionally substituted 3-10-membered heterocycloalkyl, ($C_1$-$C_6$) acylamino, SO$_2$N(R$_2$)$^˄_1$ SO$_2$NHR$_2$, O—($C_1$-$C_6$) alkyl, 8O$_2$(($C_1$-$C_6$) alkyl), and S(O)($C_1$-$C_6$ alkyl); R$_2$ is hydrogen, halo, ($C_1$-$C_6$) alkyl, cyano, hydroxyl, 0-(($C_1$-$C_6$) alkyl), nitro, NH$_2$, NH($C_1$-$C_6$ alkyl), N($C_1$-$C_6$ alkyl)$_2$, C(O)NH($C_1$-$C_6$ alkyl), C(O)N($C_1$-$C_6$ alkyl)$_2$, NHC(O)($C_1$-$C_6$ alkyl), C(O)($C_1$-$C_6$ alkyl), SO$_2$NH($C_1$-$C_6$ alkyl), OR SO$_2$N($C_1$-$C_6$ alkyl)$_2$;

R$_3$ is hydrogen, halo, ($C_1$-$C_6$) alkyl, cyano, hydroxyl, OR O—($C_1$-$C_6$ alkyl);

R$_4$ is hydrogen, optionally substituted ($C_1$-$C_6$) alkyl, optionally substituted ($C_2$-$C_{10}$) alkenyl, optionally substituted ($C_2$-$C_{10}$) alkynyl, CH$_2$CN, CH$_2$C(O)($C_1$-$C_6$ alkyl), optionally substituted 5-10-membered heteroaryl, optionally substituted ($C_6$-$C_{10}$) aryl, C(O)-optionally substituted 5-10-membered heteroaryl, C(O)-optionally substituted ($C_6$-$C_{10}$) aryl, CH(OH)-optionally substituted 5-10-membered heteroaryl, C(O)O—($C_1$-$C_6$ alkyl), C(O)($C_1$-$C_6$ alkyl), OH, NH$_2$, —CHOH—($C_1$-$C_6$ alkyl), C(N—OCH$_3$)($C_1$-$C_6$ alkyl), ($C_1$-$C_6$) alkoxy-($C_2$-$C_6$) alkenylene-C(O)O—($C_1$-$C_6$ alkyl), C(O)NH$_2$, C(O)NH—($C_1$-$C_6$ alkyl), or C(O)N($C_1$-$C_6$ alkyl)$_2$; with the proviso that if X is a single bond and R$_4$ contains a heteroatom, the heteroatom is not linked to the pyridyl nitrogen of the imidazo[4,5-c] pyridine core; or R$_3$ and R$_4$, taken together with the ring carbon attached to R$_3$, the nitrogen attached to the ring carbon, and X, form an optionally substituted 3-10-membered heterocycloalkyl or an optionally substituted 5-10-membered heteroaryl when X is a single bond, and form an optionally substituted 3-10-membered heterocycloalkyl when X is a $C_1$-Ce alkylene;

with the proviso that if X is a single bond and R$_4$ contains a heteroatom, the heteroatom is not linked to the pyridyl nitrogen of the imidazo[4,5-c] pyridine core; and R$_7$, independently for each occurrence, is selected from the group consisting of H, optionally substituted ($C_1$-$C_{10}$) alkyl, optionally substituted ($C_2$-$C_{10}$) alkenyl, optionally substituted ($C_2$-$C_{10}$) alkynyl, ($C_6$-$C_{10}$) aryl, optionally substituted 5-10-membered heteroaryl, optionally substituted ($C_3$-$C_{10}$) cycloalkyl, and optionally substituted 3-10-membered heterocycloalkyl.

Representative compounds falling within the scope of formula (I) are suitably selected from: 2-(3',4'-dimethyl-biphenyl-4-yl)-3H-imidazo[4,5-c]pyridine; 2-(3',4'-dimethyl-biphenyl-4-yl)-5-methyl-5H-imidazo[4,5-c]pyridine; [2-(3',4'-dimethyl-biphenyl-4-yl)-imidazo[4,5-c]pyridin-5-yl]-acetic acid methyl ester; [2-(3',4'-dimethyl-biphenyl-4-yl)-imidazo[4,5-c]pyridin-5-yl]-acetonitrile; 5'-allyl-2-(3', 4'-dimethyl-biphenyl-4-yl)-5H-imidazo[4,5-c]pyridine; 1-[2-(3',4'-Dimethyl-biphenyl-4-yl)-imidazo[4,5-c]pyridin-5-yl]-propan-2-one; 2-(3',4'-dimethyl-biphenyl-4-yl)-5-prop-2-ynyl-5H-imidazo[4,5-c]pyridine; 4-[2-(3',4'-dimethyl-biphenyl-4-yl)-imidazo[4,5-:c]pyridin-5-yl]-3-ethoxy-but-2-enoic acid ethyl ester; 5-benzyl-2-(3',4'-dimethyl-biphenyl-4-yl)-5H-imidazo[4,5-c]pyridine; 2-(3', 4'-dimethyl-biphenyl-4-yl)-5-pyridin-3-ylmethyl-5H-imidazo[4,5-c]pyridine; 2-(3',4'-dimethyl-biphenyl-4-yl)-5-pyridin-4-ylmethyl-5H-imidazo[4,5-c]pyridine; 2-{3',4'-dimethyl-biphenyl-4-yl)-5-pyridin-2-ylmethyl-5H-imidazo

[4,5-c]pyridine; 2-{3',4'-dimethyl-biphenyl-4-yl)-5-[1-(toluene-4-sulfonyl)-1H-imidazol-2-ylmethyl]-5H-imidazo[4,5-c]pyridine; 2-(3',4'-dimethyl-biphenyl-4-yl)-5-[1-(toluene-4-sulfonyl)-1H-imidazol-4-ylmethyl]-5H-imidazo[4,5-c]pyridine; 2-(3',4'-dimethyl-biphenyl-4-yl)-5-(5-methyl-[1,3,4]oxadiazol-2-ylmethyl)-5H-imidazo[4,5-c]pyridine; 2-(3',4'-dimethyl-biphenyl-4-yl)-5-thiazol-2-ylmethyl-5H-imidazo[4,5-c]pyridine; 2-(3',4'-dimethyl-biphenyl-4-yl)-5-[2-(1H-imidazol-4-yl)-ethyl]-5H-imidazo[4,5-c]pyridine; 2-(3',4'-dimethyl-biphenyl-4-yl)-5-(3-methyl-3H-imidazol-4-ylmethyl)-5H-imidazo[4,5-c]pyridine; 2-(3',4'-dimethyl-biphenyl-4-yl)-5-(1-methyl-1H-imidazol-4-ylmethyl)-5H-imidazo[4,5c]pyridine; 2-[2-(3',4'-dimethyl-biphenyl-4-yl)-imidazo[4,5-c]pyridin-5-yl]-1-(2-methyl-1H-imidazol-4-yl)-ethanone; 2-[2-(3',4'-dimethyl-biphenyl-4-yl)-imidazo[4,5-c]pyridin-5-yl]-1-(2H-pyrazol-3-yl)-ethanone; 1-(2-Amino-4-methyl-thiazol-5-yl)-2-[2-(3',4'-dimethyl-biphenyl-4-yl)-imidazo[4,5-c]pyridin-5-yl]ethanone; 2-(3',4'-dimethyl-biphenyl-4-yl)-5-[2-(2H-pyrazol-3-yl)-ethyl]-5H-imidazo[4,5-c]pyridine; 2-[2-(4'-methoxy-biphenyl-4-yl)-imidazo[4,5-c]pyridin-5-yl]-1-(2H-pyrazol-3-yl)-ethanone hydrochloride; 2-{2-[4-(1-methyl-5-trifluoromethyl-1H-pyrazol-3-yl)-phenyl]imidazo[4,5-c]pyridin-5-yl}-1-(2H-pyrazol-3-yl)-ethanone maleate; 2-[2-(4'-fluoro-biphenyl-4-yl)-imidazo[4,5-c]pyridin-5-yl]-1-(2H-pyrazol-3-yl)-ethanone hydrochloride; 2-[2-{3'-methyl-biphenyl-4-yl)-imidazo[4,5~c]pyridin-5-yl]-1-{2H-pyrazol~3-yl)-ethanone; 2-[2-(3'-Chloro-biphenyl-4-yl)-imidazo[4,5-c]pyridin-5-yl]-1-(2H-pyrazol-3-yl)-ethanone hydrochloride; 2-(3',4'-dimethyl-biphenyl-4-yl)-5-(2H-pyrazol-3-ylmethyl)-5H-imidazo[4,5-c]pyridine hydrochloride; 2-(3'-chloro-biphenyl-4-yl)-5-(2H-pyrazol-3-ylmethyl)-5H-imidazo[4,5-c]pyridine hydrochloride; 2-(3'-methyl-biphenyl-4-yl)-5-{2H-pyrazol-3-ylmethyl)-5H-imidazo[4,5-c]pyridine hydrochloride; 2-[2-(3',4I-dimethyl-biphenyl-4-yl)-imidazo[4,5-c]pyridin-5-yl]-ethanol; '2-[2-{3',4'-dimethyl-biphenyl-4-yl)-imidazo[4,5-c]pyridin-5-yl]-ethylamine; 2-(3',4'-dimethyl-biphenyl-4-yl)-5-(1H-tetrazol-5-ylmethyl)-5H-imidazo[4,5-c]pyridine1-[2-(3',4'-dimethyl-biphenyl-4-yl)-imidazo[4,5-c]pyridin-5-yl]-propan-2-ol; 1-[2-(3',4'-dimethyl-biphenyl-4-yl)-imidazo[4,5-c]-propan-2-one O-methyl-oxime; 2-[2-(3',4'-dimethyl-biphenyl-4-yl)-imidazo[4,5-c]pyridin-5-yl]-N,N-dimethyl-acetamide; 2-[2-(3',4'-dimethyl-biphenyl-4-yl)-imidazo[4,5-c]pyridin-5-yl]-acetamide; 2-[2-(3',4'-dimethyl-biphenyl-4-yl)-imidazo[4,5-c]pyridin-5-yl]-N-methyl-acetamide; 5-[2-(3',4'-dimethyl-biphenyl-4-yl)-imidazo[4,5-c]pyridin-5-ylmethyl]-1,2-dihydro-pyrazol-3-one; 2-(3',4'-dimethyl-biphenyl-4-yl)-5-(1H-imidazol-2-ylmethyl)-5H-imidazo[4,5-c]pyridine; 2-(3',4'-dimethyl-biphenyl-4-yl)-5-(1H-imidazol-4-ylmethyl)-5H-imidazo[4,5-c]pyridine; 5-[2-(3',4'-dimethyl-biphenyl-4-yl)-imidazo[4,5-c]pyridin-5-ylmethyl]-2,4-dihydro-[1,2,4]triazol-3-one; 2-(3',4'-dimethyl-biphenyl-4-yl)-5-(1H-[1,2,4]triazol-3-ylmethyl)-5H-imidazo[4,5c]pyridine; 5-[2-(3',4'-dimethyl-biphenyl-4-yl)-imidazo[4,5-c]pyridin-5-ylmethyl]-3.H-[1,3,4]oxadiazol-2-one; 5-[2-(3',4'-dimethyl-biphenyl-4-yl)-imidazo[4,5-c]pyridin-5-ylmethy)-[1,3,4]oxadiazol-2-ylamine; 2-(3',4'-dimethyl-biphenyl-4-yl)-5-{2-methyl-1H-imidazol-4-ylmethyl)-5H-imidazo[4,5c]pyridine; 2-(3',4'-dimethyl-biphenyl-4-yl)-5-(1H-pyrazol-4-ylmethyl)-5H-imidazo[4,5-c]pyridine; 2-[2-(3',4'-dimethyl-biphenyl-4-yl)-imidazo[4,5-c]pyridin-5-yl]-1-{2-methyl-1-[2-(2-methyl-1H-imidazol-4-yl)-2-oxo-ethyl]-1H-imidazol-4-yl}-ethanone; 2-[2-(3',4'-dimethyl-biphenyl-4-yl)-imidazo[4,5-c]pyridin-5-yl]-1-(2-methyl-1H-imidazol-4-yl)-ethanol; 2-[2-(3',4'-dimethyl-biphenyl-4-yl)-imidazo[4,5-c]pyridin-5-yl]-1-(2H-pyrazol-3-yl)-ethanol; 2-[2-(3',4'-Dimethyl-biphenyl-4-yl)-imidazo[4,5-c]pyridin-5-yl]-1-pyrazin-2-yl-ethanol; 2-(4-bromo-phenyl)-3H-imidazo[4,5-c]pyridine; 2-[4-(1-methyl-5-trifluoromethyl-1H-pyrazol-3-yl)-phenyl]-3H-imidazo[4,5-c]pyridine hydrochloride; 2-(4'-methoxy-biphenyl-4-yl)-3H-imidazo[4,5-c3pyridine; 2-(4'-fluoro-biphenyl-4-yl)-3H-imidazo[4,5-c]pyridine; 2-{31-methyl-biphenyl-4-yl)-3H-imidazo[4,5-c]pyridine; and 2-(3'-chloro-biphenyl-4-yl)-3H-imidazo[4,5-c]pyridine.

Additional compounds falling within the scope of formula (I) are suitably selected from: 2-(3-Fluoro-3',4'-dimethyl-biphenyl-4-yl)-3H-imidazo[4,5-c]pyridine; 2-(2,5-Difluoro-3',4'-dimethyl-biphenyl-4-yl)-3H-imidazo[4,5-c]pyridine; 2-(3',4'-Dimethyl-biphenyl-4-yl)-6-trifluoromethyl-3H-imidazo[4,5-c]pyridine; 2-(3',4'-Dimethyl-biphenyl-4-yl)-6-methoxy-3H-imidazo[4,5-c]pyridine; 2-[2-(3',4'-Dimethyl-biphenyl-4-yl)-imidazo[4,5-c]pyridin-5-yl]-1-(2-methyl-2H-pyrazol-3-yl)-ethanone; 2-(3',4'-Dimethyl-biphenyl-4-yl)-5-[1,3,4]oxadiazol-2-ylmethyl-5H-imidazo[4,5-c]pyridine; {5-[2-(31,4-Dimethyl-biphenyl-4-yl)-imidazo[4,5-c]pyridin-5-ylmethyl]-[1,3,4]oxadiazol-2-yl}-dimethyl-amine; 2-[2-(3',4'-Dimethyl-biphenyl-4-yl)-imidazo[4,5-c]pyridin-5-yl]-1-oxazol-5-yl-ethanone; 2-[2-(3',4'-Dimethyl-biphenyl-4-yl)-imidazo[4,5-c]pyridin-5-yl]-1-[1,3,4]oxadiazol-2-yl-ethanone; 2-[2-{3',4'-Dimethyl-biphenyl-4-yl)-imidazo[4,5-c]pyridin-5-yl]-1-oxazol-2-yl-ethanone; 2-[2-{3',4'-Dimethyl-biphenyl-4-yl)-imidazo[4,5-c]pyridin-5-yl]-1-(4-methyl-oxazol-2-yl)-ethanone; 2-[2-(3',4'-Dimethyl-biphenyl-4-yl)-imidazo[4,5-c]2-(3-Fluoro-3',4'-dimethyl-biphenyl-4-yl)-5-(4-methyl-thiazol-2-ylmethyl)-5H-imidazo[4,5-c]pyridine; 2-(3',4'-Dimethyl-biphenyl-4-yl)-6-methoxy-5-prop-2-ynyl-5H-imidazo[4,5-c]pyridine; 2-(3',4'-Dimethyl-biphenyl-4-yl)-5-[3-(1H-imidazol-4-yl)-propyl]-5H-imidazo[4,5-c]pyridine; 2-[2-(4'-Methoxy-biphenyl-4-yl)-imidazo[4,5-c]pyridin-5-yl]-1-<2-methyl-1H-imidazol-4-yl)-ethanone; 2-(3',4'-Dimethyl-biphenyl-4-yl)-5-(2-hydroxy-ethyl)-5)H-imidazo[4,5-c]pyridine-6-carbonitrile; 2-[2-(3',4'-Dimethyl-biphenyl-4-yl)-6-methoxy-imidazo[4,5-c]pyridin-5-yl]-ethanol; 2-(3',4'-Dimethyl-biphenyl-4-yl)-5-(2-methoxy-ethyl)-5H-imidazo[4>5-c]pyridine; {2-[2-(3',4'-Dimethyl-biphenyl-4-yl)-imidazo[4,5-c]pyridin-5-yl]-ethyl}-dimethyl-amine; Dimethyl-biphenyl-4-yl)-imidazo[4,5-c]pyridin-5-yl]-ethyl}-N-methyl-acetamide; H-{2-[2-(3',4'-Dimethyl-biphenyl-4-yl)-imidazo[4,5-c]pyridin-5-yl]-ethyl}-acetamide; 1-{2-[2-(3',4'-Dimethyl-biphenyl-4-yl)-imidazo[4,5-c]pyridin-5-yl]-ethyl}-pyrrolidin-2-one; 1-{2-[2-(3',4'-Dimethyl-biphenyl-4-yl)-imidazo[4,5-c]pyridin-5-yl]-ethyl}-1,3-di-hydro-imidazol-2-one; 1-{2-[2-(3',4'-Dimethyl-biphenyl-4-yl)-imidazo[4,5-c]pyridin-5-yl]-ethyl}-imidazolidin-2-one; 1-{2-[2-(3',4'-Dimethyl-biphenyl-4-yl)-imidazo[4,5-c]pyridin-5-yl)]-ethyl)}-3-methyl-imidazolidin-2-one; 1-{2-[2-(3',4'-Dimethyl-biphenyl-4-yl)-imidazo[4,5-c]pyridin-5-yl]-ethyl}-3-methyl-1,3-dihydro-imidazol-2-one; 2-(3',4'-Dimethyl-biphenyl-4-yl)-5-(2-methyl-2H-tetrazol-5-ylmethyl)-5H-imidazo[4,5-c]pyridine; 2-[2-(3',4'-Dinnethyl-biphenyl-4-yl)-imidazo[4,5-c]pyridin-5-yl]-1-(1,2-dimethyl-1H-imidaxo!-4-yl)-ethanone; 2-(3',4'-Dimethyl-biphenyl-4-yl)-5-(2-methyl-2H-pyrazol-3-ylmethyl)-5H-imidazo[4,5-c]pyridine; 1-{5-[2-(3',4'-Dimethyl-biphenyl-4-yl)-imidazo[4,5-c]pyridin-5-ylmethyl]-pyrazol-1-yl}-ethanone; 1-(1-Acetyl-2-methyl-1H-imidazol-4-yl)-2-[2-(3',4'-dimethyl-biphenyl-4-yl)-imidazo[4,5-c]pyridin-5-yl]-ethanone; 2-(3',4'-Dimethyl-biphenyl-4-yl)-5-pyrimidin-2-ylmethyl-5H-imidazo(4,5-c]pyridine; 6-[2-(3',4'-Dimethyl-biphenyl-4-yl)-imidazo[4,5-c]pyridin-5-ylmethyl]-pyridin-2-ol; 2-(3',4'-Dimethyl-biphenyl-4-yl)-5-pyridazin-3- ylmethyl-5H-imidazo[4,5-c]pyridine; 2-(3I,4'-Dimethyl-biphenyl-4-yl)-5-pyrimidin-5-ylmethyl-5H-imidazo[4,5-c]pyridine; 2-(3',4'-Dimethyl-biphenyl-4-yl)-5-pyrazin-2-ylmethyl-5H-imidazo[4,5-c]pyridine; 2-(3',4'-Dimethyl-biphenyl-4-yl)-5-pyrimidin-4-ylmethyl-5H-imidazo[4,5-c]pyridine; 2-[2-(3',4'-Dimethyl-biphenyl-4-yl)-imidazot4,5-c]pyridin-5-yl3-1-pyridin-4-yl-ethanone; 2-[2-(3',4'-Dimethyl-biphenyl-4-yl)-imidazo[4,5-c]pyridin-5-yl]-1-pyridin-3-yl-ethanone; 2-[2-(3',4'-Dimethyl-biphenyl-4-yl)-imidazot4,5-c]pyridin-5-yl]-1-pyridin-2-yl-ethanone; 2-[2-(3',4'-Dimethyl-biphenyl-4-yl)-imidazo{4,5-c]pyridin-5-yl]-1-pyrimidin-4-yl-ethanone; 2-{2-(3',4'-Dimethyl-biphenyl-4-yl)-imidazo[4,5-c]pyridin-5-yl]-1-pyridazin-3-yl-ethanone; 2-[2-(3',4'-Dimethyl-biphenyl-4-yl)-imidazo[4,5-c]pyridin-5-yl]-1-pyrimidin-2-yl-ethanone; 5-Benzo[d]isoxazol-3-ylmethyl-2-(3',4'-dimeihyl-biphenyl-4-yl)-5H-imidazo[4,5-c]pyridine 5-Benzooxazol-2-ylmethyl-2-(3\4'-dimethyl-biphenyl-4-yl)-5H-imidazo[4,5-c]pyridine; 5-(1H-Benzoimidazol-2-ylmethyl)-2-(3',4'-dimethyl-biphenyl-4-yl)-5H-imidazo[4,5-c]pyridine; 2-(3',4'-Dimethyl-biphenyl-4-yl)-5-(1-methyl-1H-benzoimidazol-2-ylmethyl)-5H-imidazo[4,5-c]pyridine; 2-(3',4'-Dimethyl-biphenyl-4-yl)-5-(1H-indol-2-ylmethyl)-5H-imidazo[4,5-c]pyridine; 2-(3',4'-Dimethyl-biphenyl-4-yl)-5-(1-methyl-1H-indol-2-ylmethyl)-5H-imidazo[4,5-c]pyridine; 2-(3',4'-Dimethyl-biphenyl-4-yl)-5-(1H-indol-3-ylmethyl)-5H-imidazo[4,5-c]pyridine; 2-(3',4'-Dimethyl-biphenyl-4-yl)-5-(1-methyl-1H-indol-3-ylmethyl)-5H-imidazo[4,5-c]pyridine.

In other embodiments, small molecule C3aR antagonists are selected from aryl imidazo[4,5-c] pyridine compounds as disclosed for example by Claffey et al. in WO 2007/034278, which is expressly incorporated herein by reference in its entirety. In representative examples, these compounds are represented by formula (II):

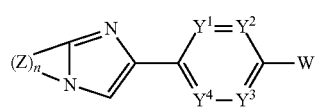

(II)

wherein:
W is selected from the group consisting of:

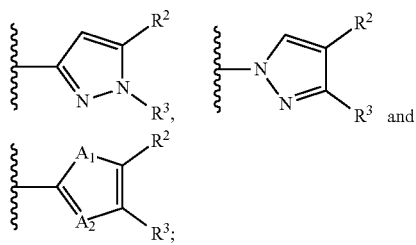

$A_1$ is O or S;
A2 is N or CH, with the proviso that if $A_1$ is O, $A_2$ is N;
n is between 3 and 5;
Z at each occurrence is independently selected from $CR^1$, $CHR^1$, C=O, N, $NR^1$, N=O,
S, and O, wherein a bond between two groups Z bonded to each other may be a single bond or a double bond;
the ring containing Z is a 5, 6, or 7-membered heterocyclic or heteroaryl ring containing 1-3 heteroatoms independently selected from the group consisting of O, N and S;

R' at each occurrence is independently selected from H, optionally substituted $C_1$-$C_8$ alkyl, optionally substituted $C_1$-$C_6$ alkoxy, halo, $SO_2N(R_6)_2$, $N(R_6)SO_2N(R_6)_2$, $SO_2R_8$, $CONHSO_2R_6$, $CONHSO_2(NR_6)_2$, optionally substituted 3-10-membered heterocycloalkyl, optionally substituted $C_3$-$C_{10}$ cycloalkyl, cyano, optionally substituted 5-10-membered heteroaryl, CORE, $CO_2R^6$, $N(R^6)_2$, $NR^6COR^6$, CON$(R^6)_2$, and $CONCO(R^e)_2$;
$R^6$ at each occurrence is independently selected from H, optionally substituted $C_1$-$C_5$ alkyl, optionally substituted 5-10 membered heteroaryl, optionally substituted $C_6$-$C_{10}$ aryl, optionally substituted $C_3$-$C_{10}$ cycloalkyl, and optionally substituted 3-10 membered heterocycloalkyl;
$R^2$ and $R^3$ are selected independently from H, optionally substituted $C_1$-$C_6$alkyl, halo, optionally substituted $C_1$-$C_6$alkenyl, optionally substituted $C_3$-$C_{10}$ cycloalkyl, trifluoromethyl, CO— optionally substituted $C_1$-$C_6$ alkyl, $CO_2$. optionally substituted $C_1$-$C_6$ alkyl, optionally substituted $C_1$-$C_6$alkoxy, and optionally substituted $C_1$-$C_6$alkylthio;
$Y^1$, $Y^2$, $Y^3$, $Y^4$ are independently selected from CH, CF, or N where no more than 2 N are in the ring;
or a pharmaceutically acceptable salt thereof.

Representative compounds according to formula II are suitably selected from: 2-[4-(1-Methyl-5-trifluoromethyl]-1H-pyrazol-3-yl)-phenyl]-imidazo[1,2-a]pyridine hydrochloride salt; 2-[4-(1-Methyl-5-trifluoromethyl-1H-pyrazol-3-yl)-phenyl]-5,6,7,8-tetrahydro-imidazo[1,2-a]pyridine p-toluenesulfonic acid; 2-[4-(1-Ethyl-5-trifluoromethyl-1H-pyrazol-3-yl)-phenyl]-imidazo[1,2-a]pyridine p-toluenesulfonic acid salt; 2-[4-(1-Ethyl-5-trifluoromethyl-1H-pyrazol-3-yl)-phenyl]-5,6,7,8-tetrahydro-imidazo[1,2-a]pyridine p-toluenesulfonic acid salt; 5-(4-Imidazo[1,2-a]pyridin-2-yl-phenyl)-2-methyl-2H-pyrazole-3-carboxylic acid methyl ester; 2-[4-(1-Metriyl-5-trifluoromethyl-1H-pyrazol-3-yl)-phenyl]-imidazo[1,2-a]pyridine-6-carboxylic acid ethyl ester; {2-[4-(1-Methyl-5-trifluoromethyl-1H-pyrazol-3-yl)-phenyl]-imidazo[1,2-a]pyridin-6-yl}-methanol; {2-[4-(1-Methyl-5-trifluoromethyl-1H-pyrazol-3-yl)-phenyl]-5,6,7,8-tetrahydro-imidazo[1,2-a]pyridin-6-yl}-methanol; 6-Chloro-2-[4-(1-methyl-5-trifluoromethyl-1H-pyrazol-3-yl)-phenyl]-imidazo[1,2-b]pyridazine; 2-[4-(1-Methyl-5-trifluoromethyl-1H-pyrazol-3-y))-phenyl]-imidazo[1,2-b]pyridazin-6-ylamine p-toluene sulfonic acid salt; 2-[4-(1-Methyl-5-trifluoromethyl-1H-pyrazol-3-y))-phenyl]-imidazo[1,2-b]pyridazine p-toluene sulfonic acid salt; 2-[4-(1-Methyl-5-trifluoromethyl-1H-pyrazol-3-yl)-phenyl]-5,6,7,8-tetrahydro-imidazo[1,2-b]pyridazine p-toluenesulfonic acid salt; 2-[4-(1-Methyl-5-trifluoromethyl-1H-pyrazol-3-y))-phenyl]-imidazo[1,2-a]pyridine-6-carbaldehyde; 1-{2-[4-(1-Methyl-5-trifluoromethyl-1H-pyrazol-3-yl)-phenyl]-imidazo[1,2-a]pyridin-6-yl}-ethanol; 1-{2-[4-(1-Methyl-5-trifluoromethyl-1H-pyrazol-3-yl)-phenyl]-5,6,7,8-tetrahydro-imidazo[1,2-a]pyridin-6-yl}-ethanol; {2-[4-(1-Methyl-5-trifluoromethyl-1H-pyrazol-3-yl)-phenyl]-imidazo[1,2-a]pyridin-7-yl}-methanol p-toluene sulfonic acid salt; 1-{2-[4-(1-Methyl-5-trifluoromethyl-1H-pyrazol-3-yl)-phenyl]-imidazo[1,2-a]pyridin-7-yl}-ethanol; {2-[4-(1-Methyl-5-trifluoromethyl-1H-pyrazol-3-yl)-phenyl]-5,6,7,8-tetrahydro-imidazo[1,2-a]pyridin-7-yl}-methanol; 6-[4-(1-Methyl-5-trifluoromethyl-1H-pyrazol-3-yl)-phenyl]-2,3-dihydro-imidazo[2,1-b]thiazole; 2-[4-(1-Methyl-5-trifluoromethyl-1H-pyrazol-3-yl)-phenyl]-imidazo[1,2-a]pyridine-6-carbonitrile; 2-(4-(1-Methyl-5-trifluoromethyl-1H-pyrazol-3-yl)-phenyl]-6-{1H-tetrazo)-5-yl)-imidazo[1,2-a]pyridine; 3-{2-[4-(1-Methyl-5-trifluoromethyl-1H-pyrazol-3-yl)-phenyl]-imidazo[1,2-a]pyridin-6-yl}-[1,2,4]

oxadiazol-5-ol; 2-[4-(1-Methyl-5-trifluoromethyl-1H-pyrazol-3-yl)-phenyl]-imidazo[1,2-b]pyridazine-6-carbonitrile; 2-[4-(1-Methyl-5-trifluoromethyl-1H-pyrazol-3-yl)-phenyl]-6-(1H-tetrazoi-5-yl)-imidazo[1,2-b]pyridazine; N-{2-[4-(1-Methyl-5-trifluoromethyl-1H-pyrazol-3-yl)-phenyl]-imidazo[1,2-a]pyridazine-6-yl}-acetamide p-toluenesulfonic acid salt; 2-[4-(1-Methyl-5-trifluoromethyl-1H-pyrazol-3-yl)-phenyl]-imidazo[1,2-a]pyridin-6-ylamine bis-p-toluenesulfonic acid salt; 6-(2,5-Dimethyl-pyrrol-1-yl)-2-[4-(1-methyl-5-trifluoromethyl-1H-pyrazol-3-yl)-phenyl]-imidazo[1,2-a]pyridine; 2-[4-(1-Methyl-5-trifluoramethyl-1H-pyrazol-3-yl)-phenyl]-5,6,7,8-tetrahydro-imidazo[1,2-a]pyridin-6-ylamine bis-p-toluenesulfonic acid salt; N-{2-[4-(1-Methyl-5-trifluoromethyl-1H-pyrazol-3-yl)-phenyl]-5,6,7,8-tetrahydro-imidazo[1,2-a]pyridin-6-yl}-acetamide p-toluenesulfanic acid salt; C-[2-[4-(1-Methyl-5-trifluoromethyl-1H-pyrazol-3-yl)-phenyl]-5,6,7,8-tetrahydro-imidazo[1,2-a]pyridin-6-yl}-methylamine bis-hydrochloride salt; Cyclopropanecarboxylic acid {2-(4-(1-methyl-5-trifluoromethyl-1H-pyrazol-3-yl)-phenyl]-5,6,7,8-tetrahydro-imidazo[1,2-a]pyridin-6-ylmethyl}-amide p-toluenesulfonic acid salt; 1H-Pyrrole-2-carboxylic acid {2-[4-(1-methyl-5-trifluoromethyl-1H-pyrazol-3-yl)-phenyl]-5,6,7,8-tetrahydro-imidazo[1,2-a]pyridin-6-ylmethyl}-amide bis-p-toluenesulfonic acid salt; N-{2-[4-(1-Methyl-5-trifluoromethyl-1H-pyrazol-3-yl)-phenyl]-5,6,7,8-tetrahydro-imidazo[1,2-a]pyridin-6-ylmethyl)-nicotinamide bis-p-toluenesulfonic acid salt; 2-(1,1-Dioxo-tetrahydro-116-thiophen-3-yl)-N-{2-[4-(1-methyl-5-trifluoromethyl-1H-pyrazol-3-yl)-phenyl]-5,6,7,8-tetrahydro-imidazo[1,2-a]pyridin-6-ylmethyl}-acetamide p-toluenesulfonic acid salt; 3-Methyl-5-[4-(1-methyl-5-trifluoromethyl-1H-pyrazol-3-yl)-phenyl]-3H-imidazo[1,2-b][1,2,4]triazole-2-carbaldehyde; {3-Methyl-5-[4-(1-methyl-5-trifluoromethyl-1H-pyrazol-3-yl)-phenyl]-3H-imidazo[1,2-b][1,2,4]triazol-2-yl}-methanol p-toluenesulfonic acid salt; 1-Methyl-6-[4-(1-methyl-5-trifluoromethyl-1H-pyrazol-3-yl)-phenyl]-1H-imidazo[1,2-a]imidazole p-toluenesulfonic acid salt; {1-Methyl-6-[4-(1-methyl-5-trifluoromethyl-1H-pyrazol-3-yl)-phenyl]-1H-imidazo[1,2-a]imidazol-2-yl}-methanol p-toluenesulfonic acid salt; 2-[4-(4-Ethyl-thiophen-2-yl)-phenyl]-5,6,7,8-tetrahydro-imidazo[1,2-a]pyridine hydrochloride; 2-[4-(5-Ethyl-thiophen-2-yl)-phenyl]-5,6,7,8-tetrahydro-imidazo[1,2-a]pyridine hydrochloride; 2-[4-(5-Methyl-thiophen-2-yl)-phenyl]-5,6,7,8-tetrahydro-imidazo[1,2-a]pyridine hydrochloride; 2-(4-(5-(Trifluoromethyl)-4-methyloxazol-2-yl)phenyl)H-imidazo[1,2-a]pyridine; and 2-(4-(3-(Trifluoromethyl)-4-methyl-1H-pyrazol-1-yl)phenyl)-5,6,7,8-tetrahydroimidazo[1,2-a]pyridine.

In still other embodiments, small molecule C3aR antagonists are selected from biphenylimidazole compounds as disclosed for example by Claffey et al. in WO 2007/034282, which is expressly incorporated herein by reference in its entirety. In representative examples, these biphenylimidazole compounds are represented by formula (III):

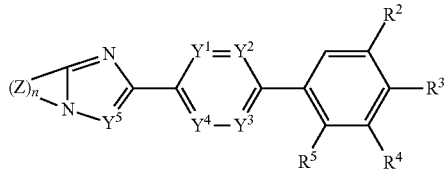

(III)

wherein:

n is between 3 and 5;

Z at each occurrence is independently selected from $CR^1$, $CHR^1$, C=O, N, $NR^1$, N=O, S, and O, wherein a bond between two groups Z bonded to each other may be a single bond or a double bond;

the ring containing Z is a 5, 6, or 7-membered heterocyclic or heteroaryl ring containing 1-3 heteroatoms independently selected from the group consisting of O, N and S;

$R^1$ at each occurrence is independently selected from H, optionally substituted $C_1$-$C_8$ alkyl, optionally substituted $C_1$-$C_6$ alkoxy, halo, $SO_2N(Re)_2$, $N<R_6)SO_2N(R_6)_2$, $SO_2R_6$, $CONHSO_2R_6$, $CONHSO_2(NR_6)_2$, optionally substituted 3-10-membered heterocycloalkyl, optionally substituted $C_3$-$C_{10}$ cycloalkyl, cyano, optionally substituted 5-10-membered heteroaryl, optionally substituted $C_6$-$C_{10}$ aryl, CORE, $CO_2R^6$, $N(R^6)_2$, $NR^6COR^6$, $CON(R^6J2$, and $CONCO(R^6J2$;

$R^6$ at each occurrence is independently selected from H, optionally substituted $C_1$-$C_6$ alkyl, optionally substituted 5-10 membered heteroaryl, optionally substituted $C_6$-$C_{10}$ aryl, optionally substituted $C_3$-$C_{10}$ cycloalkyl, and optionally substituted 3-10 membered heterocycloalkyl;

$R^2$, $R^3$ and $R^4$ are selected independently from H, optionally substituted $CrC_6$alkyl, halo, optionally substituted $C_1$-$C_6$ alkenyl, optionally substituted $C_3$-$C_{10}$ cycloalkyl, trifluoromethyl, CO— optionally substituted $C_1$-$C_6$ alkyl, $CO_2$— optionally substituted $C_1$-$C_6$ alkyl, optionally substituted $C_1$-$C_6$BIkOXy, and optionally substituted $C_1$-$C_6$ alkylthio.

Exemplary compounds according to formula III are suitably selected from: 6-(3',4'-Dimethyl-biphenyl-4-yl)-1-methyl-2,3-dihydro-1H-imidazo[1,2-a]imidazole hydrobromide; 6-(3',4'-Dimethyl-biphenyl-4-yl)-1-methyl-1H-imidazo[1,2-a]imidazole hydrobromide; 6-(3',4'-Dimethyl-biphenyl-4-yl)-2-methyl-imidazo{2,1-b][1,3,4]thiadiazole; 6-Biphenyl-4-yl-1-methyl-1H-imidazo[1,2-a]imidazole hydrochloride; 5-(3-Fluoro-3',4'-dimethyl-biphenyl-4-yl)-3-methyl-3H-imidazo[1,2-b][1,2,4]triazole; 6-(3-Fluoro-3',4'-dimethyl-biphenyl-4-yl)-1-methyl-1H-imidazo[1,2-a]imidazole; 5-(3-Fluoro-3',4'-dimethyl-biphenyl-4-yl)-2)3-dimethyl-3H-imidazo[1,2-b][1,2,4]triazole; 6-(3-Fluoro-3',4'-dimethyl-biphenyl-4-yl)-1-methyl-1H-imidazo[2,1-c][1,2,4]triazole; 2-(3-Fluoro-3',4'-dimethyl-biphenyl-4-yl)-5,6,7,8-tetrahydro-imidazo[1,2-a]pyridine hydrochloride; 2-(2-Fluoro-3',4'-dimethyl-biphenyl-4-yl)-5,6,7,8-tetrahydro-imidazo[1,2-a]pyridine hydrochloride; 6-(3',4'-Dimethyl-biphenyl-4-yl)-imidazo[2,1-b]thiazole; 6-(3',4'-Dimethyl-biphenyl-4-yl)-imidazo[2,1-b][1,3,4]thiadiazole; 6-(3',4'-Dimethyl-biphenyl-4-yl)-3-methyl-imidazo[5,1-b]oxazole; 2-[6-(3',4'-Dimethyl-biphenyl-4-yl)-imidazo[1,2-a]imidazol-1-yl]-ethanol; 2-(3',4'-Dimethyl-biphenyl-4-yl)-6-methoxy-imidazo[1,2-b]pyridazine hydrobromide; 6-Chloro-2-(3',4'-dimethyl-biphenyl-4-yl)-imidazo[1,2-b]pyridazine; 2-(3-Fluoro-3',4'-dimethyl-biphenyl-4-yl)-imidazo[1,2-b]pyridazin-6-ylamine; 2-(3',4'-Dimethyl-biphenyl-4-yl)-8-fluoro-6H-imidazo[1,2-c]pyrimidin-5-one; 6-(3',4'-Dirhethyl-biphenyl-4-yl)-imidazo[1,2-b][1,2,4]triazine; 2-(3',4'-Dimethyl-biphenyl-4-yl)-6-methyl-7,8-dihydro-6H-imidazo[1,2-c]pyrimidin-5-one; 2-[2-(3',4'-Dimethyl-biphenyl-4-yl)-imidazo[1,2-b]pyridazin-7-yl]-propan-2-ol; 2-(3',4'-Dimethyl-biphenyl-4-yl)-imidazo[1,2-a]pyrimidin-7-ylamine; 2-(3',4'-Dimethyl-biphenyl-4-yl)-imidazo[1,2-a]pyridine-6-sulfonic acid amide; 2-[2-(3',4'-Dimethyl-biphenyl-4-yl)-imidazo[1,2-b]pyridazin-6-yl]-propan-2-ol; 2-(3',4'-Dimethyl-biphenyl-4-yl)-imidazo[1,2-b]pyridazine; 1-[2-(3',4'-Dimethyl-biphenyl-4-yl)-imidazo[1,2-b]pyridazin-7-yl]-ethanol; 2-(3',4'-Dimethyl-biphenyl- 4-yl)-imidazo[1,2-c]pyrimidin-7-ylamine; 2-(4'-Isopropyl-3'-methyl-biphenyl-4-yl)-5,6,7,8-tetrahydro-imidazo[1,2-a]pyridine hydrochloride; 2-(4'-Butyl-biphenyl-4-yl)-5,6,7,8-tetrahydro-imidazo[1,2-a]pyridine hydrochloride; 2-(3',4'-Dimethyl-biphenyl-4-yl)-5,6,7,8-tetrahydro-imidazo[1,2-a]pyridine hydrochloride; 2-(3'-Chloro-4'-methyl-biphenyl-4-yl)-5,6,7,8-tetrahydro-imidazo[1,2-a]pyridine hydrochloride; 2-(4'-Fluoro-3'-methyl-biphenyl-4-yl)-5,6,7,8-tetrahydro-imidazo[1,2-a]pyridine hydrochloride; 2-(4'-Vinyl-biphenyl-4-yl)-5,6,7,8-tetrahydro-imidazo[1,2-a]pyridine hydrochloride; 2-(4'-Trifluoromethyl-biphenyl-4-yl)-5,6,7,8-tetrahydro-imidazo[1,2-a]pyridine hydrochloride; 2-(4'-Methyl-biphenyl-4-yl)-5,6,7,8-tetrahydro-imidazo[1,2-a]pyridine hydrochloride; 2-(4'-Cyclopropyl-biphenyl-4-yl)-5,6,7,8-tetrahydro-imidazo[1,2-a]pyridine hydrochloride; 2-(4'-Ethyl-biphenyl-4-yl)-5,6,7,8-tetrahydro-imidazo[1,2-a]pyridine hydrochloride; 2-(4'-Isopropyl-biphenyl-4-yl)-5,6,7,8-tetrahydro-imidazo[1,2-a]pyridine hydrochloride; 2-(4'-Propyl-biphenyl-4-yl)-5,6,7,8-tetrahydro-imidazo[1,2-a]pyridine hydrochloride; 2-(4'-Methoxymethyl-biphenyl-4-yl)-5,6,7,8-tetrahydro-imidazo[1,2-a]pyridine hydrochloride; 2-(4'-Methylsulfanylmethyl-biphenyl-4-yl)-5,6,7,8-tetrahydro-imidazo[1,2-a]pyridine hydrochloride; 2-(4'-tert-Butyl-biphenyl-4-yl)-5,6,7,8-tetrahydro-imidazo[1,2-a]pyridine hydrochloride; 2-(2'-Fluoro-4',5'-dimethyl-biphenyl-4-yl)-5,6,7,8-tetrahydro-imidazo[1,2-a]pyridine hydrochloride; 2-(2'-Fluoro-4'-isopropyl-biphenyl-4-yl)-5,6,7,8-tetrahydro-imidazo[1,2-a]pyridine hydrochloride; 2-(3'-Ethyl-biphenyl-4-yl)-5,6,7,8-tetrahydro-imidazoj;i,2-a]pyridine hydrochloride; 2-(4-Indan-5-yl-phenyl)-5,6,7,8-tetrahydro-imidazo[1,2-a]pyridine; 2-(4-Benzo[1,3]dioxol-5-yl-phenyl)-5,6,7,8-tetrahydro-imidazo[1,2-a]pyridine hydrochloride; 2-(4'-Chloro-3'-methyl-biphenyl-4-yl)-5,6,7,8-tetrahydro-imidazo[1,2-a]pyridine hydrochloride; 2-(5'-Fluoro-3',4'-dimethyl-biphenyl-4-yl)-5,6,7,8-tetrahydro-imidazo[1,2-a]pyridine hydrochloride; 2-(3'-Methyl-biphenyl-4-yl)-5,6,7,8-tetrahydro-imidazo[1,2-a]pyridine hydrochloride 5-(3',4'-Dimethyl-biphenyl-4-yl)-2,3-dimethyl-3H-imidazo[1,2-b][1,2,4]triazole; 5-(3',4'-Dimethyl-biphenyl-4-yl)-3-methyl-3H-imidazo[1,2-b][1,2,4]triazole; 2-(3-Fluoro-3',4'-dimethyl-biphenyl-4-yl)-5,6,7,8-tetrahydro-[1,2,4]triazolo[1,5-a]pyridine; 6-(3',4'-Dimethyl-biphenyl-4-yl)-1-methyl-1H-imidazo[2,1-c][1,2,4]triazole; 2-(2'-Fluoro-4'-methyl-biphenyl-4-yl)-5,6,7,8-tetrahydro-imidazo[1,2-a]pyridine hydrochloride; 2-(3'-Methyl-4'-trifluoromethyl-biphenyl-4-yl)-5,6,7,8-tetrahydro-imidazo[1,2-a]pyridine; 2-(4'-Methyl-3'-trifluoromethyl-biphenyl-4-yl)-5,6,7,8-tetrahydro-imidazo[1,2-a]pyridine; 2-(3',4'-Bis-trifluoromethyl-biphenyl-4-yl)-5,6,7,8-tetrahydro-imidazo[1,2-a]pyridine; 2-(3'-Fluoro-4'-methyl-biphenyl-4-yl)-5,6,7,8-tetrahydro-imidazo[1,2-a]pyridine hydrochloride; 2-(3',4'-Dimethyl-biphenyl-4-yl)-5,6,7,8-tetrahydro-[1,2,4]triazolo[1,5-a]pyridine; 2-(3',4'-Dimethyl-biphenyl-4-yl)-imidazo[1,2-a]pyridine-6-carboxylic acid, lithium salt; N-[2-(3',4'-Dimethyl-biphenyl-4-yl)-imidazo[1,2-a]pyridine-6-carbonyl]-methanesulfonamide; N-[2-(3',4'-Dimethyl-biphenyl-4-yl)-imidazo[1,2-a]pyridine-6-carbonyl]-dimethylsulfonimide; N-[2-(3',4'-Dimethyl-biphenyl-4-yl)-imidazo[1,2-a]pyridine-6-carbonyl]-sulfonimide; 2-[2-(3',4'-Dimethyl-biphenyl-4-yl)-imidazo[1,2-a]pyridin-6-yl]-prop'an-2-ol; 2-(3',4'-Dimethyl-biphenyl-4-yl)-imidazo[1,2-a]pyridine-6-ylamine; 6-(3',4'-Dimethyl-biphenyl-4-yl)-1-ethyl-1H-imidazo[1,2-a]imidazole; 2-Biphenyl-4-yl-6-morpholin-4-yl-imidazo[1,2-a]pyridine; (2-Biphenyl-4-yl-imidazo[1,2-a]pyridin-6-yl)-(2-methoxy-ethyl)-amine; (2-Biphenyl-4-yl-imidazo[1,2-a]pyridin-6-yl)-(2,2-dimethoxy-ethyl)-methyl-amine; 6-Aziridin-1-yl-2-biphenyl-4-yl-imidazo[1,2-a]pyridine; 2-Biphenyl-4-yl-7-morpholin-4-yl-imidazo[1,2-a]pyridine; 2-Biphenyl-4-yl-6-bromo-imidazo[1,2-a]pyridine; 6-Bromo-2-(3',4'-dimethyl-biphenyl-4-yl)-imidazo[1,2-a]pyridine; 2-Biphenyl-4-yl-imidazo[1,2-a]pyridine-6-carbonitrile; 2-(3',4'-Dimethyl-biphenyl-4-yl)-imidazo[1,2-a]pyridine-6-carbonitrile; 2-Biphenyl-4-yl-6-(1H-tetrazol-5-yl)-imidazot1,2-a]pyridine; 2-(3',4'-Dimethyl-biphenyl-4-yl)-6-(1H-tetrazoi-5-yl)-imidazo[1,2-a]pyridine; 2-[4-(2,3-Dihydro-benzo[1,4]dioxin-6-yl)-phenyl]-imidazo[1,2-a]pyridine; 2-(3-Fluoro-3',4'-dimethyl-biphenyl-4-yl)-imidazo[1,2-a]pyridine; ' 2-(4-Isochroman-7-yl-phenyl)-imidazo[1,2-a]pyridine; 3-Ethyl-6-(4-imidazo[1,2-a]pyridin-2-yl-phenyl)-1-methyl-1H-indazole; 2-(3',4'-Dimethyl-biphenyl-4-yl)-imidazo[1,2-a]pyridine; 3-[2-(3',4'-Dimethyl-biphenyl-4-yl)-imidazo[1,2-a]pyridin-6-yl]-[1,2,4]oxadiazol-5-ol; 2-Biphenyl-4-yl-7-(1H-tetrazol-5-yl)-imidazo[1,2-a]pyridine; 6-(3',4'-Dimethyl-biphenyl-4-yl)-2,3-dihydro-imidazo{2,1-b]thiazole tosylate salt; 2-[6-(3',4'-Dimethyl-biphenyl-4-yl)-imidazo[2,1-b]thiazol-3-yl]-ethanol tosylate salt; 2-Biphenyl-4-yl-7-ethyl-imidazo[1,2-a]pyridine; (2-Biphenyl-4-yl-imidazo[1,2-a]pyridin-7-yl)-methanol; 2-Biphenyl-4-yl-7-methoxymethyl-imidazo[1,2-a]pyridine; [2-(3',4'-Dimethyl-biphenyl-4-yl)-imidazo[1,2-a]pyridin-6-yl]-methanol; [2-(3',4'-Dimethyl-biphenyl-4-yl)-imidazo[1,2-a]pyridin-7-yl]-methanol; [2-(3',4'-Dimethyl-biphenyl-4-yl)-5,6,7,8-tetrahydro-imidazo[1,2-a]pyridin-7-yl]-methanol; [2-(3',4'-Dimethyl-biphenyl-4-yl)-5,6,7,8-tetrahydro-imidazo[1,2-a]pyridin-6-yl]-methanol; 2-(3',4'-Dimethyl-biphenyl-4-yl)-imidazo[1,2-a]pyridine-6-carboxylic acid amide; C-[2-(3',4'-Dimethyl-biphenyl-4-yl)-5>6,7,8-tetrahydro-imidazot1,2-a]pyridin-6-yl]-methylamine; N-[2-(3',4'-Dimethyl-biphenyl-4-yl)-5,6,7,8-tetrahydro-imidazo[1,2-a]pyridin-6-ylmethyl]-acetamide; N-[2-(3',4'-Djmethyl-biphenyl-4-yl)-5,6,7,8-tetrahydro-imidazo[1,2-a]pyridin-6-ylmethyl]-2-phenyl-acetamide; Benzo[b]thiophene-2-carboxylic acid [2'-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2-a]pyridin-6-ylmethyl]-propionamide; N-[2-(3',4ʹ-Dimethyl-biphenyl-4-yl)-5,6,7,8-tetrahydro-imidazo[1,2-a]pyridin-6-ylmethyl]-3-fluoro-benzamide; N-[2-(3',4'-Dimethyl-biphenyl-4-yl)-5,6,7,8-tetrahydro-imidazo[1,2-a]pyridin-6-ylmethyl]-4-fluoro-benzamide; N-[2-(3',4'-Dimethyl-biphenyl-4-yl)-5,6,7,8-tetrahydro-imidazo[1,2-a]pyridin-6-ylmethyl]-2-fluoro-benzamide; Hexanoic acid [2-(3',4'-dimethyl-biphenyl-4-yl)-5,6,7,8-tetrahydro-imidazo[1,2-a]pyridin-6-ylmethyl]-amide; 1H-Indole-4-carboxylic acid [2-(3',4'-dimethyl-biphenyl-4-yl)-5,6,7,8-tetrahydro-imidazo[1,2-a]pyridin-6-ylmethyl]-amide; 1-Methyl-1H-pyrrole-2-carboxylic acid [2-(3',4'-dimethyl-biphenyl-4-yl)-5,6,7,δ-tetrahydro-imidazo[1,2-a]pyridin-6-ylmethyl]-amide; 2,5-Dimethyl-1H-pyrrole-3-carboxylic acid [2-(3',4'-dimethyl-biphenyl-4-yl)-5,6,7,δ-tetrahydro-imidazo[1,2-a]pyridin-6-ylmethyl]-amide; 3-Oxo-indan-1-carboxylic acid [2-(3',4'-dimethyl-biphenyl-4-yl)-5,6,7,δ-tetrahydro-imidazo[1,2-a]pyridin-6-ylmethyl]-amide; 1H-Indole-3-carboxylic acid [2-(3',4'-dimethyl-biphenyl-4-yl)-5,6,7,3-tetrahydro-imidazo[1,2-a]pyridin-6-ylmethyl]-amide; (R)-Chroman-2-carboxylic acid [2-(3',4'-dimethyl-biphenyl-4-yl)-5,6,7,8-tetrahydro-imidazo[1,2-a]pyridin-6-ylmethyl]-amide; 1H-Indole-5-carboxylic acid t2-(3',4'-dimethyl-biphenyl-4-yl)-5,6,7,8-tetrahydro-imidazo[1,2-a]pyridin-6-ylmethyl]-amide; Cycloheptanecarboxylic acid [2-(3',4'-dimethyl-biphenyl-4-yl)-5,6,7,8-tetrahydro-imidazo[1,2-a]pyridin-6-ylmethyl]-amide; 1H-Benzotriazole-5-carboxylic acid [2-(3',4'-dimethyl-biphenyl-4-yl)-5,6,7,8-tetrahydro-imidazol[1,2-a]pyridin-6-ylmethyll-amide; Cyclopentanecarboxylic acid [2-(3',4'-dimethyl-biphenyl-4-yl)-5,6,7,8-tetrahydro-imidazo[1,2-a]pyridin-6-ylmethyl]-amide; Bicyclo[4.2.0]octa-1 (6),2,4-triene-7-carboxylic acid {2-(3',4'-dimethyl-biphenyl-4-yl)-5,6,7,8-tetrahydro-imidazo[1,2-a]pyridin-6-ylmethyl]-amide; 2-Oxo-thiazolidine-4-carboxylic acid {2-(3',4'-dimethyl-biphenyl-4-yl)-5,6,7,8-tetrahydro-imidazo[1,2-a]pyridin-6-ylmethyl]-amide; (E)-N-[2-(3'4'-Dimethyl-biphenyl-4-yl)-5,6,7,8-tetrahydro-imidazo[1,2-a]pyridin-6-ylmethyl]-3-(1H-indol-3-yl)-acrylamide; N-[2-(3',4'-Dimethyl-biphenyl-4-yl)-5,6,7,8-tetrahydro-imidazo[1,2-a]pyridin-6-ylmethyl]-4-methyl-nicptinamide; 2-Cyclopent-1-enyl-N-[2-(3',4'-dimethyl-biphenyl-4-yl)-5,6,7,8-tetrahydro-imidazo[1,2-a]pyridin-6-ylmethyl]-acetamide; N-[2-(3',4'-Dimethyl-biphenyl-4-yl)-5,6,7,8-tetrahydro-imidazo[1,2-a]pyridin-6-ylmethyl]-2-(1H-indol-3-yl)-acetamide; N-t2-(3',4I-Dimethyl-biphenyl-4-yl)-5,6,7,8-tetrahydro-imidazo[1,2-a]pyridin-6-ylmethyl]-benzamide; Cyclohex-3-enecarboxylic acid [2-(3',4'-dimethyl-biphenyl-4-yl)-5,6,7,8-tetrahydro-imidazo[1,2-a]pyridin-6-ylmethyl]-amide; 5-Phenyl-pentanoic acid [2-(3',4'-dimethyl-biphenyl-4-yl)-5,6,7,8-tetrahydro-imidazo[1,2-a]pyridin-6-ylmethyl]-amide; 2-Benzo[b]thiophen-3-yl-N-[2-(3',4'-dimethyl-biphenyl-4-yl)-5,6,7,8-tetrahydro-imidazo[1,2-a]pyridin-6-ylmethyl]-acetamide; Tetrahydro-furan-3-carboxylic acid t2-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2-a]pyridin-6-ylmethyl]-2-indan-2-yl-acetamide; 2-Cyclopentyl-N-[2-(3',4'-dimethyl-biphenyl-4-yl)-5,6,7,8-tetrahydro-imidazo[1,2-a]pyridin-6-ylmethyl]-acetamide; 2-Methyl-cyclopropanecarboxylic acid-[2-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2-a]pyridin-6-ylmethyl]-3-(1H-indol-3-yl)-propionamide; N-t2-(3',4'-Dimethyl-biphenyl-4-yl)-5,6,7,δ-tetrahydro-imidazo[1,2-a]pyridin-6-ylmethyl]-2-(1,1-dioxo-tetrahydrothiophen-3-yl)-acetamide; N-[2-(3',4'-Dimethyl-biphenyl-4-yl)-5,6,7,8-tetrahydro-imidazo[1,2-a]pyridin-6-ylmethyl]-2-methoxy-nicotinamide; N-[2-(3$^I$,4$^I$-Dimethyl-biphenyl-4-yl)-5,6,7,8-tetrahydro-imidazo[1,2-a]pyridin-6-ylmethyl]-3-phenyl-propionamide; Thiophene-2-carboxylic acid [2-(3',4'-dimethyl-biphenyl-4-yl)-5,6,7,8-tetrahydro-imidazo[1,2-a]pyridin-6-ylmethyl]-amide; Furan-2-carboxylic acid [2-(3',4'-dimethyl-biphenyl-4-yl)-5,6,7,8-tetrahydro-imidazo[1,2-a]pyridin-6-ylmethyl]-amide; N-[2-(3',4'-Dinnethyl-biphenyl-4-yl)-5,6,7,8-tetrahydro-imidazo{1,2-a]pyridin-6-ylmethylj-nicotinamide; 1H-Indazole-3-carboxylic acid [2-(3',4'-dimethyl-biphenyl-4-yl)-5,6,7,8-tetrahydro-imidazo[1,2-a]pyridin-6-ylmethyl]-amide; 5-Methyl-1H-indole-2-carboxylic acid [2-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2ra]pyridin-6-ylmethyl]-3-indol-1-yl-propionamide; 6-Oxo-heptanoic acid [2-(3',4'-dimethyl-biphenyl-4-yl)-5,6,7,6-tetrahydro-imidazo[1,2-a]pyridin-6-ylmethyl]-amide; Thiophene-3-carboxylic acid [2-(3',4"-dimethyl-biphenyl-4-yl)-5,6,7,8-tetrahydro-imidazo[1,2-a]pyridin-6-ylmethyl]-amide; 6-Methyl-pyrazine^-carboxylic acid [2-(3',4'-dimethyl-biphenyl-4-yl)-5,6,7,8-tetrahydro-imidazo[1,2-a]pyridin-6-ylmethyl]-amide; Cyclopropanecarboxylic acid [2-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2-a]pyridin-6-ylmethyl]-6-methyl-nicotinamide; Cyclohex-1-enecarboxylic acid [2-(3',4'-dimethyl-biphenyl-4-yl)-5,6,7,8-tetrahydro-imidazo[1,2-a]pyridin-6-ylmethyl]-amide; 2-Cyclopropyl-N-[2-(3',4'-dimethyl-biphenyl-4-yl)-5,6,7,8-tetrahydro-imidazo[1,2-a]pyridin-6-ylmethyl]-acetamide; Cyclobutanecarboxylic acid [2-(3',4'-dimethyl-biphenyl-4-yl)-5,6,7,8-tetrahydro-imidazo[1,2-a]pyridin-6-ylmethyl]-amide; 4,5-Dichloro-isothiazole-3-carboxylic acid [2-(3',4'-dimethyl-biphenyl-4-yl)-5,6,7,8-tetrahydro-imidazo[1,2-a]pyridin-6-ylmethyl]-amide; N-[2-(3',4'-Dimethyl-biphenyl-4-yl)-5,6,7,8-tetrahydro-imidazo[1,2-a]pyridin-6-ylmethyl]-4-methyl-benzamide; (2,4-Dimethoxy-benzyl)-[2-(3',4'-dimethyl-biphenyl-4-yl)-imidazo[1,2-b]pyridazin-6-yl]-amine; 2-(3',4'-Dimethyl-biphenyl-4-yl)-imidazo[1,2-b]pyridazin-6-yl-hydrazine; 2-(3',4'-Dimethyl-biphenyl-4-yl)-6-morpholin-4-yl-imidazo[1,2-b]pyridazine; 2-(3',4'-Dimethyl-biphenyl-4-yl)-6-piperidin-1-yl-imidazo[1,2-b]pyridazine; 2-(3',4'-Dimethyl-biphenyl-4-yl)-6-(4-methyl-piperazin-1-yl)-imidazo[1,2-b]pyridazine; 2-(3',4'-Dimethyl-biphenyl-4-yl)-imidazo[1,2-b]pyridazin-6-ylamine; 1-[2-(3',4'-Dimethyl-biphenyl-4-yl)-imidazo[1,2-b]pyridazin-6-yl]-ethanol; [5-{3'4'Dimethyl-biphenyl-4-yl)-3-methyl-3H-imidazo[1,2-b][1,2,4]triazol-2-yl]-methanol; 2-[2-(3,4-Dimethyl-phenyl)-pyrimidin-5-yl]-imidazo[1,2-b]pyridazin-6-ylamine; 2-[6-(3,4-Dimethyl-phenyl)-pyridazin-3-yl]-imidazo[1,2-b]pyridazin-6-ylamine; 2-[2-(3-Fluoro-3',4'-dimethyl-biphenyl-4-yl)-imidazo[1,2-b]pyridazin-7-yl]-propan-2-ol; C-[5-(3',4'-Dimethyl-bipheny-4-yl)-3-methyl-3H-imidazo[1,2-b][1,2,4]triazol-2-yl]-methylamine; N-[5-(3',4'-Dimethyl-bipheny-4-yl)-3-methyl-3H-imidazo[1,2-b][1,2,4]triazol-2-ylmethyl]-methanesulfonamide; 1-[5-(3',4'-Dimethyl-biphenyl-4-yl)-3-methyl-3H-imidazo[1,2-b][1,2,4]triazol-2-yl]-ethanol; 2-[5-(3',4'-Dimethyl-biphenyl-4-yl)-3-methyl-3H-imidazo[1,2-b][1,2,4]triazol-2-yl]-propan-2-ol; 5-(3',4'-Dimethyl-biphenyl-4-yl)-3-methyl-3H-imidazo[1,2-b][1,2,4]triazole-2-carboxylic acid; 5-(3',4'-Dimethyl-biphenyl-4-yl)-3-methyl-3H-imidazo[1,2-b][1,2,4]triazole-2-carboxylic acid amide; and 5-(3',4'-Dimethyl-biphenyl-4-yl)-3-methyl-3H-imidazo[1,2-b][1,2,4]triazol-2-ylamine.

Other embodiments of C3aR antagonists are selected from heterocyclic compounds, as disclosed for example by Fairlie et al. in WO 2013/067578, which is expressly incorporated herein by reference in its entirety. In representative examples, the heterocyclic compounds are represented by formula (IV):

(IV)

wherein the ring A is selected from one of the following:

wherein X is N or CH; Y is O, S, NH, N($C_{1-3}$alkyl) or $CH_2$; and Z is N or C, provided that when Z is N, $R_3$ is absent;

wherein X is O, S, NH, N(C$_{1-3}$ alkyl) or CH$_2$; Y is N or CH; and Z is N or C, provided that when Z is N, R$_3$ is absent;

wherein X is N or CH; Y is N or CH; and Z is O, S, N or CH, provided that when Z is O or S, R$_3$ is absent; and
wherein:
R$_1$ is selected from arginine or an arginine mimetic;
R$_3$ is selected from hydrogen, halogen, alkyl, alkenyl, cycloalkyl, cycloalkenyl, aryl, heterocyclyl or heteroaryl;
R$_4$ is selected from hydrogen, alkyl, alkenyl, —(CH$_2$)$_m$cycloalkyl, —(CH$_2$)$_m$aryl, —(CH)$_m$heterocyclyl, —(CH$_2$)$_m$heteroaryl, —(CH$_2$)$_m$NHC(=NH)NH$_2$, —(CH$_2$)$_m$CONH$_2$, —(CH$_2$)$_m$CO$_2$H, —(CH$_2$)$_m$SR$_6$, —(CH$_2$)$_m$NH$_2$ or —(CH$_2$)$_m$OR$_6$;
R$_5$ is selected from alkyl, alkenyl, cycloalkyl, cycloalkenyl, aryl, heterocyclyl, heteroaryl or —NHR$_7$;
R$_6$ is selected from hydrogen, alkyl, cycloalkyl, aryl, heterocyclyl or heteroaryl;
R$_7$ is selected from —C(O)R$_8$, —C(O)OR$_8$, —C(O)NHR$_8$ or —S(O)$_2$R$_8$;
R$_8$ is selected from alkyl, alkenyl, —(CHR$_9$)$_p$cycloalkyl, —(CHR$_9$)$_p$cycloalkenyl, —(CHR$_9$)$_p$aryl, —(CHR$_9$)$_p$heterocyclyl or —(CHR$_9$)$_p$heteroaryl;
R$_9$ is selected from hydrogen, alkyl, alkenyl, cycloalkyl, cycloalkenyl, aryl, heterocyclyl or heteroaryl;
m is 0 or an integer from 1 to 6; and
p is 0 or an integer from 1 to 6;
wherein each cycloalkyl, cycloalkenyl, aryl, heteroaryl and heterocyclyl group may be optionally substituted with one or more optional substituents;
or a pharmaceutically acceptable salt thereof.

In non-limiting examples, the compounds of formula (IV) are represented by formula (IVa):

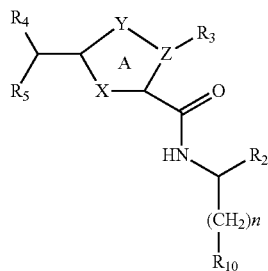

(IVa)

wherein:
R$_{10}$ is selected from guanidine or a guanidine mimetic;
R$_2$ is selected from a carboxylic acid bioisostere;
n is an integer from 1 to 4;
R$_3$, R$_4$ and R$_5$ are as defined for formula (IV).

In specific embodiments, the ring A is selected from one of:

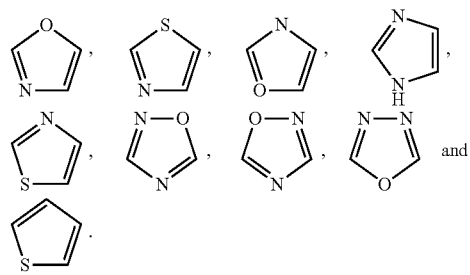

Suitably, in the compounds of formula (IV) or (IVa), R$_{10}$ is selected from:

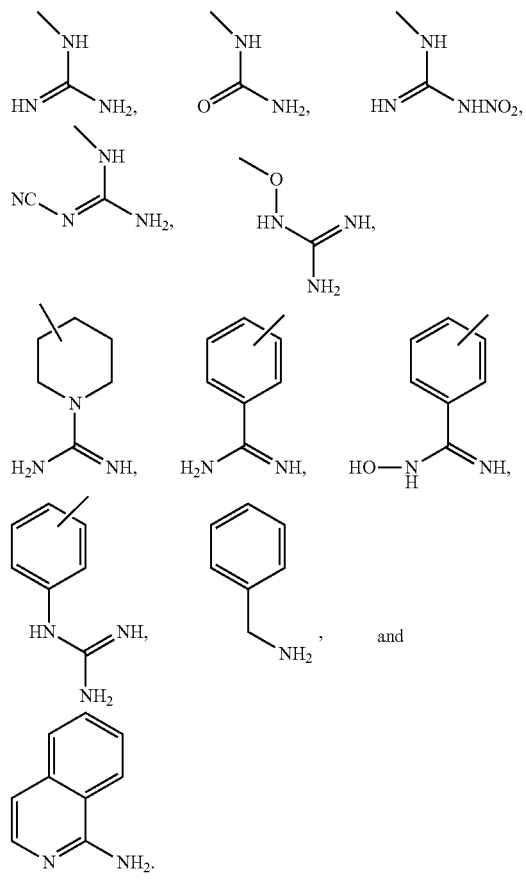

In some embodiments of the compounds of formula (IV) or (IVa), R$_2$ is selected from: —CO$_2$H, —C(OH)(CF$_3$)$_2$, —C(O)NHSO$_2$aryl, —C(O)NHSO$_2$alkyl

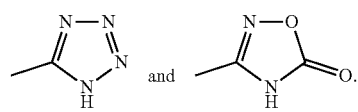

Suitably, in the compounds of formula (IV) or (IVa), R$_3$ is selected from: methyl, ethyl, propyl, isopropyl, cyclohexyl, cyclohexenyl, cyclohexadienyl and phenyl.

In some embodiments of the compounds of formula (IV) or (IVa), R$_4$ is selected from: hydrogen, —CH$_3$, cyclohexyl, phenyl, —(CH$_2$)$_2$NHC(=NH)NH$_2$, —CH$_2$—CONH$_2$, —CH$_2$CO$_2$H, —CH$_2$SH, —(CH$_2$)$_2$CONH$_2$, —(CH$_2$)$_2$CO$_2$H, —CH$_2$(4-imidazolyl), —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH, OH, —CH(CH$_3$)OH, —CH$_2$(3-indolyl), —CH$_2$(4-hydroxyphenyl), —CH(CH$_3$)$_2$ and —(CH$_2$)cyclohexyl.

In some embodiments of the compounds of formula (IV) or (IVa), R$_5$ is selected from: —NHC(O)R$_8$, —NHC(O)R$_8$, —NHC(O)NHR$_8$ and —NHSO$_2$R$_8$.

Suitably, in the compounds of formula (IV) or (IVa), R$_8$ is selected from: C$_{1-6}$alkyl, cycloalkyl, cycloalkenyl, aryl, heterocyclyl, heteroaryl, —CH$_2$cycloalkyl, —CH$_2$cycloalkenyl, —CH$_2$aryl, —CH$_2$heterocyclyl, —CH$_2$heteroaryl and —CH(CH$_3$)aryl, wherein each cycloalkyl, cycloalkenyl, aryl, heterocyclyl and heteroaryl are optionally substituted with one or more of C$_{1-6}$alkyl, —OC$_{1-6}$ alkyl, —NHC$_{1-6}$alkyl, —N(C$_{1-6}$alkyl)$_2$, halogen, —C(O)phenyl, —Ophenyl, —CF$_3$, —N=N-phenyl and OH.

The invention not only encompasses known C3aR antagonists but also C3aR antagonists identified by any suitable screening assay. Accordingly, the present invention extends to methods of screening for modulatory agents that are useful for antagonizing C3aR and, in turn, stimulating or enhancing the development, mobilization, proliferation and/or differentiation of a neutrophil-containing leukocyte population that inhibits growth and/or metastasis of a tumor and for treating or preventing a hyperproliferative cell disorder. In some embodiments, the screening methods comprise (1) contacting a preparation with a test agent, wherein the preparation comprises (i) a polypeptide comprising an amino acid sequence corresponding to at least a fragment of a C3aR; or (ii) a polynucleotide comprising at least a portion of a genetic sequence (e.g., a transcriptional control sequence) that regulates the expression of C3aR, wherein the genetic sequence is operably linked to a reporter gene; and (2) detecting a change in the level or functional activity (e.g., signaling) of C3aR, or an expression product of the reporter gene, relative to a reference level or functional activity in the absence of the test agent. A detected reduction in the level or activity of C3aR, or expression product, relative to the reference level or functional activity indicates that the test agent is useful for stimulating or enhancing the development, mobilization, proliferation and/or differentiation of a neutrophil-containing leukocyte population that inhibits growth and/or metastasis of a tumor and for treating or preventing a hyperproliferative cell disorder. Suitably, this is confirmed by analyzing or determining whether the test agent stimulates or enhances the development, mobilization, proliferation and/or differentiation of a neutrophil-containing leukocyte population that inhibits growth and/or metastasis of a tumor and treats or prevents a hyperproliferative cell disorder. Exemplary assays of this type are disclosed for example in U.S. Pat. No. 5,942,405 supra. Alternatively, a receptor binding assay may be performed as disclosed for example in WO 2013/067578 supra.

Modulators falling within the scope of the present invention include antagonists of the level or functional activity of C3aR, including antagonistic antigen-binding molecules, and inhibitor peptide fragments, antisense molecules, ribozymes, RNAi molecules and co-suppression molecules as well as polysaccharide and lipopolysaccharide inhibitors of C3aR function.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of C3aR are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogues.

Screening may also be directed to known pharmacologically active compounds and chemical analogues thereof.

Compounds may be further tested in the animal models to identify those compounds having the most potent in vivo effects. These molecules may serve as "lead compounds" for the further development of pharmaceuticals by, for example, subjecting the compounds to sequential modifications, molecular modeling, and other routine procedures employed in rational drug design.

3.2 Mobilizers of Hematopoietic Stem Cells and/or Progenitor Cells

Several classes of agents have been shown to increase the circulation of progenitor and stem cells by "mobilizing" them from the marrow into the peripheral blood. These include agents that decrease the expression or function of a chemokine (the function being the binding of the chemokine to its receptor and further signaling), particularly CXCL12, as well as those that block or antagonize the chemokine receptor, CXCR4.

Accordingly, in some embodiments, the mobilization agent may be an agent that decreases the expression or function of a chemokine, more particularly, CXCL12, also known as SDF-1. The human amino acid sequence of SDF-1 comprises the sequence:
MNAKVVVVLVLVLTALCLSDGKPVSL-SYRCPCRFFESHVARANVKHLKILNTPNCALQI-VARLKNNNR QVCIDPKLKWIQEYLEKALNKRFKM [SEQ ID NO: 3], which corresponds to GenBank accession number NP_000600. The alpha isoform has GenBank accession number NP 954637. The beta isoform has GenBank accession number NP_000600. The gamma isoform has GenBank accession number NP_001029058.

Alternatively, the mobilization agent may be an agent that blocks or antagonizes a chemokine receptor, in particular, CXCR4. The human amino acid sequence of CXCR4 comprises the sequence:

[SEQ ID NO: 4]
MEGISSIPLPLLQIYTSDNYTEEMGSGDYDSMKEPCFREENANFNKIFLP

TIYSIIFLTGIVGNGLVILVMGYQKKLRSMTDKYRLHLSVADLLFVITLP

FWAVDAVANWYFGNFLCKAVHVIYTVNLYSSVLILAFISLDRYLAIVHAT

NSQRPRKLLAEKVVYVGVWIPALLLTIPDFIFANVSEADDRYICDRFYPN

DLWVVVFQFQHIMVGLILPGIVILSCYCIIISKLSHSKGHQKRKALKTTV

ILILAFFACWLPYYIGISIDSFILLEIIKQGCEFENTVHKWISITEALAF

FHCCLNPILYAFLGAKFKTSAQHALTSVSRGSSLKILSKGKRGGHSSVST

ESESSSFHSS, which corresponds to GenBank accession number CAA12166.

Chemokines are a superfamily of chemoattractant proteins. Chemokines regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines. Two minor subgroups contain only one of the two cysteines (C) or have three amino acids between the cysteines (CX3C). In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem, 269, 232-237), HUMSTR (Federsppiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877). CXCR4 is widely expressed on cells of hematopoietic origin, and is a major co-receptor with CD4 for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877).

Chemokines are thought to mediate their effect by binding to seven transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF-1), also known as CXCL12, is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1α (SDF-1α) and stromal cell derived factor-1β (SDF-1β) are closely related (together referred to herein as SDF-1). The native amino acid sequences of SDF-1α and SDF-1β are known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 kb. SDF-1 was initially characterized as a pre-B cell-stimulating factor and as a highly efficient chemotactic factor for B cells and monocytes (Bleu) et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with perinatal lethality, including abnormalities in cardiac development, B-cell lymphopoiesis, and bone marrow myelopoiesis (Nagasawa et al. (1996) Nature 382:635-637). SDF-1 is functionally distinct from other chemokines in that it is reported to have a fundamental role in the trafficking, export and homing of bone marrow progenitor cells (Aiuti, A., et al. (1996) J. Exp. Med. 185, 111-120 and Nagasawa, T., et al. (1996) Nature 382, 635-638). SDF-1 is also structurally distinct in that it has only about 22% amino acid sequence identity with other CXC chemokines.

Agents that decrease the expression of CXCL12 or that block or antagonize CXCR4 may be selected from small organic molecules, polypeptides, nucleic acids and carbohydrates. In more particular embodiments, the polypeptides that decrease the expression of CXCL12 may be selected from the group consisting of a cytokine, a colony stimulating factor, a protease or a chemokine other than CXCL12. The cytokine may be selected from the group consisting of interleukin-1 (IL-1), interleukin-3 (IL-3), interleukin-6 (IL-6), interleukin-11 (IL-11), interleukin-7 (IL-7) and interleukin-12 (IL12). The protease may be selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26). The chemokine other than CXCL12 may be selected from the group consisting of IL-8, MIP-1α and Grog. The colony stimulating factor may be selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof. The nucleic acid may be a DNA or an RNA molecule. The nucleic acid may be a small interfering RNA (siRNA) molecule or an antisense molecule specific for CXCL12 or CXCR4. The carbohydrate may be a sulfated carbohydrate selected from the group consisting of Fucoidan and sulfated dextran.

In specific embodiments, the mobilizer(s) is(are) mobilizers are selected from G-CSF, GM-CSF, erythropoietin (which is now commonly used among cancer patients undergoing chemotherapy to maintain hemoglobin in the near normal range, also has some ability to mobilize CD34$^+$ cells), stem cell factor (SCF), polysaccharides such as zymosan, chemokines such as IL-8 and Gro-β, growth factors such as vascular endothelial growth factor (VEGF), and CXCR4 antagonists.

In some embodiments, the mobilizer is selected from CXCR4 antagonists. Illustrative CXCR4 antagonists include aromatic-linked polyamine macrocyclic compounds, as described for example in U.S. Pat. No. 5,583,131, which is expressly incorporated herein by reference in its entirety. Compounds disclosed in U.S. Pat. No. 5,583,131 can be represented by formula V:

in which:

Z and Y are identical cyclic polyamine moieties having from 9 to 20 ring members and from 3 to 6 amine nitrogens in the ring spaced by 2 or more carbon atoms from each other, A is an aromatic or heteroaromatic moiety other than quinoline, and R and R' are each methylene linked to an amine nitrogen atom in Z and in Y, the amine nitrogens being otherwise unsubstituted, or acid addition salts, metal complexes or prodrugs thereof.

Suitably, the cyclic polyamine moieties may be substituted or unsubstituted, and suitable substituents are alkyl and/or aryl groups, e.g., of up to 10 carbon atoms, and any other atoms or groups which do not substantially adversely affect the activity or toxicity of the compounds. Preferred moieties are those of 10 to 15 ring members, and there are preferably 3 or 4 amine nitrogen atoms.

The aromatic or heteroaromatic moiety A tethers Y and Z through the linking groups R and R'. Moiety A may be phenyl or fused aromatic such as naphthyl, heterocyclic such as pyridyl or thiophenyl, fused heterocyclic or joined aromatic and/or joined heteroaromatic, for example biphenyl or bipyridyl, respectively. The moieties A may also be substituted at single or multiple non-linking positions with electron-donating groups, e.g., alkyl, thio, thioalkyl, hydroxyl, alkoxyl, amino and derivatives thereof, or electron-withdrawing groups or atoms, e.g., nitro, halogen, carboxy, carboxamido, sulfonic acid and derivatives thereof.

In some embodiments, each moiety Z and Y has 14 ring members and 4 amine nitrogens in the ring. Representative compounds of this type include: 1,1'-[1,3-phenylenebis(methylene)]-bis-1,4,8,11-tetra-azacyclotetradecane; 1,1'-[1,4-phenylenebis(methylene)]-bis-1,4,8,11-tetra-azacyclotetradecane (AMD3100; Plerixafor); 1,1'-[1,4-phenylene-bis-(methylene)]-bis-1,4,8,11-tetraazacyclotetradecane; a bis-copper complex of 1,1'-[1,4-phenylene-bis-(methylene)]-bis-1,4,8,11-tetraazacyclotetradecane; 1,1'-[3,3'-biphenylene-bis-(methylene)]-bis-1,4,8,11-tetraazacyclotetradecane; 11,11'-[1,4-phenylene-bis-(methylene)]-bis-1,4,7,11-tetraazacyclotetradecane; 1,11'-[1,4-phenylene-bis-(methylene)]-1,4,8,11-tetraazacyclotetradecane-1,4,7,11-tetraazacyclotetradecane; 1,1' [2,6 pyridine bis-(methylene)]-bis-1,4,8,11-tetraazacyclotetradecane; 1,1-[3,5-pyridine-bis-(methylene)]-bis-1,4,8,11-tetraazacyclotetradecane; 1,1'-[2,5-thiophene-bis-(methylene)]-bis-1,4,8,11-tetraazacyclotetradecane; 1,1'-[4,4'-(2,2'-bipyridine)-bis-(methylene)]-bis-1,4,8,11-tetraazacyclotetradecane; 1,1'-[2,9-(1,10-phenanthroline)-bis-(methylene)]-bis-1,4,8,11-tetraazacyclotetradecane; 1,1'-[1,3-phenylene-bis-(methylene)]-bis-1,4,7,10-tetraazacyclotetradecane; 1,1'-[1,4-phenylene-bis-(methylene)]-bis-1,4,7,10-tetraazacyclotetradecane; 1,1'-[5-nitro-1,3-phenylenebis(methylene)]bis-1,4,8,11-tetraazacyclotetradecane; 1'1'-[2,4,5,6-tetrachloro-1,3-phenyleneis(methylene)]bis-1,4,8,11-tetraazacyclotetradecane; 1,1'-[2,3,5,6-tetra-fluoro-1,4-phenylenebis(methylene)]bis-1,4,8,11-tetrazacyclotetradecane; 1,1'-[1,4-naphthylene-bis-(methylene)]bis-1,4,8,11-tetraazacyclotetradecane; 1,1'-[1,3-phenylenebis-(methylene)]bis-1,5,9-triazacyclododecane; 1,1'-[1,4-phenylene-bis-(methylene)]-1,5,9-trlazacyclododecane; a bis-zinc complex of 1,1'[1,4-phenylene-bis-(methylene)]-bis-1,4,8,11-tetraazacyclotetradecane; 1,1'-[3,3'-biphenylene-bis-(methylene)]-bis-1,4,8,11-tetraazacyclotetradecane; 1,1'-[2,6-pyridine-bis-(methylene)]-bis-1,4,8,11-tetraazacyclotetradecane; 1,1'-[3,5-pyridine-bis-(methylene)]-bis-1,4,8,11-tetraazacyclotetradecane; 1,1'-[2,5-thiophene-bis-(methylene)]-bis-1,4,8,11-tetraazacyclotetradecane; 1,1'-[4,4'-(2,2'-bipyridine)-bis-(methylene)]-bis-1,4,8,11-tetraazacyclotetradecane; 1,1'-[2,9-(1,10-phenanthroline)-bis-(methylene)]-bis-1,4,8,11-tetraazacyclotetradecane; 1,1'-[1,3-phenylene-bis-(methylene)]-bis-1,4,7,10-tetraazacyclotetradecane; 1,1'-[1,4-phenylene-bis-(methylene)]-bis-1,4,7,10-tetraazacyclotetradecane; 1,1'-[2,5-dimethyl-1,4-phenylenebis-(methylene)]-bis-1,4,8,11-tetraazacyclotetradecane; 1,1'-[2,5-dichloro-1,4-phenylenebis-(methylene)]-bis-1,4,8,11-tetraazacyclotetradecane; 1,1'-[2-bromo-1,4-phenylenebis-(methylene)]-bis-1,4,8,11-tetraazacyclotetradecane; and 1,1'-[6-phenyl-2,4-pyridinebis-(methylene)]-bis-1,4,8,11-tetraazacyclotetradecane, optionally in the form of acid addition salts.

In other embodiments, CXCR4 antagonists polyamine macrocyclic compounds, as described for example in U.S. Pat. No. 6,97,102, which is expressly incorporated herein by reference in its entirety. Exemplary compounds of this type are represented by formula VI:

wherein:

Z is a cyclic polyamine containing 9-32 ring members of which 2-8 are nitrogen atoms, said nitrogen atoms separated from each other by at least 2 carbon atoms, and wherein said heterocycle may optionally contain additional heteroatoms besides nitrogen and/or may be fused to an additional ring system; or Z is of the formula VIa:

wherein A comprises a monocyclic or bicyclic fused ring system containing at least one N and B is H or an organic moiety of 1-20 atoms; Z' may be embodied in a form as defined by Z above, or alternatively may be of the formula —N(R)—(CR$_2$)$_n$—X wherein each R is independently H or straight, branched or cyclic alkyl (1-6C), n is 1 or 2, and X is an aromatic ring, including heteroaromatic rings, or is a mercaptan; "linker" represents a bond, alkylene (1-6C) or may comprise aryl, fused aryl, oxygen atoms contained in an alkylene chain, or may contain keto groups or nitrogen or sulfur atoms.

In general, in compounds of formula (VI), exemplary embodiments of Z and Z' are cyclic polyamine moieties having from 9-24C that include 3-5 nitrogen atoms, illustrative examples of which include: 1,5,9,13-tetraazacyclohexadecane; 1,5,8,11,14-pentaazacyclohexadecane; 1,4,8,11-tetraazacylotetradecane; 1,5,9-triazacyclododecane; 1,4,7,10-tetraazacyclododecane; and the like, including such cyclic polyamines which are fused to an additional aromatic or heteroaromatic rings and/or containing a heteroatom other than nitrogen incorporated in the ring. Embodiments wherein the cyclic polyamine contains a fused additional cyclic system or one or more additional heteroatoms are described in U.S. Pat. No. 5,698,546 and WO 01/44229 each of which is expressly incorporated herein in its entirety. In other embodiments, the compounds of formula VI are selected from 3,7,11,17-tetraazabicyclo(13.3.1)heptadeca-1(17),13,15-triene; 4,7,10,17-tetraazabicyclo(13.3.1)heptadeca-1(17),13,15-triene; 1,4,7,10-tetraazacyclotetradecane; 1,4,7-triazacyclotetradecane; and 4,7,10-triazabicyclo(13.3.1)heptadeca-1(17),13,15-triene.

When Z' is other than a cyclic polyamine as defined in Z, its preferred embodiments are set forth in U.S. Pat. No. 5,817,807, also incorporated herein by reference in its entirety. Desirable forms where Z is of the formula VIa, wherein A comprises a monocyclic or bicyclic fused ring system containing at least one N and B is H or an organic moiety of 1 20 atoms are disclosed in WO 00/56729; WO 02/22600; WO 02/34745; and WO 02/22599, all of which are expressly incorporated herein by reference in their entirety.

Exemplary forms of the linker moiety include those wherein the linker is a bond, or wherein the linker includes an aromatic moiety flanked by alkylene, preferably methylene moieties. Preferred linking groups include the methylene bracketed forms of 1,3-phenylene, 2,6-pyridine, 3,5-pyridine, 2,5-thiophene, 4,4'-(2,2'-bipyrimidine); 2,9-(1,10-phenanthroline) and the like. In specific embodiments, the linker is 1,4-phenylene-bis-(methylene).

Particularly advantageous embodiments of the compound of the formula (VI) include 2,2'-bicyclam; 6,6'-bicyclam; the embodiments set forth in U.S. Pat. Nos. 5,021,409, and 6,001,826, and in particular 1,1'-[1,4-phenylene-bis(methylene)]-bis-1,4,8,11-tetraazacyclotetradecane, set forth in U.S. Pat. No. 5,583,131, and designated herein as AMD3100 or Plerixafor.

Other embodiments of formula VIa include N-[1,4,8,11-tetraazacyclotetradecanyl-1,4-phenylenebis(methylene)]-2-aminomethyl)pyridine; 7,7'-[1,4-phenylenebis(methylene)]bis-4,7,10,17-tetraazabicyclo-[13.3.1]heptadeca-1(17),13,15-triene; 7,7'-[1,4-phenylenebis(methylene)]bis-3,7,11,17-tetraazabicyclo[13.3.1]heptadeca-1(17),13,15-triene; 1,1'-[1,3-phenylenebis(methylene)]-bis-1,4,8,11-tetra-azacyclotetradecane; 1,1'-[1,4-phenylenebis(methylene)]-bis-1,4,8,11-tetra-azacyclotetradecane; 1,1'-[1,4-phenylene-bis-(methylene)]-bis-1,4,7,10-tetraazacyclotetradecane; 1,1'-[1,3-phenylene-bis-(methylene)]-bis-1,4,7,10-tetraazacyclotetradecane; 11,11'-(1,2-propanediyl)bis-1,4,8,11-tetraazacyclotetradecane; N-[4-(1,4,7-triazacyclotetra-decane)-1,4-phenylenebis(methylene)]-2-(aminomethyl)pyridine; N-[7-(4,7,10-triazabicyclo[13.3.1]heptadeca-1(17),13,15-triene)-1,4-phenylenebis(methylene)]-2-(aminomethyl)pyridine; N-[7-(4,7,10,17-tetraazabicyclo[13.3.1]heptadeca-1(17),13,15-triene)-1,4-phenylenebis(methylene)]-2-(aminomethyl)pyridine; N-[4-[4,7,10,17-tetraazabicyclo[13.3.1]heptadeca-1(17),13,15-triene]-1,4-phenylenebis(methylene)]-2-(aminomethyl)pyridine; 3,3'-(bis-1,5,9,13-tetraazacyclohexadecane); 3,3'-(bis-1,5,8,11,14-pentaazacyclohexadecane), methylene (or polymethylene) di-1-N-1,4,8,11-tetraazacyclotetradecane; 3,3'-bis-1,5,9,13,-tetraazacyclohexadecane; 3,3'-bis-1,5,8,11,14-pentaazacyclohexadecane; 5,5'-bis-1,4,8,11-tetraazacyclotetradecane; 2,5'-bis-1,4,8,11-tetraazacyclotetradecane; 2,6'-bis-1,4,8,11-tetraazacyclotetradecane; 11,11'-(1,2-ethanediyl)bis-1,4,8,11-tetraazacyclotetradecane; 11,11'-(1,2-propanediyl)bis-1,4,8,11-tetraazacyclotetradecane; 11,11'-(1,2-butanediyl)bis-1,4,8,11-tetraazacyclotetradecane; 11,11'-(1,2-pentanediyl)bis-1,4,8,11-tetraazacyclotetradecane; 11,11'-(1,2-hexanediyl)bis-1,4,8,11-tetraazacyclotetradecane; 3,3'-bis-1,5,9,13-tetraazacyclohexadecane; 3,3'-bis-1,5,8,11,14-pentaazacyclohexadecane; 5,5'-bis-1,4,8,11-tetraazacyclotetradecane; 2,5'-bis-1,4,8,11-tetraazacyclotetradecane; 2,6'-bis-1,4,8,11-tetraazacyclotetradecane; 11,11'-(1,2-ethanediyl)bis-1,4,8,11-tetraazacyclotetradecane; 11,11'-(1,2-propanediyl)bis-1,4,8,11-tetraazacyclotetradecane; 11,11'-(1,2-butanediyl)bis-1,4,8,11-tetraazacyclotetradecane; 11,11'-(1,2-pentanediyl)bis-1,4,8,11-tetraazacyclotetradecane; 11,11'-(1,2-hexanediyl)bis-1,4,8,11-tetraazacyclotetradecane; 1,1'-[1,3-phenylenebis(methylene)]-bis-1,4,8,11-tetra-azacyclotetradecane; 1,1'-[1,4-phenylenebis(methylene)]-bis-1,4,8,11-tetra-azacyclotetradecane; 1,1'-[3,3'-biphenylene-bis-(methylene)]-bis-1,4,8,11-tetraazacyclotetradecane; 11,11'-[1,4-phenylene-bis-(methylene)]-bis-1,4,7,11-tetraazacyclotetradecane; 1,11'-[1,4-phenylene-bis(methylene)]-1,4,8,11-tetraazacyclotetradecane; 1,1'-[2,6-pyridine-bis-(methylene)]-bis-1,4,8,11-tetraazacyclotetradecane; 1,1-[3,5-pyridine-bis-(methylene)]-bis-1,4,8,11-tetraazacyclotetradecane; 1,1'-[2,5-thiophene-bis-(methylene)]-bis-1,4,8,11-tetraazacyclotetradecane; 1,1'-[4,4'-(2,2'-bipyridine)-bis-(methylene)]-bis-1,4,8,11-tetraazacyclotetradecane; 1,1'-[2,9-(1,10-phenanthroline)-bis-(methylene)]-bis-1,4,8,11-tetraazacyclotetradecane; 1,1'-[1,3-phenylene-bis-(methylene)]-bis-1,4,7,10-tetraazacyclotetradecane; 1,1'-[1,4-phenylene-bis-(methylene)]-bis-1,4,7,10-tetraazacyclotetradecane; 1,1'-[5-nitro-1,3-phenylenebis(methylene)]bis-1,4,8,11-tetraazacyclotetradecane; 1,1'-[2,4,5,6-tetrachloro-1,3-phenyleneis(methylene)]bis-1,4,8,11-tetraazacyclotetradecane; 1,1'-[2,3,5,6-tetrafluoro-1,4-phenylenebis(methylene)]bis-1,4,8,11-tetraazacyclotetradecane; 1,1'-[1,4-naphthylene-bis-(methylene)]bis-1,4,8,11-tetraazacyclotetradecane; 1,1'-[1,3-phenylenebis-(methylene)]bis-1,5,9-triazacyclododecane; 1,1'-[1,4-phenylene-bis-(methylene)]-1,5,9-triazacyclododecane; 1,1'-[2,5-dimethyl-1,4-phenylenebis-(methylene)]-bis-1,4,8,11-tetraazacyclotetradecane; 1,1'-[2,5-dichloro-1,4-phenylenebis-(methylene)]-bis-1,4,8,11-tetraazacyclotetradecane; 1,1'-[2-bromo-1,4-phenylenebis-(methylene)]-bis-1,4,8,11-tetraazacyclotetradecane; 1,1'-[6-phenyl-2,4-pyridinebis-(methylene)]-bis-1,4,8,11-tetraazacyclotetradecane; 7,7'-[1,4-phenylene-bis(methylene)]bis-3,7,11,17-tetraazabicyclo[13.3.1]heptadeca-1(17),13,15-triene; 7,7'-[1,4-phenylene-bis(methylene)]bis[15-chloro-3,7,11,17-tetraazabicyclo[13.3.1]heptadeca-1(17),13,15-triene]; 7,7'-[1,4-phenylene-bis(methylene)]bis[15-methoxy-3,7,11,17-tetraazabicyclo[13.3.1]heptadeca-1(17),13,15-triene]; 7,7'-[1,4-phenylene-bis(methylene)]bis-3,7,11,17-tetraazabicyclo[13.3.1]-heptadeca-13,16-triene-15-one; 7,7'-[1,4-phenylene-bis(methylene)]bis-4,7,10,17-tetraazabicyclo[13.3.1]-heptadeca-1(17),13,15-triene; 8,8'-[1,4-phenylene-bis(methylene)]bis-4,8,12,19-tetraazabicyclo[15.3.1]nonadeca-1(19),15,17-triene; 6,6'-[1,4-phenylene-bis(methylene)]bis-3,6,9,15-tetraazabicyclo[11.3.1]pentadeca-1(15),11,13-triene; 6,6'-[1,3-phenylene-bis(methylene)]bis-3,6,9,15-tetraazabicyclo[11.3.1]pentadeca-1(15),11,13-triene; 17,17'-[1,4-phenylene-bis(methylene)]bis-3,6,14,17,23,24-hexaazatricyclo[17.3.1.1$^{8,12}$]tetracosa-1(23),8,10,12

(24),19,21-hexaene; N-[1,4,8,11-Tetraazacyclotetradecanyl-1,4-phenylenebis(methylene)]-2-(amino-methyl)pyridine; N-[1,4,8,11-Tetraazacyclotetradecanyl-1,4-phenylenebis(methylene)]-N-methyl-2-(aminomethyl)pyridine; N-[1,4,8,11-Tetraazacyclotetradecanyl-1,4-phenylenebis(methylene)]-4-)amino-methyl)pyridine; N-[1,4,8,11-Tetraazacyclotetradecanyl-1,4-phenylenebis(methylene)]-3-(amino-methyl)pyridine; N-[1,4,8,11-Tetraazacyclotetradecanyl-1,4-phenylenebis(methylene)]-(2-amino-methyl-5-methyl)pyrazine; N-[1,4,8,11-Tetraazacyclotetradecanyl-1,4-phenylenebis(methylene)]-2-(amino-ethyl)pyridine; N-[1,4,8,11-Tetraazacyclotetradecanyl-1,4-phenylenebis(methylene)]-2-(amino-methyl)thiophene; N-[1,4,8,11-Tetraazacyclotetradecanyl-1,4-phenylenebis(methylene)]-2-(amino-ethyl)mercaptan; N-[1,4,8,11-Tetraazacyclotetradecanyl-1,4-phenylenebis(methylene)]-2-amino-benzylamine; N-[1,4,8,11-Tetraazacyclotetradecanyl-1,4-phenylenebis(methylene)]-4-amino-benzylamine; N-[1,4,8,11-Tetraazacyclotetradecanyl-1,4-phenylenebis(methylene)]-4-(amino-ethyl)imidazole; N-[1,4,8,11-Tetraazacyclotetradecanyl-1,4-phenylenebis(methylene)]-benzylamine; N-[1,4,8,11-Tetraazacyclotetradecanyl-1,4-phenylenebis(methylene)]-purine; N-[1,4,8,11-Tetraazacyclotetradecanyl-1,4-phenylenebis(methylene)]-4-phenylpiperazine; N-[4-(1,4,7-Triazacyclotetra-decanyl)-1,4-phenylenebis(methylene)]-2-(aminomethyl)pyridine; N-[7-(4,7,10,17-Tetraazabicyclo[13.3.1]heptadeca-1(17),13,15-trienyl)-1,4-phenylenebis(methylene)]-2-(aminomethyl)pyridine; N-[7-(4,7,10-Triazabicyclo[13.3.1]heptadeca-1(17),13,15-trienyl)-1,4-phenylenebis(methylene)]-2-(aminomethyl)pyridine; N-[4-[4,7,10-Triazabicyclo[13.3.1]heptadeca-1(17),13,15-trienyl]-1,4-phenylenebis(methylene)]-2-(aminomethyl)pyridine; N-[1-(1,4,7-Triazacyclotetra-decanyl)-1,4-phenylenebis(methylene)]-2-(aminomethyl)pyridine; N-[4-[4,740,17-Tetraazabicyclo[13.3.1]heptadeca-1(17),13,15-trienyl]-1,4-phenylenebis(methylene)]-2-(aminomethyl)pyridine; N-[3-(3,6,17-Triazabicyclo[13.3.1]heptadeca-1(17),13,15-trienyl)-1,4-phenylenebis(methylene)]-2-(aminomethyl)pyridine; N-[3-(3,6,17-Triazabicyclo[13.3.1]heptadeca-1(17),13,15-trienyl)-1,3-phenylenebis(methylene)]-2-(aminomethyl)pyridine; N-[4-(4,7,17-Triazabicyclo[13.3.1]heptadeca-1(17),13,15-trienyl)-1,4-phenylenebis(methylene)]-2-(aminomethyl)pyridine; N-[7-(4,7,17-Triazabicyclo[13.3.1]heptadeca-1(17),13,15-trienyl)-1,4-phenylenebis(methylene)]-2-(aminomethyl)pyridine; N-[6-(3,6,9-Triazabicyclo[11.3.1]pentadeca-1(15),11,13-trienyl)-1,3-phenylenebis(methylene)]-2-(aminomethyl)pyridine; N-[7-(4,10,17-Triazabicyclo[13.3.1]heptadeca-1(17),13,15-trienyl)-1,4-phenylenebis(methylene)]-2-(aminomethyl)pyridine; N-[4-(1,7-Diazacyclotetradecanyl)-1,4-phenylenebis(methylene)]-2-(aminomethyl)pyridine; N-[7-(4,10-Diazabicyclo[13.3.1]heptadeca-1(17),13,15-trienyl)-1,4-phenylenebis(methylene)]-2-(aminomethyl)pyridine; N-[4-(11-Fluoro-1,4,7-triazacyclotetradecanyl)-1,4-phenylenebis(methylene)]-2-(aminomethyl)pyridine; N-[4-(11,11-difluoro-1,4,7-triazacyclotetradecanyl)-1,4-phenylenebis(methylene)]-2-(aminomethyl)pyridine; N-[4-(1,4,7-triazacyclotetradecan-2-one)-yl))-1,4-phenylenebis(methylene)]-2-(aminomethyl)pyridine; N-[12-(5-oxa-1,9-diazacyclotetradecanyl)-1,4-phenylenebis(methylene)]-2-(aminomethyl)pyridine; N-[4-(11-oxa-1,7-diazacyclotetradecanyl)-1,4-phenylenebis(methylene)]-2-(aminomethyl)pyridine; N-[4-(11-thia-1,7-diazacyclotetradecanyl)-1,4-phenylenebis(methylene)]-2-(aminomethyl)pyridine; N-[4-(11-sulfoxo-1,7-diazacyclotetradecanyl)-1,4-phenylenebis(methylene)]-2-(aminomethyl)pyridine; N-[4-(11-sulfono-1,7-diazacyclotetradecanyl)-1,4-phenylenebis(methylene)]-2-(aminomethyl)pyridine; N-[4-(1,4,7-triazacyclotetradecan-3-one)-yl))-1,4-phenylenebis(methylene)]-2-(aminomethyl)pyridine; N-(2-pyridinylmethyl)-N'-(6,7,8,9-tetrahydro-5H-cyclohepta[b]pyridin-9-yl)-1,4-benzenedimethanamine; N-(2-pyridinylmethyl)-N'-(5,6,7,8-tetrahydro-8-quinolinyl)-1,4-benzenedim-ethanamine; N-(2-pyridinylmethyl)-N'-(6,7-dihydro-5H-cyclopenta[b]pyridin-7-yl)-1,4-b-enzenedimethanamine; N-(2-pyridinylmethyl)-N'-(1,2,3,4-tetrahydro-1-naphthalenyl)-1,4-benzenedimethanamine; N-(2-pyridinylmethyl)-N'-(1-naphthalenyl)-1,4-benzenedimethanamine; N-(2-pyridinylmethyl)-N'-(8-quinolinyl)-1,4-benzenedimethanamine; N-(2-pyridinylmethyl)-N'-[2-[(2-pyridinylmethyl)amino]ethyl]-N'-(1-methyl-1,2,3,4-tetrahydro-8-quinolinyl)-1,4-benzene dimethanamine; N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine; N-(2-pyridinylmethyl)-N'-(1,2,3,4-tetrahydro-8-quinolinyl)-1,4-benzenedimethanamine; N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine; N-(2-pyridinylmethyl)-N'-(2-phenyl-5,6,7,8-tetrahydro-8-quinolinyl)-1,4-benzenedimethanamine; N,N'-bis(2-pyridinylmethyl)-N'-(2-phenyl-5,6,7,8-tetrahydro-8-quinolinyl)-1,4-benzenedimethanamine; N-(2-pyridinylmethyl)-N'-(5,6,7,8-tetrahydro-5-quinolinyl)-1,4-benzenedimethanamine; N-(2-pyridinylmethyl)-N'-(1H-imidazol-2-ylmethyl)-N'-(5,6,7,8-tetrahydro-5-quinolinyl)-1,4-benzenedimethanamine; N-(2-pyridinylmethyl)-N'-(1H-imidazol-2-ylmethyl)-N'-(5,6,7,8-tetrahydro-8-quinolinyl)-1,4-benzenedimethanamine; N-(2-pyridinylmethyl)-N'-[(2-amino-3-phenyl)propyl]-N'-(5,6,7,8-tetrahydro-8-quinolinyl)-1,4-benzenedimethanamine; N-(2-pyridinylmethyl)-N'-(1H-imidazol-4-ylmethyl)-N'-(5,6,7,8-tetrahydro-8-quinolinyl)-1,4-benzenedimethanamine; N-(2-pyridinylmethyl)-N'-(2-quinolinylmethyl)-N'-(5,6,7,8-tetrahydro-8-quinolinyl)-1,4-benzenedimethanamine; N-(2-pyridinylmethyl)-N'-(2-(2-naphthoyl)aminoethyl)-N'-(5,6,7,8-tetrahydro-8-quinolinyl)-1,4-benzenedimethanamine; N-(2-pyridinylmethyl)-N'—[(S)-(2-acetylamino-3-phenyl)propyl]-N'-(5,6,7,8-tetrahydro-8-quinolinyl)-1,4-benzenedimethanamine; N-(2-pyridinylmethyl)-N'—[(S)-(2-acetylamino-3-phenyl)propyl]-N'-(5,6,7,8-tetrahydro-8-quinolinyl)-1,4-benzenedimethanamine; N-(2-pyridinylmethyl)-N'-[3-((2-naphthalenylmethyl)amino)propyl]-N'-(5,6,7,8-tetrahydro-8-quinolinyl)-1,4-benzenedimethanamine; N-(2-pyridinylmethyl)-N'-[2-(S)-pyrollidinylmethyl]-N'-(5,6,7,8-tetrahydro-8-quinolinyl)-1,4-benzenedimethanamine; N-(2-pyridinylmethyl)-N'-[2-(R)-pyrollidinylmethyl]-N'-(5,6,7,8-tetrahydro-8-quinolinyl)-1,4-benzenedimethanamine; N-(2-pyridinylmethyl)-N'-[3-pyrazolylmethyl]-N'-(5,6,7,8-tetrahydro-8-quinolinyl)-1,4-benzenedimethanamine; N-(2-pyridinylmethyl)-N'-[2-pyrrolylmethyl]-N'-(5,6,7,8-tetrahydro-8-quinolinyl)-1,4-benzenedimethanamine; N-(2-pyridinylmethyl)-N'-[2-thiopheneylmethyl]-N'-(5,6,7,8-tetrahydro-8-quinolinyl)-1,4-benzenedimethanamine N-(2-pyridinylmethyl)-N'-[2-thiazolylmethyl]-N'-(5,6,7,8-tetrahydro-8-quinolinyl)-1,4-benzenedimethanamine; N-(2-pyridinylmethyl)-N'-[2-furanylmethyl]-N'-(5,6,7,8-tetrahydro-8-quinolinyl)-1,4-benzenedimethanamine; N-(2-pyridinylmethyl)-N'-[2-[(phenylmethyl)amino]ethyl]-N'-(5,6,7,8-tetrahydro-8-quinolinyl)-1,4-benzenedimethanamine; N-(2-pyridinylmethyl)-N'-(2-aminoethyl)-N'-(5,6,7,8-tetrahydro-8-quinolinyl)-1,4-benzenedimethanamine; N-(2-pyridinylmethyl)-N'-3-pyrrolidinyl-N'-(5,6,7,8-tetrahydro-8-quinolinyl)-1,4-benzenedimethanamine N-(2-pyridinylmethyl)-N'-4-piperidinyl-N'-(5,6,7,8-tetrahydro-8-quinolinyl)-1,4-benzenedimethanamine; N-(2-pyridinylmethyl)-N'-[2-[(phenyl)amino]ethyl]-N'-(5,6,7,8-tetrahydro-8-quinolinyl)-1,4-benzenedimethanamine; N-(2-pyridinylmethyl)-N'-(7-methoxy-1,2,3,4-tetrahydro-2-naphthalenyl)-1,4-benzenedimethanamine; N-(2-pyridinylmethyl)-N'-(6-methoxy-1,2,3,4-tetrahydro-2-naphthalenyl)-1,4-benzenedimethanamine; N-(2-pyridinylmethyl)-N'-(1-methyl-1,2,3,4-tetrahydro-2-naphthalenyl)-1,4-benzenedimethanamine; N-(2-pyridinylmethyl)-N'-(7-methoxy-3,4-dihydronaphthalenyl)-1-(aminomethyl)-4-benzamide; N-(2-pyridinylmethyl)-N'-(6-methoxy-3,4-dihydronaphthalenyl)-1-(aminomethyl)-4-benzamide; N-(2-pyridinylmethyl)-N'-(1H-imidazol-2-ylmethyl)-N'-(7-methoxy-1,2,3,4-tetrahydro-2-naphthalenyl)-1,4-benzenedimethanamine; N-(2-pyridinylmethyl)-N'-(8-hydroxy-1,2,3,4-tetrahydro-2-naphthalenyl)-1,4-benzenedimethanamine; N-(2-pyridinylmethyl)-N'-(1H-imidazol-2-ylmethyl)-N'-(8-hydroxy-1,2,3,4-tetrahydro-2-naphthalenyl)-1,4-benzenedimethanamine; N-(2-pyridinylmethyl)-N'-(8-Fluoro-1,2,3,4-tetrahydro-2-naphthalenyl)-1,4-benzenedimethanamine; N-(2-pyridinylmethyl)-N'-(1H-imidazol-2-ylmethyl)-N'-(8-Fluoro-1,2,3,4-tetrahydro-2-naphthalenyl)-1,4-benzenedimethanamine; N-(2-pyridinylmethyl)-N'-(5,6,7,8-tetrahydro-7-quinolinyl)-1,4-benzenedimethanamine; N-(2-pyridinylmethyl)-N'-(1H-imidazol-2-ylmethyl)-N'-(5,6,7,8-tetrahydro-7-quinolinyl)-1,4-benzenedimethanamine; N-(2-pyridinylmethyl)-N'-[2-[(2-naphthalenylmethyl)amino]ethyl]-N'-(5,6,7,8-tetrahydro-8-quinolinyl)-1,4-benzenedimethanamine; N-(2-pyridinylmethyl)-N'-[2-(isobutylamino)ethyl]-N'-(5,6,7,8-tetrahydro-8-quinolinyl)-1,4-benzenedimethanamine; N-(2-pyridinylmethyl)-N'-[2-[(2-pyridinylmethyl)amino]ethyl]-N'-(5,6,7,8-tetrahydro-8-quinolinyl)-1,4-benzenedimethanamine; N-(2-pyridinylmethyl)-N'-[2-[(2-furanylmethyl)amino]ethyl]-N'-(5,6,7,8-ttrahydro-8-quinolinyl)-1,4-benzenedimethanamine; N-(2-pyridinylmethyl)-N'-(2-guanidinoethyl)-N'-(5,6,7,8-tetrahydro-8-quinolinyl)-1,4-benzenedimethanamine; N-(2-pyridinylmethyl)-N'-[2-[bis-[(2-methoxy)phenylmethyl]amino]ethyl]-N'-(5,6,7,8-tetrahydro-8-quinolinyl)-1,4-benzene dimethanamine; N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine; N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine; N-(2-pyridinylmethyl)-N'-[2-(phenylureido)ethyl]-N'-(5,6,7,8-tetrahydro-8-quinolinyl)-1,4-benzenedimethanamine; N-(2-pyridinylmethyl)-N'-[[N"-(n-butyl)carboxamido]methyl]-N'-(5,6,7,8-tetrahydro-8-quinolinyl)-1,4-benzenedimethanamine; N-(2-pyridinylmethyl)-N'-(carboxamidomethyl)-N'-(5,6,7,8-tetrahydro-8-quinolinyl)-1,4-benzenedimethanamine; N-(2-pyridinylmethyl)-N'—[(N"-phenyl)carboxamidomethyl]-N'-(5,6,7,8-tetrahydro-8-quinolinyl)-1,4-benzenedimethanamine; N-(2-pyridinylmethyl)-N'-(carboxymethyl)-N'-(5,6,7,8-tetrahydro-8-quinolinyl)-1,4-benzenedimethanamine; N-(2-pyridinylmethyl)-N'-(phenylmethyl)-N'-(5,6,7,8-tetrahydro-8-quinolinyl)-1,4-benzenedimethanamine; N-(2-pyridinylmethyl)-N'-(1H-benzimidazol-2-ylmethyl)-N'-(5,6,7,8-tetrahydro-8-quinolinyl)-1,4-benzenedimethanamine; N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt); N-(2-pyridinylmethyl)-N'-(5-nitro-1H-benzimidazol-2-ylmethyl)-N'-(5,6,7,8-tetrahydro-8-quinolinyl)-1,4-benzenedimethanamine; N-(2-pyridinylmethyl)-N''—[(1H)-5-azabenzimidazol-2-ylmethyl]-N'-(5,6,7,8-tetrahydro-8-quinolinyl)-1,4-benzenedimethanamine; N-(2-pyridinylmethyl)-N-(4-phenyl-1H-imidazol-2-ylmethyl)-N'-(5,6,7,8-tetrahydro-8-quinolinyl)-1,4-benzenedimethanamine; N-(2-pyridinylmethyl)-N'-[2-(2-pyridinypethyl]-N'-(5,6,7,8-tetrahydro-8-quinolinyl)-1,4-benzenedimethanamine; N-(2-pyridinylmethyl)-N'-(2-benzoxazolyl)-N'-(5,6,7,8-tetra hydro-8-quinolinyl)-1,4-benzenedimethanamine; N-(2-pyridinylmethyl)-N'-(trans-2-aminocyclohexyl)-N'-(5,6,7,8-tetrahydro-8-quinolinyl)-1,4-benzenedimethanamine; N-(2-pyridinylmethyl)-N'-(2-phenylethyl)-N'-(5,6,7,8-tetrahydro-8-quinolinyl)-1,4-benzenedimethanamine; N-(2-pyridinylmethyl)-N'-(3-phenylpropyl)-N'-(5,6,7,8-tetrahydro-8-quinolinyl)-1,4-benzenedimethanamine; N-(2-pyridinylmethyl)-N'-(trans-2-aminocyclopentyl)-N'-(5,6,7,8-tetrahydro-8-quinolinyl)-1,4-benzenedimethanamine; N-[[4-[[(2-pyridinylmethyl)amino]methyl]phenyl]methyl]-N-(5,6,7,8-tetrahydro-8-quinolinyl)-glycinamide; N-[[4-[[(2-pyridinylmethyl)amino]methyl]phenyl]methyl]-N-(5,6,7,8-tetrahydro-8-quinolinyl)-(L)-alaninamide; N-[[4-[[(2-pyridinylmethyl)amino]methyl]phenyl]methyl]-N-(5,6,7,8-tetrahydro-8-quinolinyl)-(L)-aspartamide; N-[[4-[[(2-pyridinylmethyl)amino]methyl]phenyl]methyl]-N-(5,6,7,8-tetrahydro-8-quinolinyl)-pyrazinamide; N-[[4-[[(2-pyridinylmethy)amino]methyl]phenyl]methyl]-N-(5,6,7,8-tetrahydro-8-quinolinyl)-(L)-prolinamide; N-[[4-[[(2-pyridinylmethyl)amino]methyl]phenyl]methyl]-N-(5,6,7,8-tetrahydro-8-quinolinyl)-(L)-lysinamide; N-[[4-[[(2-pyridinylmethyl)amino]methyl]phenyl]methyl]-N-(5,6,7,8-tetrahydro-8-quinolinyl)-benzamide; N-[[4-[[(2-pyridinylmethyl)amino]methyl]phenyl]methyl]-N-(5,6,7,8-tetrahydro-8-quinolinyl)-picolinamide; N'-Benzyl-N-[[4-[[(2-pyridinylmethyl) amino]methyl]phenyl]methyl]-N-(5,6,7,8-tetrahydro-8-quinolinyl)-urea; N'-phenyl-N-[[4-[[(2-pyridinylmethyl) amino]methyl]phenyl]methyl]-N-(5,6,7,8-tetrahydro-8-quinolinyl)-urea; N-(6,7,8,9-tetrahydro-5H-cyclohepta[bacteriapyridin-9-yl)-4-[[(2-pyridinylmethyl)amino]methyl]benzamide; N-(5,6,7,8-tetrahydro-8-quinolinyl 4[[(2-pyridinylmethyl)amino]methyl]benzamide; N,N'-bis(2-pyridinylmethyl)-N'-(5,6,7,8-tetrahydro-8-quinolinyl)-1,4-benzenedimethanamine; N,N'-bis(2-pyridinylmethyl)-N'-(6,7,8,9-tetrahydro-5H-cyclohepta[bacteriapyridin-9-yl)-1,4-benzenedimethanamine; N,N'-bis(2-pyridinylmethyl)-N'-(6,7-dihydro-5H-cyclopenta[bacteriapyridin-7-yl)-1,4-benzenedimethanamine; N,N'-bis(2-pyridinylmethyl)-N'-(1,2,3,4-tetrahydro-1-naphthalenyl)-1,4-benzenedimethanamine; N,N'-bis(2-pyridinylmethyl)-N'-[(5,6,7,8-tetrahydro-8-quinolinyl)methyl]-1,4-benzenedimethanamine; N,N'-bis(2-pyridinylmethyl)-N'[(6,7-dihydro-5H-cyclopenta[bacteriapyridin-7-yl)methyl]-1,4-benzenedimethanamine; N-(2-pyridinylmethyl)-N-(2-methoxyethyl)-N'-(5,6,7,8-tetrahydro-8-quinolinyl)-1,4-benzenedimethanamine; N-(2-pyridinylmethyl)-N-[2-(4-methoxyphenyl)ethyl]-N'-(5,6,7,8-tetrahydr-8-quinolinyl)-1,4-benzenedimethanamine; N,N'-bis(2-pyridinylmethyl)-1,4-(5,6,7,8-tetrahydro-8-quinolinyl)benzenedimethanamine; N-[(2,3-dimethoxyphenyl)methyl]-N'-(2-pyridinylmethyl)-N-(5,6,7,8-tetrahydro-8-quinolinyl)-1,4-benzenedimethanamine; N,N'-bis(2-pyridinylmethyl)-N-[1-(N"-phenyl-N"-methylureido)-4-piperidinyl]-1,3-benzenedimethanamine; N,N'-bis(2- pyridinylmethyl)-N—[N'''-p-toluenesulfonylphenylalanyl)-4-piperidinyl]-1,3-benzenedimethanamine; N,N'-bis(2-pyridinylmethyl)-N-[1-[3-(2-chlorophenyl)-5-methyl-isoxazol-4-oyl]-4-piperidinyl]-1,3-benzenedimethanamine; N-[(2-hydroxyphenyl)methyl]-N'-(2-pyridinylmethyl)-N-(6,7,8,9-tetrahydro-5H-cyclohepta[bacteriapyridin-9-yl)-1,4-benzenedimethanamine; N-[(4-cyanophenyl)methyl]-N'-(2-pyridinylmethyl)-N-(6,7,8,9-tetrahydro-5H-cyclohepta[bacteriapyridin-9-yl)-1,4-benzenedimethanamine; N-[(4-cyanophenyl)methyl]-N'-(2-pyridinylmethyl)-N-(5,6,7,8-tetrahydro-8quinolinyl)-1,4-benzenedimethanamine; N-[(4-acetamidophenyl)methyl]-N'-(2-pyridinylmethyl)-N-(5,6,7,8-tetrahydro-8-quinolinyl)-1,4-benzenedimethanamine; N-[(4-phenoxyphenyl)methyl]-N'-(2-pyridinylmethyl)-N-(6,7,8,9-tetrahydro-5H-cyclohepta[bacteriapyridin-9-yl)-1,4-benzenedimethanamine; N-[(1-methyl-2-carboxamido)ethyl]-N,N'-bis(2-pyridinylmethyl)-1,3-benzenedimethanamine; N-[(4-benzyloxyphenyl)methyl]-N'-(2-pyridinylmethyl)-N-(6,7,8,9-tetrahydro-5H-cyclohepta[bacteriapyridin-9-yl)-1,4-benzenedimethanamine; N-[(thiophene-2-yl)methyl]-N'-(2-pyridinylmethyl)-N-(6,7,8,9-tetrahydro-5-H-cyclohepta[bacteriapyridin-9-yl)-1,4-benzenedimethanamine; N-[1-(benzyl)-3-pyrrolidinyl]-N,N'-bis(2-pyridinylmethyl)-1,3-benzenedimethanamine; N-[1-methyl-3-(pyrazol-3-yl)]propyl]-N,N'-bis(2-pyridinylmethyl)-1,3-benzenedimethanamine; N-[1-(phenyl)ethyl]-N,N'-bis(2-pyridinylmethyl)-1,3-benzenedimethanamine; N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine; N-[1-benzyl-3-carboxymethyl-4-piperidinyl]-N,N'-bis(2-pyridinylmethyl)-1,3-benzenedimethanamine; N-[(3,4-methylenedioxyphenyl)methyl]-N'-(2-pyridinylmethyl)-N-(5,6,7,8-tetrahydro-8-quinolinyl)-1,4-benzenedimethanamine; N-(3-pyridinylmethyl)-N'-(2-pyridinylmethyl)-N-(6,7,8,9-tetrahydro-5H-cyclohepta[b]pyridin-9-yl)-1,4-benzenedimethanamine; N-[[1-methyl-2-(2-tolyl)carboxamido]ethyl]-N,N'-bis(2-pyridinylmethyl)-13-benzenedimethanamine; N-[(1,5-dimethyl-2-phenyl-3-pyrazolinone-4-yl)methyl]-N'-(2-pyridinylmethyl)-N-(5,6,7,8-tetrahydro-8-quinolinyl)-1,4-benzenedimethanamine; N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine; N-(1-phenyl-3,5-dimethylpyrazolin-4-ylmethyl)-N'-(2-pyridinylmethyl)-N-(5,6,7,8-tetrahydro-8-quinolinyl)-1,4-benzenedimethanamine; N-[1H-imidazol-4-ylmethyl]-N,N'-bis(2-pyridinylmethyl)-1,3-benzenedimethanamine; N-[(3-methoxy-4,5-methylenedioxyphenyl)methyl]-N'-(2-pyridinylmethyl)-N-(6,7,8,9-tetrahydro-5H-cyclohepta[b]pyridin-9-yl)-1,4-benzenedimethanamine; N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine; N-[(3-cyanophenyl)methyl]-N'-(2-pyridinylmethyl)-N-(5,6,7,8-tetrahydro-8-quinolinyl)-1,4-benzenedimethanamine; N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine; N-(5-ethylthiophene-2-ylmethyl)-N'-(2-pyridinylmethyl)-N-(5,6,7,8-tetrahydro-8-quinolinyl)-1,4-benzenedimethanamine; N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine; N-[(2,6-difluorophenyl)methyl]-N'-(2-pyridinylmethyl)-N-(5,6,7,8-tetrahydro-8-quinolinyl)-1,4-benzenedimethanamine; N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine; N-(2-difluoromethoxyphenylmethyl)-N'-(2-pyridinylmethyl)-N-(5,6,7,8-tetrahydro-8-quinolinyl)-1,4-benzenedimethanamine; N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine; N,N'-bis(2-pyridinylmethyl)-N-[1-(N'''-phenyl-N'''-methylureido)-4-piperidinyl]-1,4-benzenedimethanamine; N,N'-bis(2-pyridinylmethyl)-N—[N'''-p-toluenesulfonylphenylalanyl)-4-piperidinyl]-1,4-benzenedimethanamine; N-[1-(3-pyridinecarboxamido)-4-piperidinyl]-N,N'-bis(2-pyridinylmethyl)-1,4-benzenedimethanamine; N-[1-(cyclopropylcarboxamido)-4-piperidinyl]-N,N'-bis(2-pyridinylmethyl)-1,4-benzenedimethanamine; N-[1-(1-phenylcyclopropylcarboxamido)-4-piperidinyl]-N,N'-bis(2-pyridinylmethyl)-1,4-benzenedimethanamine; N-(1,4-benzodioxan-6-ylmethyl)-N'-(2-pyridinylmethyl)-N-(5,6,7,8-tetrahydro-8-quinolinyl)-1,4-benzenedimethanamine; N-[1-[3-(2-chlorophenyl)-5-methyl-isoxazol-4-carboxamido]-4-piperidinyl]-N,N'-bis(2-pyridinylmethyl)-1,4-benzenedimethanamine; N-[1-(2-thiomethylpyridine-3-carboxamido)-4-piperidinyl]-N,N'-bis(2-pyridinylmethyl)-1,4-benzenedimethanamine; N-[(2,4-difluorophenyl)methyl]-N'-(2-pyridinylmethyl)-N-(5,6,7,8-tetrahydro-8-quinolinyl)-1,4-benzenedimethanamine; N-(1-methylpyrrol-2-ylmethyl)-N'-(2-pyridinylmethyl)-N-(5,6,7,8-tetrahydro-8-quinolinyl)-1,4-benzenedimethanamine; N-[(2-hydroxyphenyl)methyl]-N'-(2-pyridinylmethyl)-N-(5,6,7,8-tetrahydro-8-quinolinyl)-1,4-benzenedimethanamine; N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine; N-(3-pyridinylmethyl)-N'-(2-pyridinylmethyl)-N-(5,6,7,8-tetrahydro-8-quinolinyl)-1,4-benzenedimethanamine; N-[2-(N'''-morpholinomethyl)-1-cyclopentyl]-N,N'-bis(2-pyridinylmethyl)-1,4-benzenedimethanamine; N-[(1-methyl-3-piperidinyl)propyl]-N,N'-bis(2-pyridinylmethyl)-1,4-benzenedimethanamine; N-(1-methylbenzimidazol-2-ylmethyl)-N'-(2-pyridinylmethyl)-N-(5,6,7,8-tetrahydro-8-quinolinyl)-1,4-benzenedimethanamine; N-[1-(benzyl)-3-pyrrolidinyl]-N,N'-bis(2-pyridinylmethyl)-1,4-benzenedimethanamine; N-[[(1-phenyl-3-(N'''-morpholino)]propyl]-N,N'-bis(2-pyridinylmethyl)-1,4-benzenedimethanamine; N-[1-(iso-propyl)-4-piperidinyl]-N,N'-bis(2-pyridinylmethyl)-1,4-benzenedimethanamine; N-[1-(ethoxycarbonyl)-4-piperidinyl]-N'-(2-pyridinylmethyl)-N-(5,6,7,8-tetrahydro-8-quinolinyl)-1,4-benzenedimethanamine; N-[(1-methyl-3-pyrazolyl)propyl]-N'-(2-pyridinylmethyl)-N-(5,6,7,8-tetrahydro-8-quinolinyl)-1,4-benzenedimethanamine; N-[1-methyl-2-(N'''M'''-diethylcarboxamido)ethyl]-N,N'-bis(2-pyridinylmethyl)-1,4-benzenedimethanamine; N-[(1-methyl-2-phenylsulfonyl)ethyl]-N'-(2-pyridinylmethyl)-N-(5,6,7,8-tetrahydro-8-quinolinyl)-1,4-benzenedimethanamine; N-[(2-chloro-4,5-methylenedioxyphenyl)methyl]-N'-(2-pyridinylmethyl)-N-(5,6,7,8-tetrahydro-8-quinolinyl)-1,4-benzenedimethanamine; N-[1-methyl-2-[N'''-(4-chlorophenyl)carboxamido]ethyl]-N'-(2-pyridinylmethyl)-N-(5,6,7,8-tetrahydro-8-quinolinyl)-1,4-benzenedimethanamine; N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine; N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine; N-(3-quinolylmethyl)-N'-(2-pyridinylmethyl)-N-(5,6,7,8- tetrahydro-8-quinolinyl)-1,4-benzenedimethanamine; N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine; N-(2-quinolylmethyl)-N'-(2-pyridinylmethyl)-N-(6,7,8,9-tetrahydro-5H-cyclohepta[b]pyridin-9-yl)-1,4-benzenedimethanamine; N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine; N-[1H-imidazol-2-ylmethyl]-N,N'-bis(2-pyridinylmethyl)-1,4-benzenedimethanamine; N-(3-quinolylmethyl)-N'-(2-pyridinylmethyl)-N-(6,7,8,9-tetrahydro-5H-cyclohepta[b]pyridin-9-yl)-1,4-benzenedimethanamine; N-(2-thiazolylmethyl)-N'-(2-pyridinylmethyl)-N-(6,7,8,9-tetrahydro-5H-cyclohepta[b]pyridin-9-yl)-1,4-benzenedimethanamine; N-(4-pyridinylmethyl)-N'-(2-pyridinylmethyl)-N-(6,7,8,9-tetrahydro-5H-cyclohepta[b]pyridin-9-yl)-1,4-benzenedimethanamine; N-[(5-benzyloxy)benzo[b]pyrrol-3-ylmethyl]-N,N'-bis(2-pyridinylmethyl)-1,4-benzenedimethanamine; N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine; N-[(4-methyl)-1H-imidazol-5-ylmethyl]-N,N'-bis(2-pyridinylmethyl)-1,4-benzenedimethanamine; N-[[(4-dimethylamino)-1-napthalenyl]methyl]-N,N'-bis(2-pyridinylmethyl)-1,4-benzenedimethanamine; N-[1,5-dimethyl-2-phenyl-3-pyrazolinone-4-ylmethyl]-N,N'-bis(2-pyridinylmethyl)-1,4-benzenedimethanamine; N-[1-[(1-acetyl-2-(R)-prolinyl]-4-piperidinyl]-N-[2-(2-pyridinypethyl]-N'-(2-pyridinylmethyl)-1,3-benzenedimethanamine; N-[1-[2-acetamidobenzoyl-4-piperidinyl]-4-piperidinyl]-N-[2-(2-pyridinypethyl]-N'-(2-pyridinylmethyl)-1,3-benzenedimethanamine; N-[(2-cyano-2-phenyl)ethyl]-N'-(2-pyridinylmethyl)-N-(6,7,8,9-tetrahydro5H-cyclohepta[b]pyridin-9-yl)-1,4-benzenedimethanamine; N—[(N"-acetyltryptophanyl)-4-piperidinyl]-N-[2-(2-pyridinypethyl]-N'-(2-pyridinylmethyl)-1,3-benzenedimethanamine; N—[(N"-benzoylvalinyl)-4-piperidinyl]-N-[2-(2-pyridinypethyl]-N'-(2-pyridinylmethyl)-1,3-benzenedimethanamine; N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine; N-(4-pyridinylmethyl)-N'-(2-pyridinylmethyl)-N-(5,6,7,8-tetrahydro-8-quinolinyl)-1,4-benzenedimethanamine; N-(1-methylbenzimadazol-2-ylmethyl)-N'-(2-pyridinylmethyl)-N-(6,7,8,9-tet-rahydro-5H-cyclohepta[b]pyridin-9-yl)-1,4-benzenedimethanamine; N-[1-butyl-4-piperidinyl]-N-[2-(2-pyridinypethyl]-N'-(2-pyridinylmethyl)-1,3-benzenedimethanamine; N-[1-benzoyl-4-piperidinyl]-N-[2-(2-pyridinyl)ethyl]-N'-(2-pyridinylmethyl)-1,3-benzenedimethanamine; N-[1-(benzyl)-3-pyrrolidinyl]-N-[2-(2-pyridinypethyl]-N'-(2-pyridinylmethyl)-1,3-benzenedimethanamine; N-[(1-methyl)benzo[b]pyrrol-3-ylmethyl]-N-[2-(2-pyridinyl)ethyl]-N'-(2-pyridinylmethyl)-1,3-benzenedimethanamine; N-[1H-imidazol-4-ylmethyl]-N-[2-(2-pyridinypethyl]-N'-(2-pyridinylmethyl)-1,3-benzenedimethanamine; N-[1-(benzyl)-4-piperidinyl]-N-[2-(2-pyridinypethyl]-N'-(2-pyridinylmethyl)-1,4-benzenedimethanamine; N-[1-methylbenzimidazol-2-ylmethyl]-N-[2-(2-pyridinypethyl]-N'-(2-pyridinylmethyl)-1,4-benzenedimethanamine; N-[(2-phenyl)benzo[b]pyrrol-3-ylmethyl]-N-[2-(2-pyridinypethyl]-N'-(2-pyridinylmethyl)-1,4-benzenedimethanamine; N-[(6-methylpyridin-2-yl)methyl]-N'-(2-pyridinylmethyl)-N-(5,6,7,8-tetrahydro-8-quinolinyl)-1,4-benzenedimethanamine; N-(3-methyl-1H-pyrazol-5-ylmethyl)-N'-(2-pyridinylmethyl)-N-(5,6,7,8-tetrahydro-8-quinolinyl)-1,3-benzenedimethanamine; N-[(2-methoxyphenyl)methyl]-N'-(2-pyridinylmethyl)-N-(5,6,7,8-tetrahydro-8-quinolinyl)-1,3-benzenedimethanamine; N-[(2-ethoxyphenyl)methyl]-N'-(2-pyridinylmethyl)-N-(6,7,8,9-tetrahydro-5-H-cyclohepta[b]pyridin-9-yl)-1,3-benzenedimethanamine; N-(benzyloxyethyl)-N'-(2-pyridinylmethyl)-N-(5,6,7,8-tetrahydro-8-quinolinyl)-1,3-benzenedimethanamine; N-[(2-ethoxy-1-naphthalenyl)methyl]-N'-(2-pyridinylmethyl)-N-(5,6,7,8-tetrahydro-8-quinolinyl)-1,3-benzenedimethanamine; N-[(6-methylpyridin-2-yl)methyl]-N'-(2-pyridinylmethyl)-N-(5,6,7,8-tetrahydro-8-quinolinyl)-1,3-benzenedimethanamine; 1-[[4-[[(2-pyridinylmethyl)amino]methyl]phenyl]methyl]guanidine; N-(2-pyridinylmethyl)-N-(8-methyl-8-azabicyclo[3.2.1]octan-3-yl)-1,4-benzenedimethanamine; 1-[[4-[[(2-pyridinylmethyl)amino]methyl]phenyl]methyl]homopiperazine; 1-[[3-[[(2-pyridinylmethyl)amino]methyl]phenyl]methyl]homopiperazine; trans and cis-1-[[4-[[(2-pyridinylmethyl)amino]methyl]phenyl]methyl]-3,5-piperidinediamine; N,N'-[1,4-Phenylenebis(methylene)]bis-4-(2-pyrimidyl)piperazine; 1-[[4-[[(2-pyridinylmethyl)amino]methyl]phenyl]methyl]-1-(2-pyridinyl)methylamine; 2-(2-pyridinyl)-5-[[(2-pyridinylmethyl)amino]methyl]-1,2,3,4-tetrahydroisoquinoline; 1-[[4-[[(2-pyridinylmethyl)amino]methyl]phenyl]methyl]-3,4-diaminopyrrolidine; 1-[[4-[[(2-pyridinylmethyl)amino]methyl]phenyl]methyl]-3,4-diacetylaminopyrrolidine; 8-[[4-[[(2-pyridinylmethyl)amino]methyl]phenyl]methyl]-2,5,8-triaza-3-oxabicyclo[4.3.0]nonane; and 8-[[4-[[(2-pyridinylmethyl)amino]methyl]phenyl]methyl]-2,5,8-triaza bicyclo[4.3.0]nonane.

Still other embodiments of small molecule CXCR4 antagonists include compounds disclosed in U.S. Pat. Appl. Pub. No. 20120101280, which is expressly incorporated herein by reference in its entirety. In some embodiments of the disclosed compounds, the compounds have a spiro-bound coupling group as represented by formula (VII):

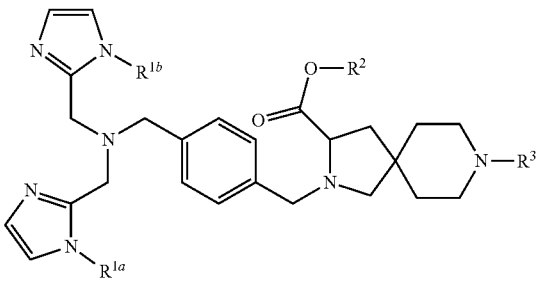

(VII)

wherein:
wherein $R^{1a}$ and $R^{1b}$ each independently represents a hydrogen atom or a C1-4 alkyl group, $R^3$ represents a C3-8 branched-chain alkyl group or a C5-6 cycloalkyl group, and $R_2$ represents a hydrogen atom or a C1-4 alkyl group, a salt thereof, an N-oxide thereof, or a solvate thereof In some embodiments, $R^2$ is a hydrogen atom; $R^{1a}$ is a hydrogen atom, and also Rib is a hydrogen atom or a methyl group; $R^3$ is a 1-ethylpropyl, 2,2-dimethylpropyl, 2-methylpropyl or cyclohexyl group; or a combination of these.

In specific embodiments, the compounds represented by formula (VII) are selected from: (1) 2-(4-{[bis(1H-imidazol-2-ylmethyl)amino]methyl}benzyl)-8-(1-ethylpropyl)-2,8-diazaspiro[4.5]decane-3-carboxylic acid, (2) 8-(1-ethylpropyl)-2-[4-({(1H-imidazol-2-ylmethyl)[(1-methyl-1H- imidazol-2-yl)methyl]amino}methyl)benzyl]-2,8-diazaspiro[4.5]decane-3-carboxylic acid, (3) (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid, (4) (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid, (5) (3R)-2-(4-{[bis(1H-imidazol-2-ylmethyl)amino]methyl}benzyl)-8-(1-ethylpropyl)-2,8-diazaspiro[4.5]decane-3-carboxylic acid, or (6) (3S)-2-(4-{[bis(1H-imidazol-2-ylmethyl)amino]methyl}benzyl)-8-(1-ethylpropyl)-2,8-diazaspiro[4.5]decane-3-carboxylic acid.

Illustrative examples of CXCR4 antagonists include Mozobil (Plerixafor) (AnorMED Inc.), AMD-070 (AnorMED Inc.), BKT140 (Biokine Therapeutics Inc.), CXCR4 monoclonal antibody (Northwest Biotherapeutics Inc.), KRH-2731/CS-3955 (Daiichi Sankyo Company), AVR 118 (reticulose) (Advanced Viral Research Corp.), CXCR4 antagonist (TaiGen Biotechnology), POL5551 (Polyphor Ltd., Switzerland) and CTCE-0214 (Chemokine Therapeutics Corp). In specific embodiments, at least two different mobilizers are used in combination with the C3aR antagonist (e.g., a CXCR4 antagonist, an illustrative example of which is Plerixafor and a colony stimulating factor, an illustrative example of which is G-CSF).

4. Therapeutic and Prophylactic Uses

In accordance with the present invention, it is proposed that C3aR antagonists and mobilizers of hematopoietic stem cells and/or progenitor cells are useful as active agents for stimulating or enhancing the development, mobilization, proliferation and/or differentiation of a neutrophil-containing leukocyte population that inhibits growth and/or metastasis of a tumor, for reducing incidence of a hyperproliferative cell disorder, for reducing recurrence of a hyperproliferative disorder, or for treating or preventing a hyperproliferative cell disorder. Thus, a C3aR antagonist can be administered to an individual in combination (e.g., in the same composition or in separate compositions) with a mobilizer ("combination therapy"), and optionally with a pharmaceutically acceptable carrier, to stimulate or enhance the development, mobilization, proliferation and/or differentiation of a neutrophil-containing leukocyte population that inhibits growth and/or metastasis of a tumor, including increasing the number of hematopoietic stem cells, progenitor cells and granulocytes, which increase the number of anti-tumorigenic neutrophils in a patient, to reduce the incidence of a hyperproliferative cell disorder, to reduce recurrence of a hyperproliferative disorder, to treat or prevent a hyperproliferative cell disorder.

The dosages of C3aR antagonist and the mobilizer to be administered may depend on the subject to be treated inclusive of the age, sex, weight and general health condition thereof. The dosages will also take into consideration the binding affinity or modulatory activity of the C3aR antagonist to its target molecule, the hematopoietic capacity of the mobilizer(s), their bioavailability and their in vivo and pharmacokinetic properties. In this regard, precise amounts of the agents for administration can also depend on the judgment of the practitioner. In determining the effective amount of the agents to be administered in the treatment of a hyperproliferative cell disorder, the physician or veterinarian may evaluate the progression of the disease or condition over time. In any event, those of skill in the art may readily determine suitable dosages of the agents of the invention without undue experimentation. The dosage of the active agents administered to a patient should be sufficient to effect a beneficial response in the patient over time such as impairment or abrogation in the proliferation, migration, invasion, survival or viability of hyperproliferative cells such as tumor cells and/or in the treatment and/or prevention of a hyperproliferative cell disorder. The dosages may be administered at suitable intervals to stimulate or enhance the development, mobilization, proliferation and/or differentiation of a neutrophil-containing leukocyte population and/or ameliorate the symptoms of the hyperproliferative cell disorder. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

Dosage amount and interval may be adjusted individually to provide plasma levels of the active agent which are sufficient to maintain C3aR antagonist effects and hematopoietic function enhancing effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day. Animal testing of effective doses for treatment of particular disorders will provide further predictive indication of human dosage. Various considerations are described, e.g., in Gilman et al., (eds.) (1990) Goodman and Gilman's: The Pharmacological Bases of Therapeutics, 8th Ed., Pergamon Press, and Remington's Pharmaceutical Sciences, 17th ed. (1990), Mack Publishing Co., Easton, Pa. Methods for administration are discussed therein, e.g., for oral, intravenous, intraperitoneal, or intramuscular administration, transdermal diffusion, and others. Pharmaceutically acceptable carriers will generally include water, saline, buffers, drug delivery systems such as nanoparticles, hydrogels, microspheres, liposomes, dendrimers, polymers, micelles and/or other compounds described, e.g., in Remington: The Science and Practice of Pharmacy, 22$^{nd}$ Edition, 2012, Pharmaceutical Press, London, and/or in the Merck Index, Merck & Co., Rahway, N.J.

Thus, the C3aR antagonist and the mobilizer may be provided in effective amounts to stimulate or enhance the development, mobilization, proliferation and/or differentiation of an anti-tumor neutrophil-containing leukocyte population, to reduce the incidence of a hyperproliferative cell disorder, to reduce recurrence of a hyperproliferative disorder, to treat or prevent a hyperproliferative cell disorder. This process may involve administering the C3aR antagonist separately, simultaneously or sequentially with the mobilizer. In some embodiments, this may be achieved by administering a single composition or pharmacological formulation that includes both types of agent, or by administering two separate compositions or formulations at the same time, wherein one composition includes the C3aR antagonist and the other, the mobilizer. In other embodiments, the treatment with the C3aR antagonist may precede or follow the treatment with the mobilizer by intervals ranging from minutes to days. In embodiments where the C3aR antagonist is applied separately to the mobilizer, one would generally ensure that a significant period of time did not expire between the time of each delivery, such that the C3aR antagonist would still be able to exert an advantageously combined effect on stimulating or enhancing the development, mobilization, proliferation and/or differentiation of an anti-tumor neutrophil-containing leukocyte population, in particular, to maintain or enhance a subject's capacity to to reduce the incidence of a hyperproliferative cell disorder, to reduce recurrence of a hyperproliferative disorder, to treat or prevent a hyperproliferative cell disorder. In such instances, it is contemplated that one would administer both modalities within about 1-12 hours of each other and, more suitably, within about 2-6 hours of each other. In some situations, it may be desirable to extend the time period for treatment significantly, however, where several hours (2, 3, 4, 5, 6 or 7) to several days (1, 2, 3, 4, 5, 6, 7 or 8) lapse between the respective administrations.

It is conceivable that more than one administration of either the C3aR antagonist or mobilizer will be desired. Various combinations may be employed, where the C3aR antagonist is "A" and the mobilizer is "B", as exemplified below:

A/B/A B/A/B B/B/A A/A/B B/A/A A/B/B B/B/B/A B/B/ A/B A/A/B/B A/B/A/B A/B/B/A B/B/A/A B/A/B/A B/A/ A/B B/B/B/A A/A/A/B B/A/A/A A/B/A/A A/A/B/A A/B/ B/B B/A/B/B B/B/A/B.

Other combinations are contemplated. Again, both agents are delivered to a subject's immune system in a combined amount effective to stimulate or enhance the development, mobilization, proliferation and/or differentiation of an anti-tumor neutrophil-containing leukocyte population.

The C3aR antagonist and the mobilizer may be administered directly to a subject or it may be desirable to conjugate one or both to carrier proteins such as ovalbumin or serum albumin prior to administration. While it is possible for the active agent to be administered alone, it is generally desirable to present it as a pharmaceutical composition. Such compositions typically comprise at least one active agent or ingredient, together with one or more acceptable carriers. Each carrier should be both pharmaceutically and physiologically acceptable in the sense of being compatible with the other ingredients and not injurious to the patient. Compositions include those suitable for oral, rectal, nasal, topical, or parenteral (including subcutaneous, intramuscular, intravenous and intradermal) administration. The compositions may conveniently be presented in unit dosage form and may be prepared by many methods well known in the art of pharmacy. See, e.g., Gilman, et al. (eds.) (1990) Goodman and Gilman's: The Pharmacological Bases of Therapeutics, 8th Ed., Pergamon Press; and Remington's Pharmaceutical Sciences, 17th ed. (1990), Mack Publishing Co., Easton, Pa.; Avis, et al. (eds.) (1993) Pharmaceutical Dosage Forms, Parenteral Medications Dekker, N.Y.; Lieberman, et al. (eds.) (1990) Pharmaceutical Dosage Forms: Tablets Dekker, N.Y.; and Lieberman, et al. (eds.) (1990) Pharmaceutical Dosage Forms: Disperse Systems Dekker, N.Y. The methods of the invention may be combined with or used in association with other therapeutic agents.

In some embodiments, blood containing mobilized HSPC is collected from a donor by means well known in the art, suitably by apheresis, and the mobilized HSPC treated with C3aR antagonist before infusing a recipient with the treated HSPC and cells differentiated therefrom. In order to ensure capture of a repopulating quantity of cells, it is generally desirable to collect the donor's blood when the levels of mobilized HSPCs peak. In order to optimize the number of HSPCs harvested from mobilized blood, the levels HSPCs can be monitored by methods well known to those of skill in the art, and collection timed to coincide with HSPC peaks.

If desired, the donor cells can be enriched ex vivo by treating them with factors that stimulate the TNFα and GM-CSF receptors. Alternatively, or in addition, factors that stimulate FLT3 and the G-CSF receptor, such as FL and G-CSF, may be used. More particularly, hematopoietic tissues such as bone marrow and blood can be harvested from a donor by methods well known to those skilled in the art, and treated with TNFα, GM-CSF, FL, SCF, IL-7, IL-12, and G-CSF, either singularly or in combination, to enrich selectively for HSPCs. Prior to harvesting the hematopoietic tissue, the donor may be treated with cytokines to increase the yield of hematopoietic cells, such as TNFα, GM-CSF, FL, and G-CSF, but no pre-treatment is required. At a minimum, the starting cell population must contain HSPCs.

The cells harvested from the donor may be cultured ex vivo for several days in medium supplemented with TNFα, GM-CSF, FL, SCF, IL-7, IL-12, and G-CSF, either singularly or in combination. The concentration of GM-CSF administered would typically be in the range of 1,000 U/mL. In an alternative embodiment, TNFα may be administered, typically at a concentration of 200 U/mL. Appropriate concentrations of G-CSF, SCF, IL-7, IL-12, and FL can be readily determined by those of skill in the art, as by titration experiments or by reference to the working examples provided herein.

In some applications, it may be desirable to treat the cultured cells to remove graft versus host disease (GVHD) causing cells, using routine methods known in the art, as for example discussed below. The enriched HSPCs may then be selectively collected from the culture using techniques known to those of skill in the art, as for example discussed below.

In order to ensure enrichment of HSPCs to a repopulating quantity, it is generally desirable to collect the cultured cells when the levels of HSPCs peak. As with in vivo mobilization, ex vivo enrichment of cultured hematopoietic cells produces peak levels of HSPCs on different days depending on the cytokine administration protocol used. In order to optimize the number of HSPCs collected from cultured cells, the levels of HSPCs can be monitored by methods well known to those of skill in the art, and collection timed to coincide with HSPCs peaks.

Following collection, the HSPCs can be resuspended and administered to a recipient in the manner and quantity described for administration of mobilized HSPCs, as described for example below.

Once the HSPCs have been mobilized into a subject's peripheral blood or enriched in the cultured cells, they may be used as donor cells in the form of total white blood cells or peripheral blood mononuclear cells that comprise anti-tumorigenic leukocytes including anti-tumorigenic neutrophils, or selectively enriched by various methods which utilize specific antibodies which suitably bind specific markers to select those cells possessing or lacking various markers. These techniques may include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces, magnetic separations using antibody-coated magnetic beads, destructive separations such as antibody and complement or antibody bound to cytotoxins or radioactive isotopes.

If the mobilized blood is used for an autologous transplant, the peripheral blood mononuclear cells (PBMC) may be re-infused into the patient without modifications, with the exception that in the case of a cancer patient, the cell preparation is generally first purged of tumor cells. In contrast, if the mobilized blood is transferred into an allogeneic or xenogeneic recipient, the PBMC may first be depleted of GHVD-producing cells, leaving the HSPCs enriched in the PBMC population. In that connection, the PBMC may be treated with anti-αβTCR and anti-γδTCR antibodies to deplete T cells, anti-CD19 to deplete B cells and anti-CD56 to deplete NK cells. It is important to note that anti-Thy-1 antibodies should not be used to deplete GVHD producing cells, as they would deplete T cells and HSPC. Therefore, it is important to choose carefully the appropriate markers as targets for selecting the cells of interest and removing undesirable cell types.

Separation via antibodies for specific markers may be by negative or positive selection procedures. In negative separation, antibodies are used which are specific for markers present on undesired cells. Cells bound by an antibody may be removed or lysed and the remaining desired mixture retained. In positive separation, antibodies specific for markers present on the desired cells are used. Cells bound by the antibody are separated and retained. It will be understood that positive and negative separations may be used substantially simultaneously or in a sequential manner.

The most common technique for antibody based separation has been the use of flow cytometry such as by a FACS. Typically, separation by flow cytometry is performed as follows. The suspended mixture of hematopoietic cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through a FACS which separates the cells based on different fluorescence characteristics. FACS systems are available in varying levels of performance and ability, including multi-color analysis. The HSPCs can be identified by a characteristic profile of forward and side scatter which is influenced by size and granularity, as well as by positive and/or negative expression of certain cell surface markers.

Other separation techniques besides flow cytometry may provide for faster separations. One such method is biotin-avidin based separation by affinity chromatography. Typically, such a technique is performed by incubating the washed bone marrow with biotin-coupled antibodies to specific markers followed by passage through an avidin column. Biotin-antibody-cell complexes bind to the column via the biotin-avidin interaction, while other cells pass through the column. Finally, the column-bound cells may be released by perturbation or other methods. The specificity of the biotin-avidin system is well suited for rapid positive separation.

The HSPCs contained in enriched cell cultures or mobilized blood may be used in the form of total mononuclear cells, or partially purified or highly purified cell populations. If these cellular compositions are separate compositions, they are suitably administered simultaneously, but may be administered separately within a relatively close period of time. The mode of administration is generally but not limited to intravenous injection.

Once administered, it is believed that the cells home to various hematopoietic cell sites in the recipient's body, including bone marrow. The number of cells which should be administered is calculated for a specific species of recipient. For example, in rats, the T-cell depleted bone marrow component administered is typically between about $1 \times 10^7$ cells and $5 \times 10^7$ cells per recipient. In mice, the T-cell depleted bone marrow component administered is typically between about $1 \times 10^6$ cells and $5 \times 10^6$ cells per recipient. In humans, the T-cell depleted bone marrow component administered is typically between about $1 \times 10^8$ cells and $3 \times 10^8$ cells per kilogram body weight of recipient. For cross-species engraftment, larger numbers of cells may be required.

In mice, the number of HSPCs administered is suitably between about 100 and 300 HSPCs per recipient. In rats, the number of HSPCs administered is generally between about 600 and 1200 HSPCs per recipient. In humans, the number of HSPCs administered is suitably between about $1 \times 10^5$ and $1 \times 10^6$ HSC per recipient. The amount of the specific cells used will depend on many factors, including the condition of the recipient's health. In addition, co-administration of cells with various cytokines may further promote engraftment.

In addition to total body irradiation, a recipient may be conditioned by a medical treatment that results in immunosuppression and myeloablation or cytoreduction by the same techniques as are employed in substantially destroying a recipient's immune system, including, for example, irradiation, toxins, antibodies bound to toxins or radioactive isotopes, or some combination of these techniques. However, the level or amount of agents used is substantially smaller when immunosuppressing and cytoreducing than when substantially destroying the immune system. For example, substantially destroying a recipient's remaining immune system often involves lethally irradiating the recipient with 950 rads (R) of total body irradiation (TBI). This level of radiation is fairly constant no matter the species of the recipient. Consistent xenogeneic (ratmouse) chimerism has been achieved with 750 R TBI and consistent allogeneic (mouse) chimerism with 600R TBT. Chimerism was established by PB typing and tolerance confirmed by mixed lymphocyte reactions (MLR) and cytotoxic lymphocyte (CTL) response.

The mobilized blood and enriched cultured cells prepared in accordance with the present invention may be used for establishing both allogeneic chimerism and xenogeneic chimerism. Xenogeneic chimerism may be established when the donor and recipient as recited above are different species. Xenogeneic chimerism between rats and mice, between hamsters and mice, and between chimpanzees and baboons has been established. Xenogeneic chimerism between humans and other primates is also possible. Xenogeneic chimerism between humans and other mammals, such as pig, is equally viable.

It will be appreciated that, though the methods disclosed above involve one recipient and one donor, the present invention encompasses methods in which HSPCs from two donors are engrafted in a single recipient.

In some embodiments, the mobilized cells and enriched cultured cells prepared in this manner using inter alia the combination therapy of the present invention are useful not only in reestablishing a recipient's hematopoietic system but also in stimulation or enhancing the development, mobilization, proliferation and/or differentiation of an anti-tumor neutrophil-containing leukocyte population. In these embodiments, the recipient is subject to treatment methods that comprise destroying the recipient's immune system or immunosuppressing and myeloablating or cytoreducing the recipient's immune system, and then administering to the recipient syngeneic or autologous cell compositions comprising syngeneic or autologous purified HSPCs which are MHC-identical to the HSPCs of the recipient.

As noted above, the combination therapy of the present invention finds utility in the treatment or prophylaxis of hyperproliferative cell disorders in which a subject is exposed to a therapy or agent that inhibits the proliferation, survival or viability of a tumor, to thereby treat or prevent the hyperproliferative cell disorder. Representative therapies or agents of this type target rapidly dividing cells and/or disrupt the cell cycle or cell division. Accordingly, the present invention further contemplates combination therapies that employ both a therapy or treatment of this type together with administration of a C3aR antagonist and a mobilizer of hematopoietic stem cells and/or progenitor cells.

It is well known that chemotherapy and radiation therapy target rapidly dividing cells and/or disrupt the cell cycle or cell division. These treatments are offered as part of the treating several forms of cancer and autoimmune disease, aiming either at slowing their progression or reversing the symptoms of disease by means of a curative treatment. In some embodiments, therefore, the combination therapy or prophylaxis will additionally employ a chemotherapeutic agent, which is suitable selected from cytostatic agents and cytotoxic agents. Non-limiting examples of cytostatic agents are selected from: (1) microtubule-stabilizing agents such as but not limited to taxanes, paclitaxel, docetaxel, epothilones and laulimalides; (2) kinase inhibitors, illustrative examples of which include Iressa®, Gleevec, Tarceva™, (Erlotinib HCl), BAY-43-9006, inhibitors of the split kinase domain receptor tyrosine kinase subgroup (e.g., PTK787/ZK 222584 and SU11248); (3) receptor kinase targeted antibodies, which include, but are not limited to, Trastuzumab (Herceptin®), Cetuximab (Erbitux®), Bevacizumab (Avastin™), Rituximab (Ritusan®), Pertuzumab (Omnitarg™); (4) mTOR pathway inhibitors, illustrative examples of which include rapamycin and CCI-778; (5) Apo2L/Trail, anti-angiogenic agents such as but not limited to endostatin, combrestatin, angiostatin, thrombospondin and vascular endothelial growth inhibitor (VEGI); (6) antineoplastic immunotherapy vaccines, representative examples of which include activated T-cells, non-specific immune boosting agents (i.e., interferons, interleukins) and immune check point inhibitors (e.g., antibodies or functional nucleic acid molecules) that inhibit or block the activity of an inhibitory checkpoint molecule (e.g., PD-1, PD-L1, CTLA-4, etc.); (7) antibiotic cytotoxic agents such as but not limited to doxorubicin, bleomycin, dactinomycin, daunorubicin, epirubicin, mitomycin and mitozantrone; (8) alkylating agents, illustrative examples of which include Melphalan, Carmustine, Lomustine, Cyclophosphamide, Ifosfamide, Chlorambucil, Fotemustine, Busulfan, Temozolomide and Thiotepa; (9) hormonal antineoplastic agents, non-limiting examples of which include Nilutamide, Cyproterone acetate, Anastrozole, Exemestane, Tamoxifen, Raloxifene, Bicalutamide, Aminoglutethimide, Leuprorelin acetate, Toremifene citrate, Letrozole, Flutamide, Megestrol acetate and Goserelin acetate; (10) gonadal hormones such as but not limited to Cyproterone acetate and Medoxyprogesterone acetate; (11) antimetabolites, illustrative examples of which include Cytarabine, Fluorouracil, Gemcitabine, Topotecan, Hydroxyurea, Thioguanine, Methotrexate, Colaspase, Raltitrexed and Capicitabine; (12) anabolic agents, such as but not limited to, Nandrolone; (13) adrenal steroid hormones, illustrative examples of which include Methylprednisolone acetate, Dexamethasone, Hydrocortisone, Prednisolone and Prednisone; (14) neoplastic agents such as but not limited to Irinotecan, Carboplatin, Cisplatin, Oxaliplatin, Etoposide and Dacarbazine; and (15) topoisomerase inhibitors, illustrative examples of which include topotecan and irinotecan.

Illustrative cytotoxic agents can be selected from sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycarminomycin, annamycin, galarubicin, elinafide, MEN10755, 4-demethoxy-3-deamino-3-aziridinyl-4-methylsulphonyl-daunombicin (see International Publication WO 00/50032), methoxtrexate, gemcitabine, and mixture thereof.

In some embodiments, the concurrent administration of the C3aR antagonist and the mobilizer is used in combination with radiotherapies, such as but not limited to, conformal external beam radiotherapy (10-100 Grey given as fractions over 4-8 weeks), either single shot or fractionated, high dose rate brachytherapy, permanent interstitial brachytherapy, systemic radio-isotopes (e.g., Strontium 89). In illustrative examples of this type, the radiotherapy is administered in combination with a radiosensitizing agent. Illustrative examples of radiosensitizing agents include but are not limited to efaproxiral, etanidazole, fluosol, misonidazole, nimorazole, temoporfin and tirapazamine.

In some embodiments, an E-selectin antagonist is administered to delay hematopoietic stem cell turnover and/or protect hematopoietic stem cells from medical treatments that target rapidly dividing cells, such as radiation and chemotherapeutic treatments and/or to enhance mobilization of hematopoietic stem cells and/or progenitor cells, as disclosed for example in International Publications WO 2009/073911 and WO 2009/073916, which are hereby incorporated by reference herein in their entirety. Representative E-selectin antagonists include antigen-binding molecules that are immuno-interactive with E-selectin, peptides that bind to E-selectin and that block cell-cell adhesion, as well as carbohydrate or peptide mimetics of E-selectin ligands as described for example in WO 2009/073911 and WO 2009/073916. The E-selectin antagonist is suitably concurrently administered with the C3aR antagonist and the mobilizer.

Medical treatments such as myeloablative or cytoreductive therapies that target rapidly dividing cells and/or disrupt the cell cycle or cell division generally lead to immunocompromised conditions in the treated subject. When a subject is immunocompromised, pathogenic infections usually result and thus the present invention further contemplates further administering to the subject to an anti-infective agent that is effective against an infection that develops or that has an increased risk of developing from an immunocompromised condition resulting from a medical treatment as broadly described above.

The anti-infective agent is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective agents also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

It is also known that medical treatments that target rapidly dividing cells and/or disrupt the cell cycle or cell division (e.g., chemotherapy and radiation therapy) are immunocompromising since cells of the immune system including hematopoietic cells are destroyed or substantially reduced in number, thus leading to a state of immunosuppression characterized by neutropenia, agranulocytosis, thrombocytopenia and/or anemia. Anemia, thrombocytopenia, neutropenia and agranulocytosis are frequently defined in terms of laboratory measurements indicating a reduced hematocrit (volume percent), a reduced platelet count (per $mm^3$), a reduced neutrophil count (per $mm^3$), a reduced total granulocyte (i.e., neutrophils, basophils and eosinophils) or white blood cell count (per $mm^3$), respectively. Methods of determining these values are well known in the art, including automated as well as manual methods. The lower limits of normal for hematocrits and platelet counts in healthy non-pregnant humans is somewhat variable, depending on the age and sex of the subject, method of determination, and the norms for the laboratory performing the measurements. Generally, however, an adult human subject is said to have anemia when the hematocrit is less than about 37-40%. Likewise, generally an adult human subject is said to have thrombocytopenia when the platelet count is below about 100,000 per $mm^3$. Anemia is also frequently reported in terms of a reduced hemoglobin (g/dL) or red blood cell count (per $mm^3$). Typical lower limits of normal values for these in healthy adult humans are 12-13 g/dL and about $4.1 \times 10^6$ per $mm^3$, respectively. Generally an adult human subject is said to have neutropenia when the neutrophil count falls below 1000 per $mm^3$. Additionally, an adult human is generally said to have agranulocytosis when the total granulocyte cell count falls below 500 cells/$mm^3$. Corresponding values for all these parameters are different for other species.

Hematopoietic disorders such as anemia, thrombocytopenia, neutropenia and agranulocytosis are also frequently associated with clinical signs and symptoms in relation to their degree of severity. Anemia may be manifested as pallor, generalized fatigue or weakness, reduced exercise tolerance, shortness of breath with exertion, rapid heart rate, irregular heart rhythm, chest pain (angina), congestive heart failure, and headache. Thrombocytopenia is typically manifested in terms of spontaneous or uncontrolled bleeding, petechiae, and easy bruising. Neutropenia is associated with infections, including notably infections from endogenous microbial flora, and lack of inflammation.

Accordingly, the present invention further contemplates ancillary combination therapies in embodiments in which medical treatments are used to target rapidly dividing cells and/or disrupt the cell cycle or cell division, which leads to a hematopoietic disorder. These ancillary combination therapies will generally employ the C3aR antagonist/mobilizer combination and an ancillary treatment that treats the hematopoietic disorder, selected from an anemia medicament, a thrombocytopenia medicament, an agranulocytosis medicament or a neutropenia medicament, illustrative examples of which include steroids, inducers of steroids, and immunomodulators.

The steroids include, but are not limited to, systemically administered corticosteroids including methylprednisolone, prednisolone and prednisone, cortisone, and hydrocortisone. Inducers of steroids include, but are not limited to adrenocorticotropic hormone (ACTH).

Corticosteroids inhibit cytokine production, adhesion protein activation, and inflammatory cell migration and activation. The side effects associated with systemic corticosteroids include, for instance, reversible abnormalities in glucose metabolism, increased appetite, fluid retention, weight gain, mood alteration, hypertension, peptic ulcer, and aseptic necrosis of bone. Some side effects associated with longer term use include adrenal axis suppression, growth suppression, dermal thinning, hypertension, diabetes mellitus, Cushing's syndrome, cataracts, muscle weakness, and in rare instances, impaired immune function. It is recommended that these types of compounds be used at their lowest effective dose.

Commonly used anemia drugs which are currently on the market or in development include recombinant human EPO (EPOGEN; PROCRIT), preparations of iron (ferrous and ferric, CHROMAGEN; FEOSOL; INFED; IROSPAN; NEPHRO-FER; NEPHRO-VITE; NIFEREX; NU-IRON; SLOW FE), vitamin B12, vitamin B6, folic acid (CHROMAGEN; FERRO-FOLIC; NEPHRO-FER; NIFEREX), ascorbic acid, certain metabolites of vitamin D (calcitriol and alphacalcidol; CALCIJEX; ROCALTROL), androgens, and anabolic steroids (ANADROL), carnitine. In a specific embodiment the anemia medicament is recombinant EPO.

Drugs in common usage or development for the treatment of thrombocytopenia include glucocorticoids (prednisolone; prednisone; methylprednisolone; SOLUMEDROL), recombinant TPO, recombinant MGDF, pegylated recombinant MGDF, and lisophylline. In a specific embodiment the thrombocytopenia medicament is recombinant TPO.

Drugs in common usage or development for the treatment of neutropenia include glucocorticoids (prednisolone; prednisone; methylprednisolone; SOLUMEDROL), immunoglobulin G (SANDOGLOBULIN, IVEEGAM, GAMMAR-P, GAMIMNE N, GAMMAGARD S/D), androgens, recombinant IFN-γ (ACTIMMUNE), and uteroferrin. Antibiotics are frequently administered in association with neutropenia medicaments to treat or reduce the risk of infection.

In order that the invention may be readily understood and put into practical effect, particular preferred embodiments will now be described by way of the following non-limiting examples.

Experimental

Results $C3_A$-$C3_AR$ Signaling Contributes to Tumor Growth

To determine whether C3a-C3aR signaling influences tumor growth, the present inventors compared the growth of B16 melanoma in C3aR-deficient (C3aR−/−) and wild-type (C57Bl/6J) mice. The rate of tumor growth in C3aR$^{-/-}$ mice was significantly retarded compared with WT mice (FIG. 1A). Analysis of excised tumor weight at termination (day 14) confirmed that tumors were markedly smaller (23% of control) in C3aR$^{-/-}$ mice (FIGS. 1B, C). Further, survival of C3aR$^{-/-}$ mice (i.e., euthanasia once tumors reached the pre-determined size of 150 mm$^2$) was increased by 70% to 26.6±1.4 days, compared with 15.7±0.7 days for the WT controls (FIG. 1D). These results suggest that host C3aR signaling promotes B16 tumor growth.

Effect of Combined $C3_AR/C5_AR$ Blockade on Melanoma Growth

Since previous reports have demonstrated a role for the downstream activation product C5a in promoting tumor growth (Corrales et al., 2012; Gunn et al., 2012; Markiewski et al., 2008), the present inventors next investigated whether the tumor inhibitory effects observed in C3aR$^{-/-}$ mice could be augmented by C5a receptor (C5aR1) antagonism. For this experiment, melanomas were induced in WT and C3aR$^{-/-}$ mice. Once tumors became palpable (day 8), mice were administered daily s.c. injections of C5aR antagonist (C5aRA; PMX53) or vehicle alone. As previously shown in other tumor models (Corrales et al., 2012; Gunn et al., 2012; Markiewski et al., 2008), C5aR1 antagonism inhibited melanoma growth in WT mice (FIG. 1E, F). However, the reduction in tumor growth observed in C3aR$^{-/-}$ mice was not enhanced by C5aR inhibition, indicating that the contribution of C3aR signaling to melanoma growth is at least as potent as C5aR signaling, with both receptors potentially working through overlapping mechanisms.

$C3_AR$ Blockade Inhibits Growth of Established Primary Melanoma

Figure 2:
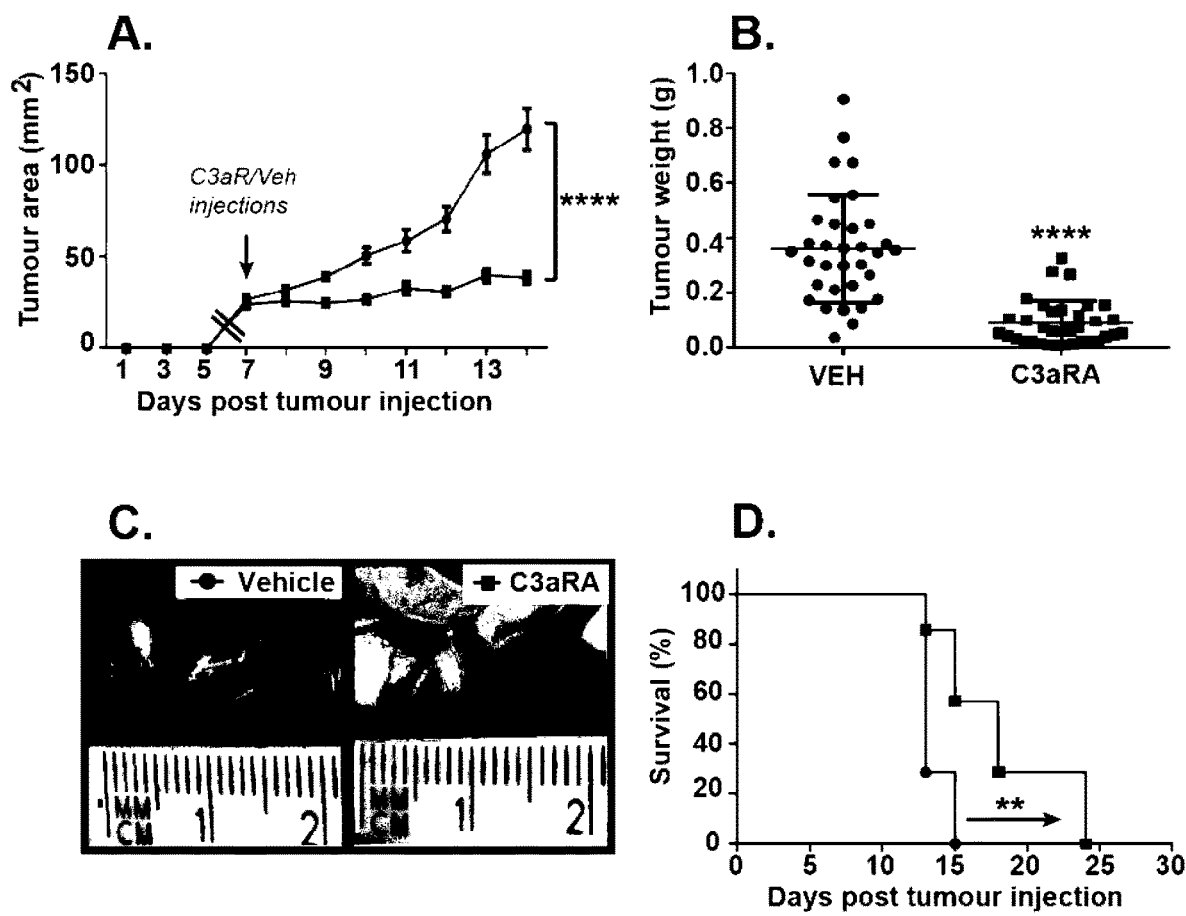
FIGS. 2A to 2D are a graphical and photographic representation showing that C3aR blockade halts growth of established B16 melanomas.

The potent anti-tumor results in the C3aR$^{-/-}$ mice prompted studies to determine the potential of C3aR therapeutic inhibition. Accordingly, the therapeutic potential of a C3aR antagonist (C3aRA; SB290157) was investigated on the growth of established melanoma. As shown in FIG. 2A, tumor progression was dramatically retarded by daily i.p. injection of C3aRA (commencing at day 7, once tumors became palpable), with tumor area remaining relatively constant from this time, and significantly smaller than in the vehicle-treated control group; excised tumor weights at day 14 were also significantly smaller in the C3aRA treatment group (FIG. 2B, C). Similarly, survival rates were significantly improved by treatment with C3aRA (FIG. 2D). Together these data suggest C3aR as a potential therapeutic target for the treatment of established melanomas.

B16 Melanoma Cells Express Functional C3AR

Figure 3:
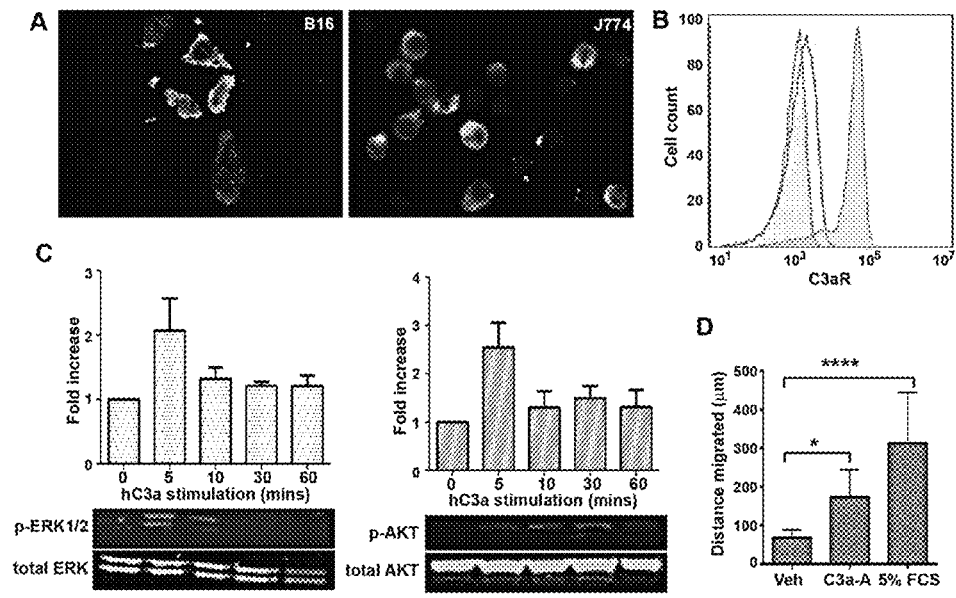
FIGS. 3A to 3D are a graphical and photographic representation showing that B16 melanoma cells express functional C3aR.

In light of a recent demonstration that tumor-derived complement proteins can promote ovarian tumor growth via autocrine mechanisms (Cho et al., 2014), experiments were carried out to determine whether B16 cells express C3aR. This was confirmed by immunostaining (FIG. 3A) and FACS analysis (FIG. 3B) which showed C3aR expression by cultured B16 cells, albeit at lower levels than for J774 macrophages which are known to have high levels of C3aR expression. Although stimulation of these receptors with recombinant human C3a or a selective C3aR agonist failed to initiate a calcium mobilization response, ERK and AKT signaling pathways were activated (FIG. 3C), suggesting that the receptors are functionally coupled. Stimulation of cells with a C3aR agonist had no significant effect on tumor cell proliferation, however cell migration was significantly increased (FIG. 3D), suggesting that C3a can exert effects directly on tumor cells.

Tumor-Infiltrating Leukocyte Populations are Altered in C3AR Deficient Mice

Figure 4:
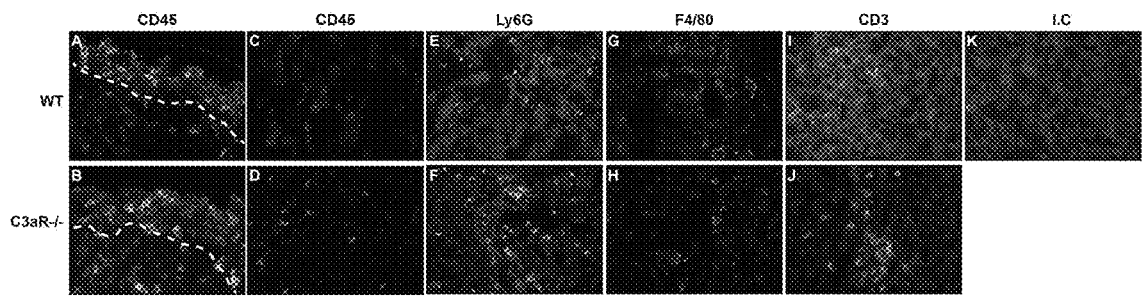
FIGS. 4A to 4K are a photographic representation showing leukocyte infiltration of B16 melanomas from C3aR-deficient and wild-type mice.

Despite demonstrating that B16 melanoma cells are able to respond to C3a, in vivo experiments showed that the growth of C3aR-expressing B16 melanoma cells was markedly inhibited in C3aR-deficient mice (FIG. 1), indicating a predominant role for host-expressed C3aR in the anti-tumor response. To further investigate the effects of host-expressed C3aR on tumor growth, tumor infiltrating leukocyte populations were compared in C3aR$^{-/-}$ and WT mice. Immunofluorescence staining of tumor tissue demonstrated a band of (CD45$^+$) leukocytes encapsulating subcutaneous B16 tumors (FIGS. 4A, B), with cells also infiltrating tumor tissue in both C3aR$^{-/-}$ and WT mice (FIGS. S2C, D). Many tumor infiltrating leukocytes stained positive for neutrophils (Ly6G$^+$; FIGS. 4E, F), with neutrophil numbers apparently increased in C3aR-deficient mice. Macrophages (F4/80$^+$; FIGS. 4G, H) and T lymphocytes (CD3'; FIG. 4I, J) were also evident.

Figure 5:
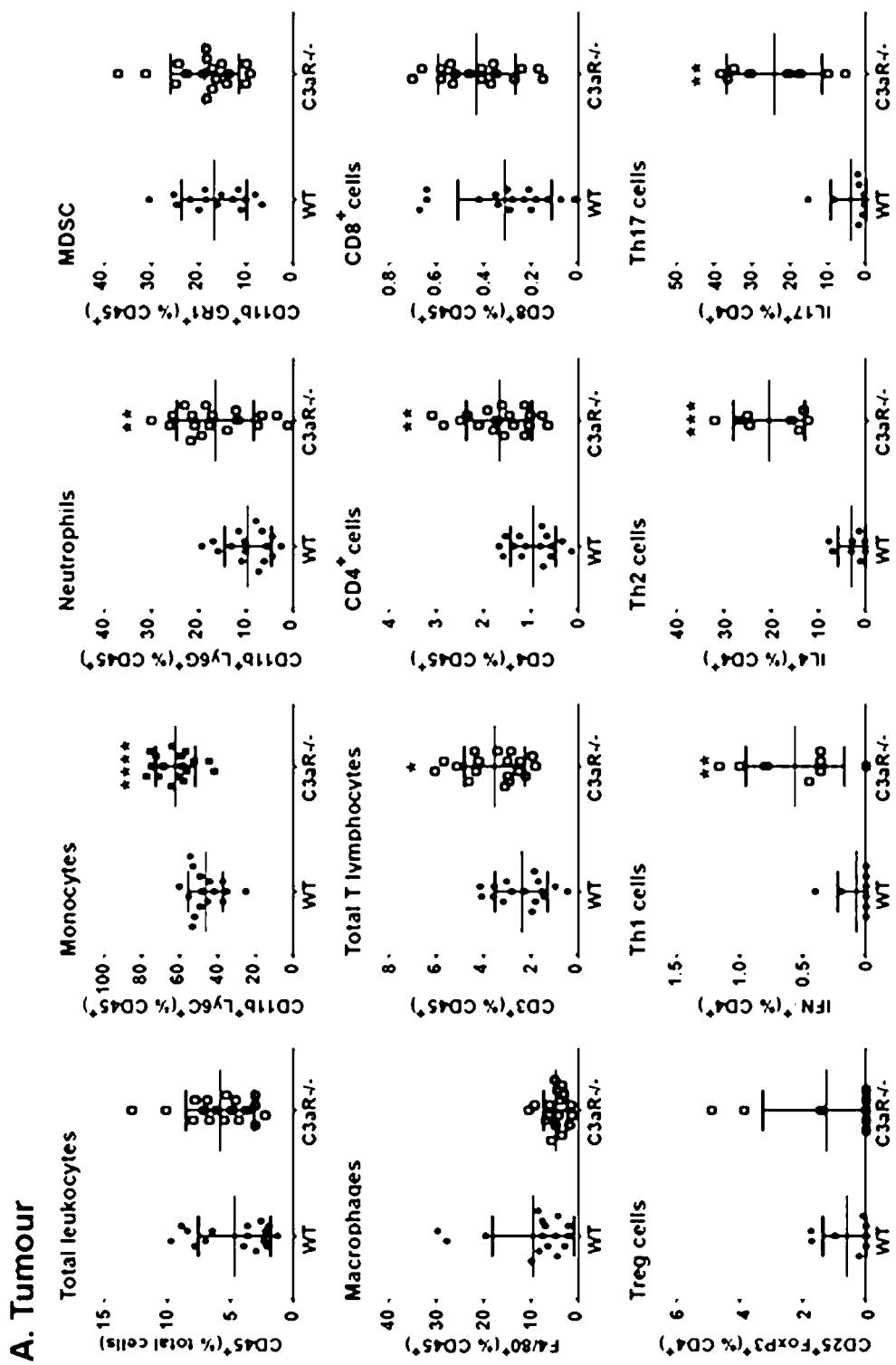
FIGS. 5A to 5C are a graphical representation showing that tumor-infiltrating leukocyte populations are altered in C3aR deficient mice.
Figure 5:
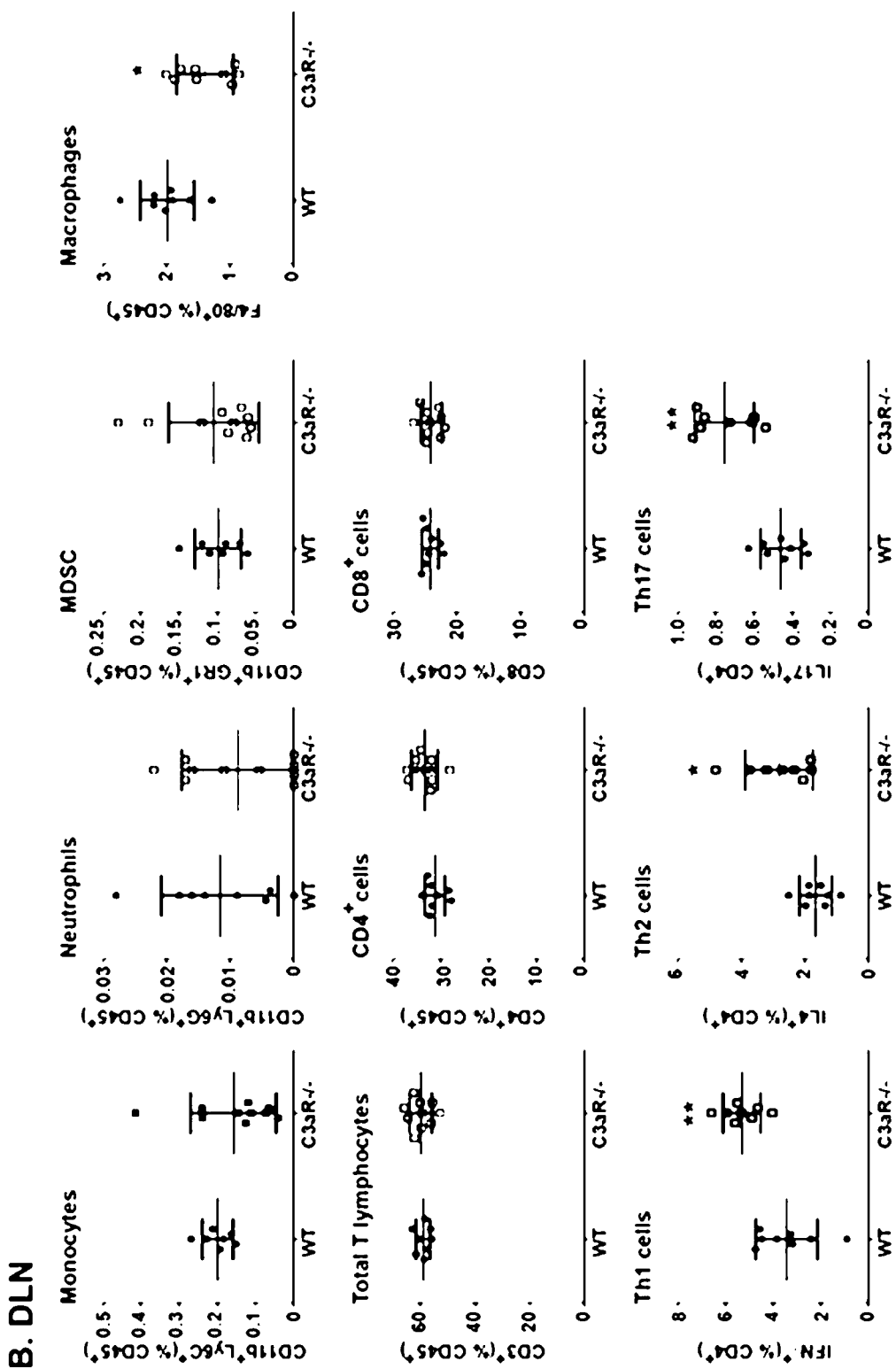
Figure 5:
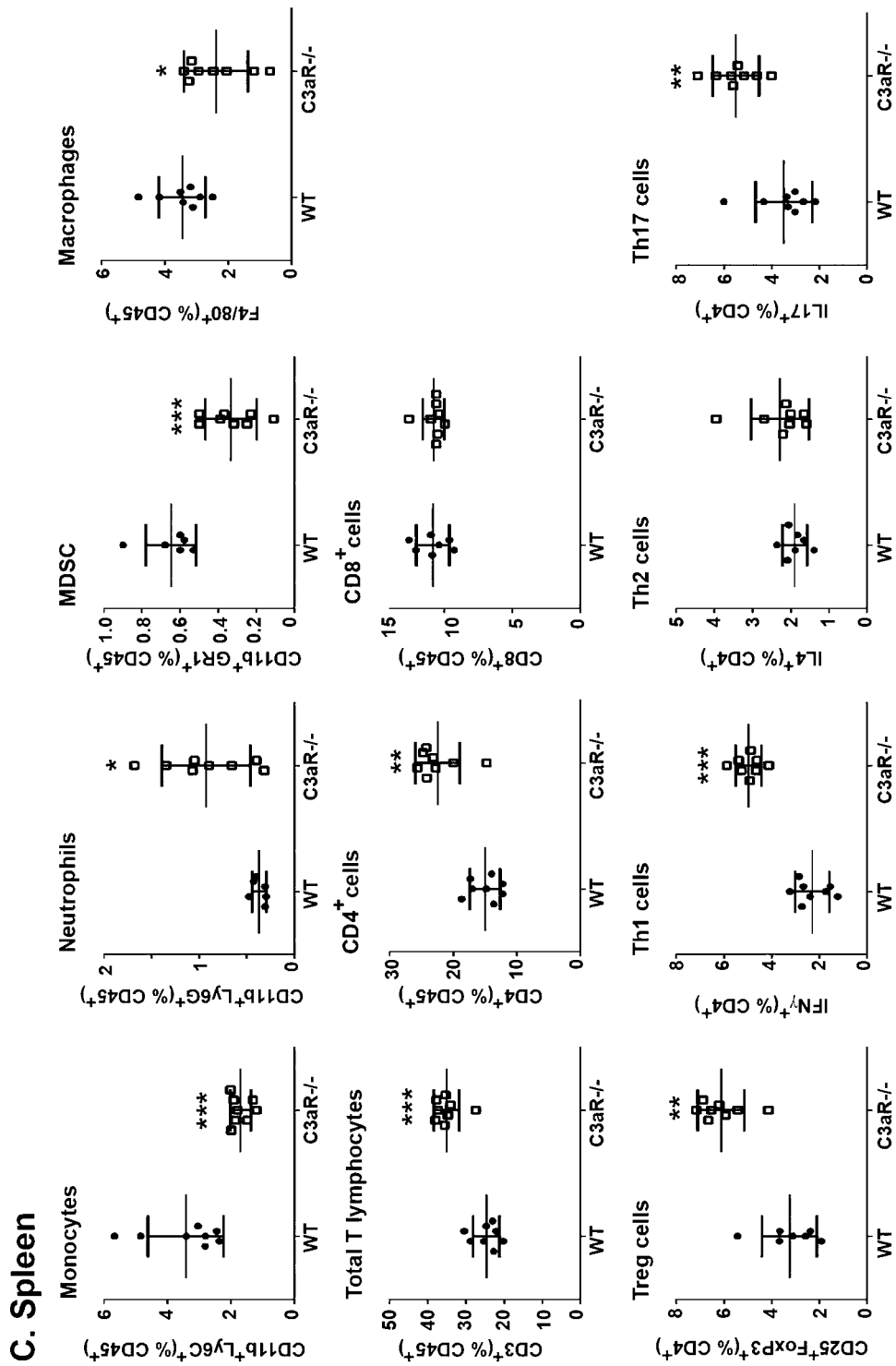

To quantitate potential alterations in the immune response to B16 melanomas, tumor infiltrating leukocyte populations were analyzed by flow cytometric analysis (FIG. 5A). Although the proportion of total leukocytes (CD45$^+$) within tumor tissue was not significantly altered in C3aR knockout mice (5.8±2.7% versus 4.7±2.9% in WT), the contribution of neutrophils (CD11b$^+$Ly6G$^+$) was significantly higher (16.6±8.1% of total leukocytes versus 9.7±4.8% WT). The relative contributions of monocytes (CD11b$^+$Ly6C$^+$) and total T lymphocytes (CD3) were also significantly higher, but B lymphocytes were unaltered (data not shown). In contrast to previous reports demonstrating that C5a promotes tumor growth via recruitment of myeloid-derived suppressor cells (MDSC) (Corrales et al., 2012; Gunn et al., 2012; Markiewski et al., 2008), the percentage of MDSC (CD11b$^+$GR1$^+$) was not significantly different in C3aR$^{-/-}$ mice and the proportion of macrophages (F4/80$^+$) was also unchanged (FIG. 5A). Investigation of tumor infiltrating CD3+ T lymphocyte subsets showed an increase in the proportion of CD4$^+$ T lymphocytes, but the proportion of CD8$^+$ T lymphocytes was not significantly different between WT and C3aR$^{-/-}$ mice; CD4/CD8 ratios were 2.99 and 2.64 respectively. While the proportion of regulatory T cells (CD4$^+$CD25$^+$Foxp$^+$; Tregs) was unchanged, Th1 (CD4$^+$ FNγ'), Th2 (CD4$^+$IL4$^+$) and Th17 (CD4$^+$IL17A$^+$) subsets were all significantly higher in tumors from C3aR$^{-/-}$ mice (FIG. 5A).

Figure 6:
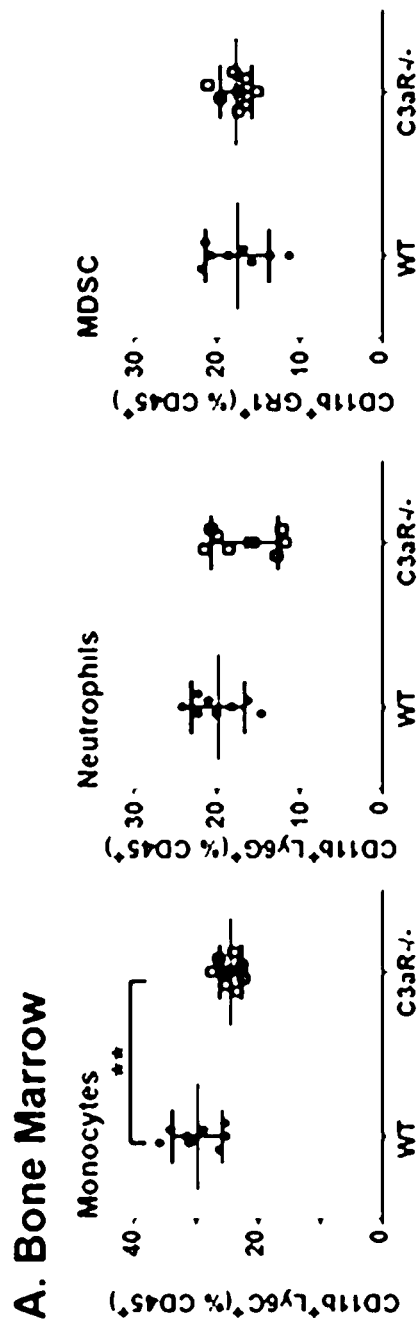
FIGS. 6A and 6B are a graphical representation showing that leukocyte populations are altered in tumor-bearing C3aR deficient mice.
Figure 6:
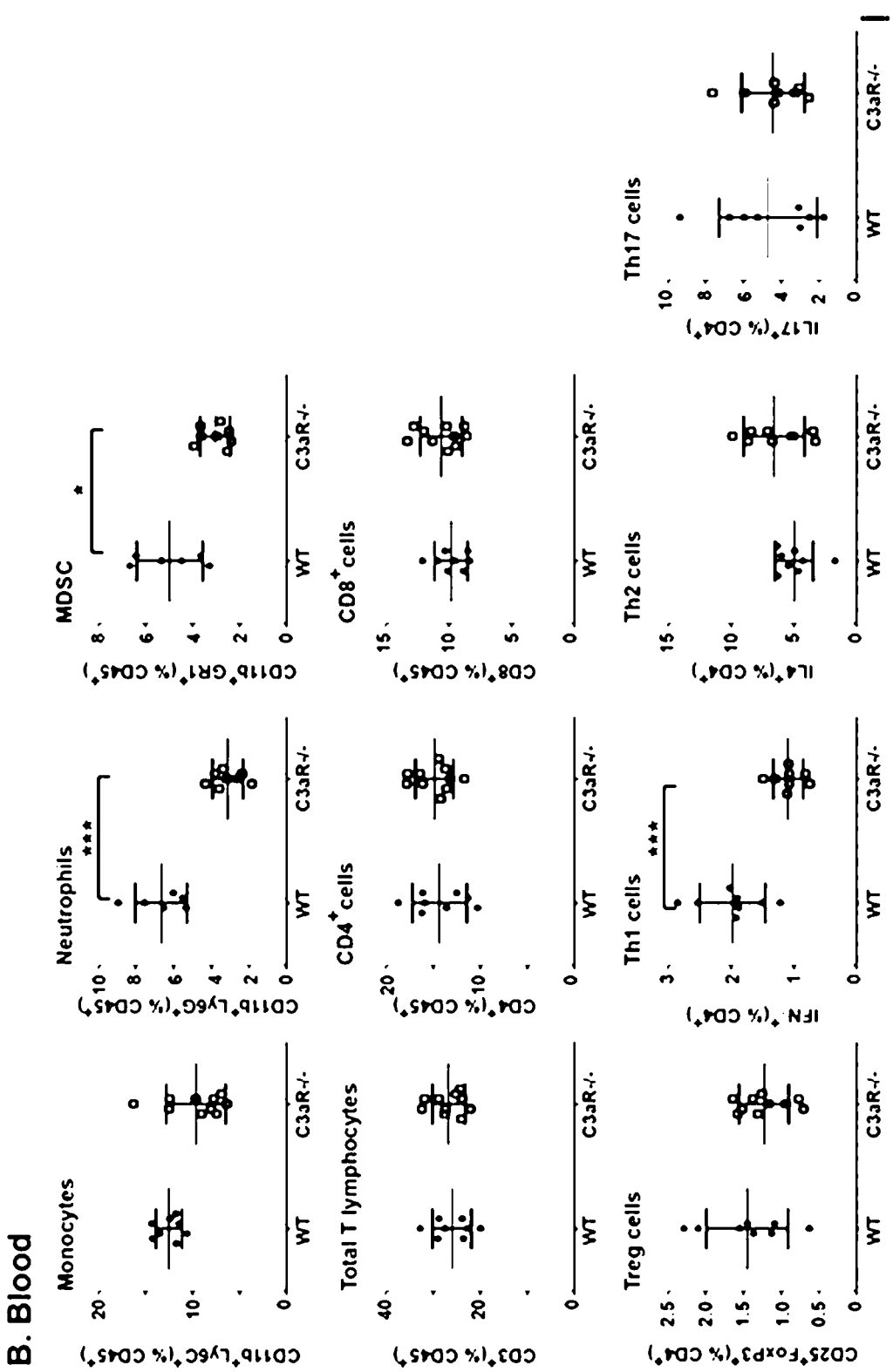

To investigate the distribution of these immune cell populations, leukocyte sub-populations were analyzed in bone marrow, blood, draining lymph nodes and spleen from tumor-bearing wild-type and knockout mice. Flow cytometric analysis of bone marrow cells (FIG. 6) revealed no significant differences in the proportions of monocytes or neutrophils in C3aR$^{-/-}$ mice. Analysis of blood from C3aR$^{-/-}$ and WT mice showed no difference in monocytes or T lymphocyte populations but the percentage of neutrophils was reduced (FIG. 6B), possibly reflecting the increased sequestration of neutrophils to the tumor site. Although no significant differences were detected in neutrophils, monocytes or total T cell populations, the percentages of Th1, Th2 and Th17 cells were increased in draining lymph nodes of C3aR$^{-/-}$ mice (FIG. 5B). Within the spleen, the proportions of monocytes (CD11b$^+$Ly6C$^+$) and MDSC (CD11b$^+$Gr1$^+$) were lower in C3aR$^{-/-}$ mice, but neutrophils were not significantly different. The percentage of total T lymphocytes was also significantly higher, as was the proportion of CD4$^+$ cells. Tregs, Th1 and Th17 CD4$^+$ subsets were all increased in C3aR$^{-/-}$ mice (FIG. 5C).

Figure 7:
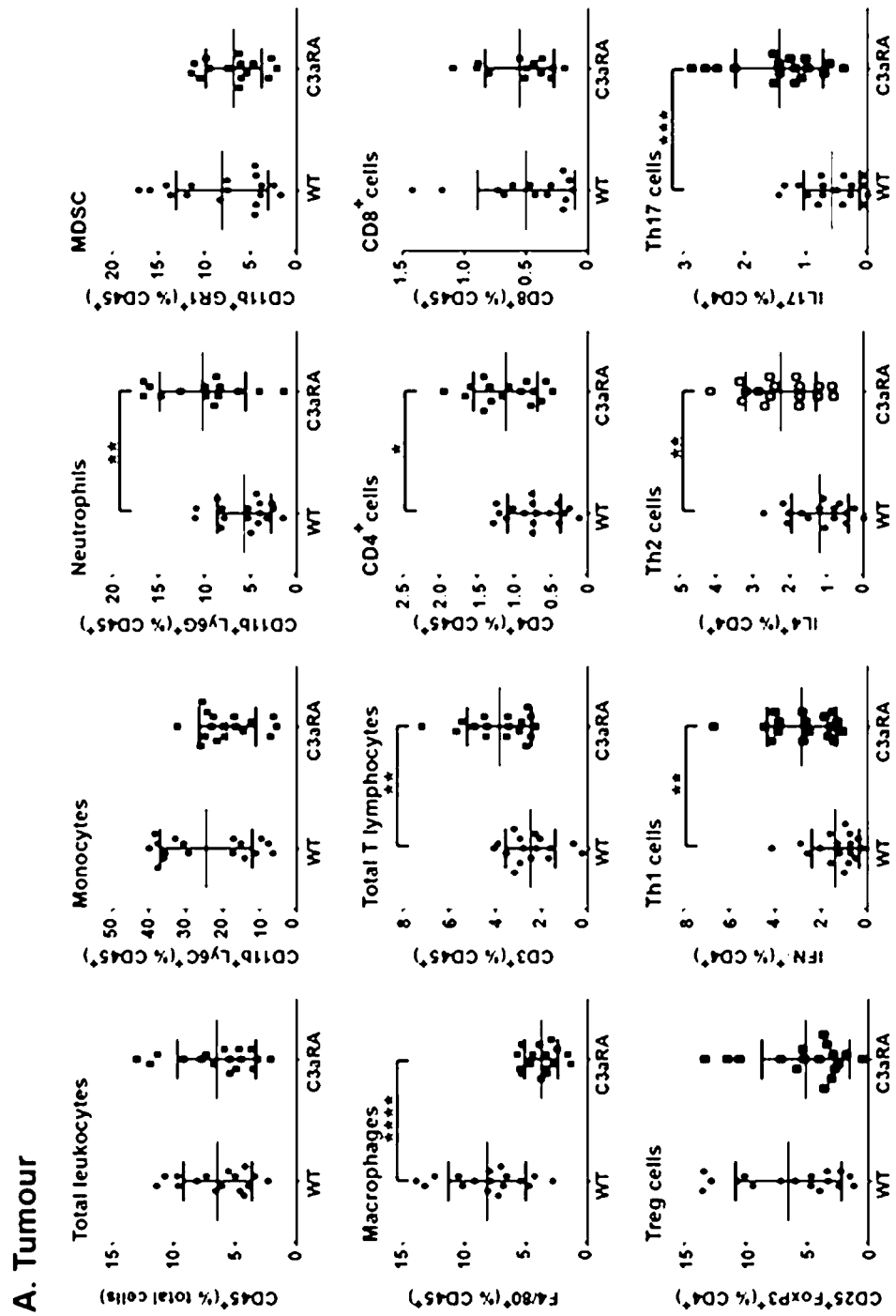
FIGS. 7A to 7C are a graphical representation showing the effect of C3aR-antagonism on tumor infiltrating leukocyte populations.
Figure 7:
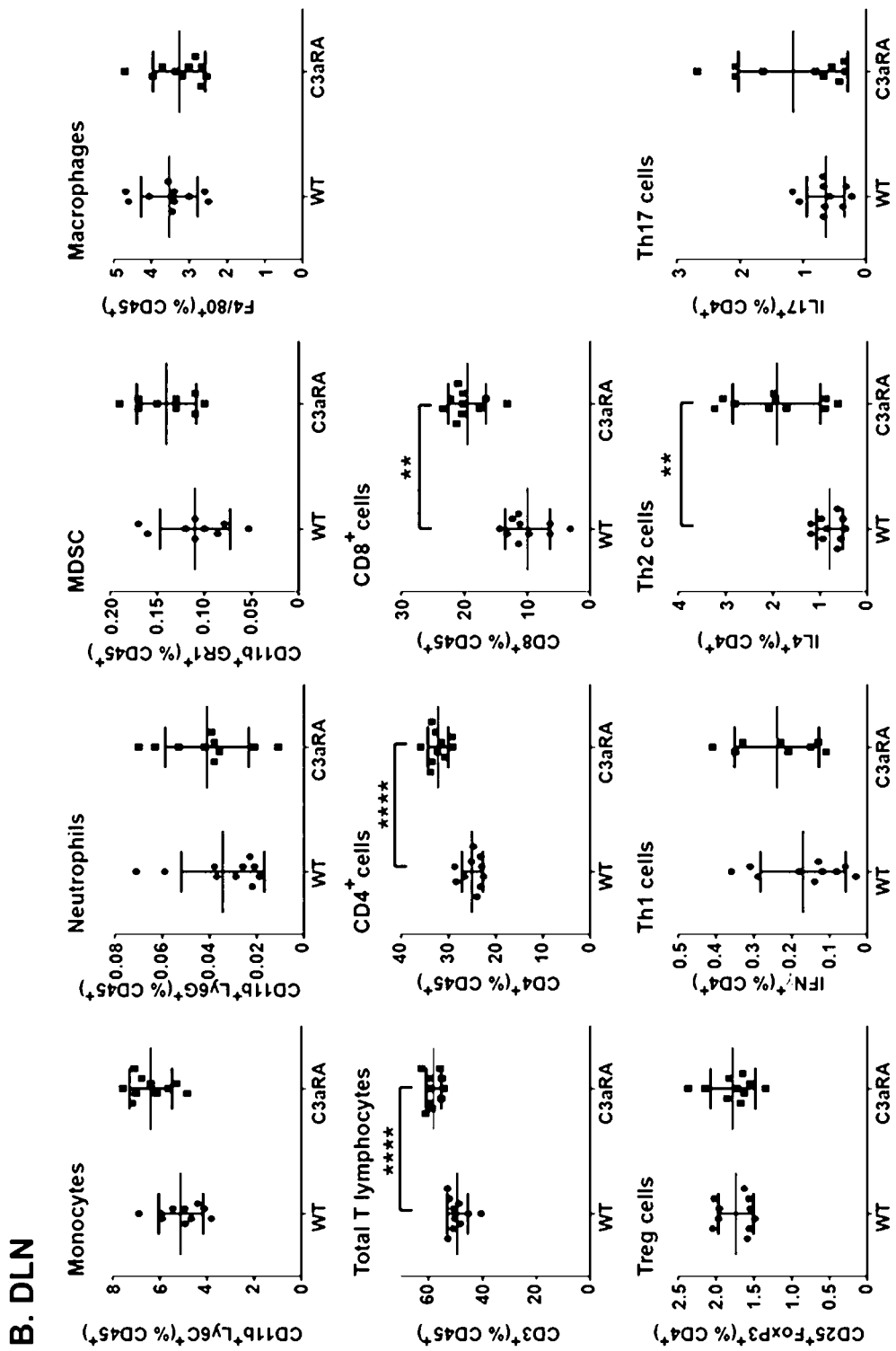
Figure 7:
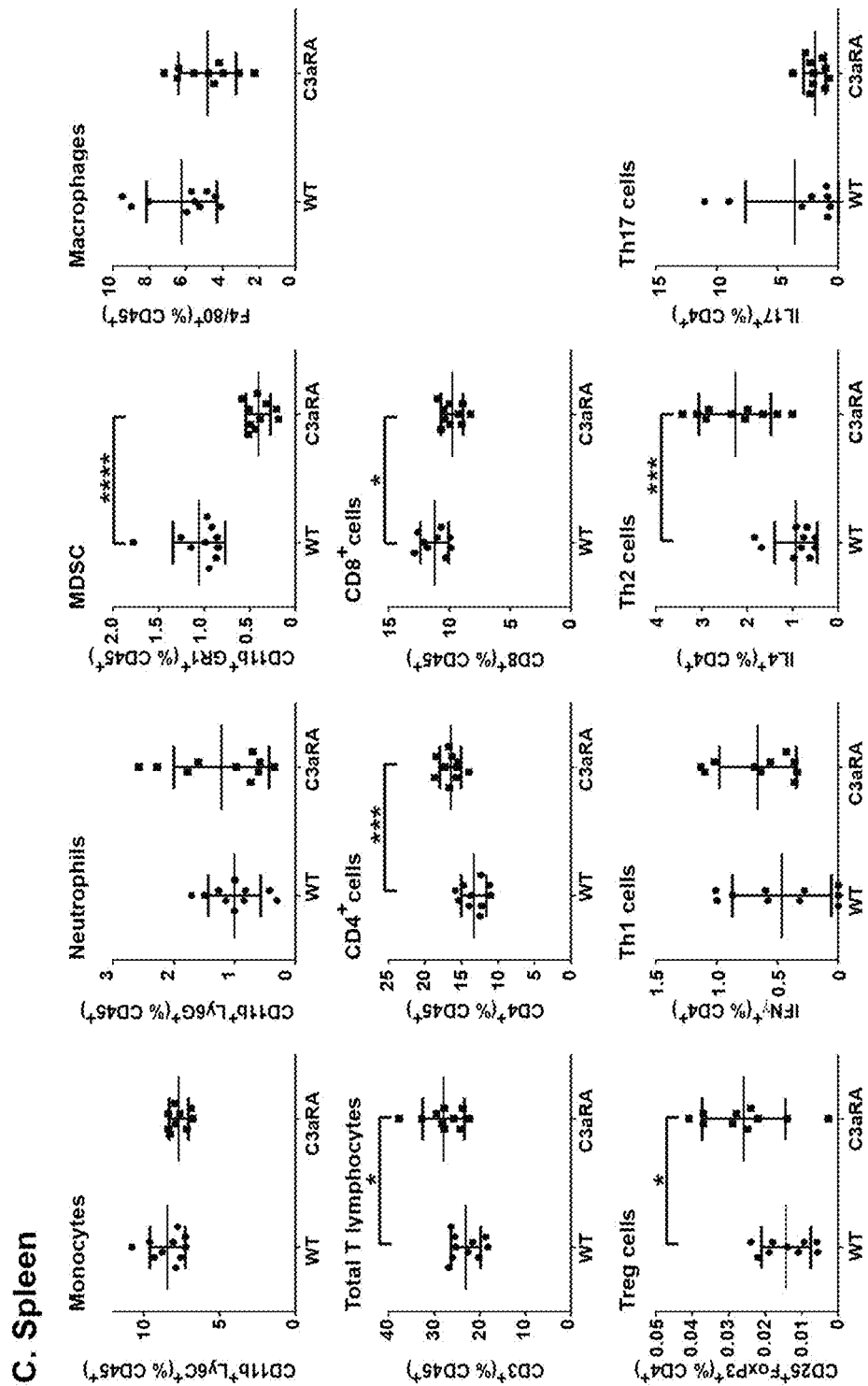

Tumor Infiltrating Leukocyte Populations are Similarly Affected Following C3AR Antagonism FACS analysis of tumor-infiltrating leukocyte populations in mice treated with the C3aR antagonist, SB290157 (C3aRA: FIG. 7A), showed a similar trend to C3aR$^{-/-}$ animals. The percentage of tumor-infiltrating neutrophils was increased by drug treatment. The proportion of MDSC in C3aRA-treated mice was not significantly altered compared with vehicle treated controls, but tumor-associated macrophages were reduced. As observed in C3aR$^{-/-}$ mice, the percentages of total and CD4$^+$ T lymphocytes were higher in tumors from drug-treated mice; the percentages of Th1, Th2 and Th17 subsets were also significantly increased.

Myeloid cell populations (monocytes, macrophages or neutrophils) were not significantly different in draining lymph nodes, but the percentages of T lymphocytes (both CD4+ and CD8+) were significantly increased in C3aRA-treated mice; of CD4+ subsets, only Th2 cells were significantly increased (FIG. 7B). In spleens from C3aRA-treated mice, the proportions of monocytes, neutrophils and macrophages were not significantly altered, whereas MDSC were significantly lower. Total and CD4$^+$ lymphocytes were significantly higher in the drug-treated group, coincident with significant increases in Treg and Th2 cells (FIG. 7C).

Figure 8:
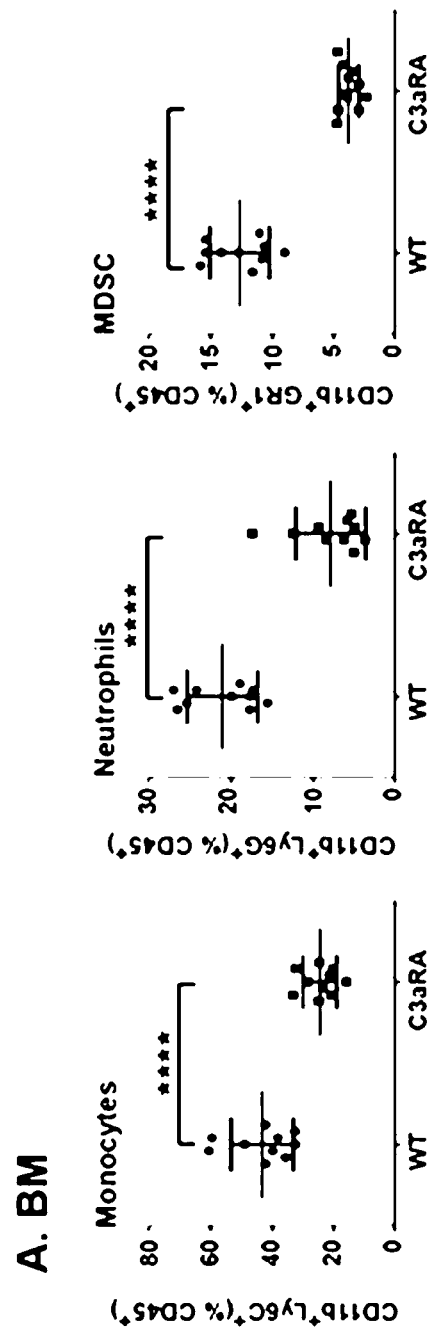
FIGS. 8A and 8B are a graphical representation showing that leukocyte populations in tumor-bearing mice are similarly affected following C3aR antagonism.
Figure 8:
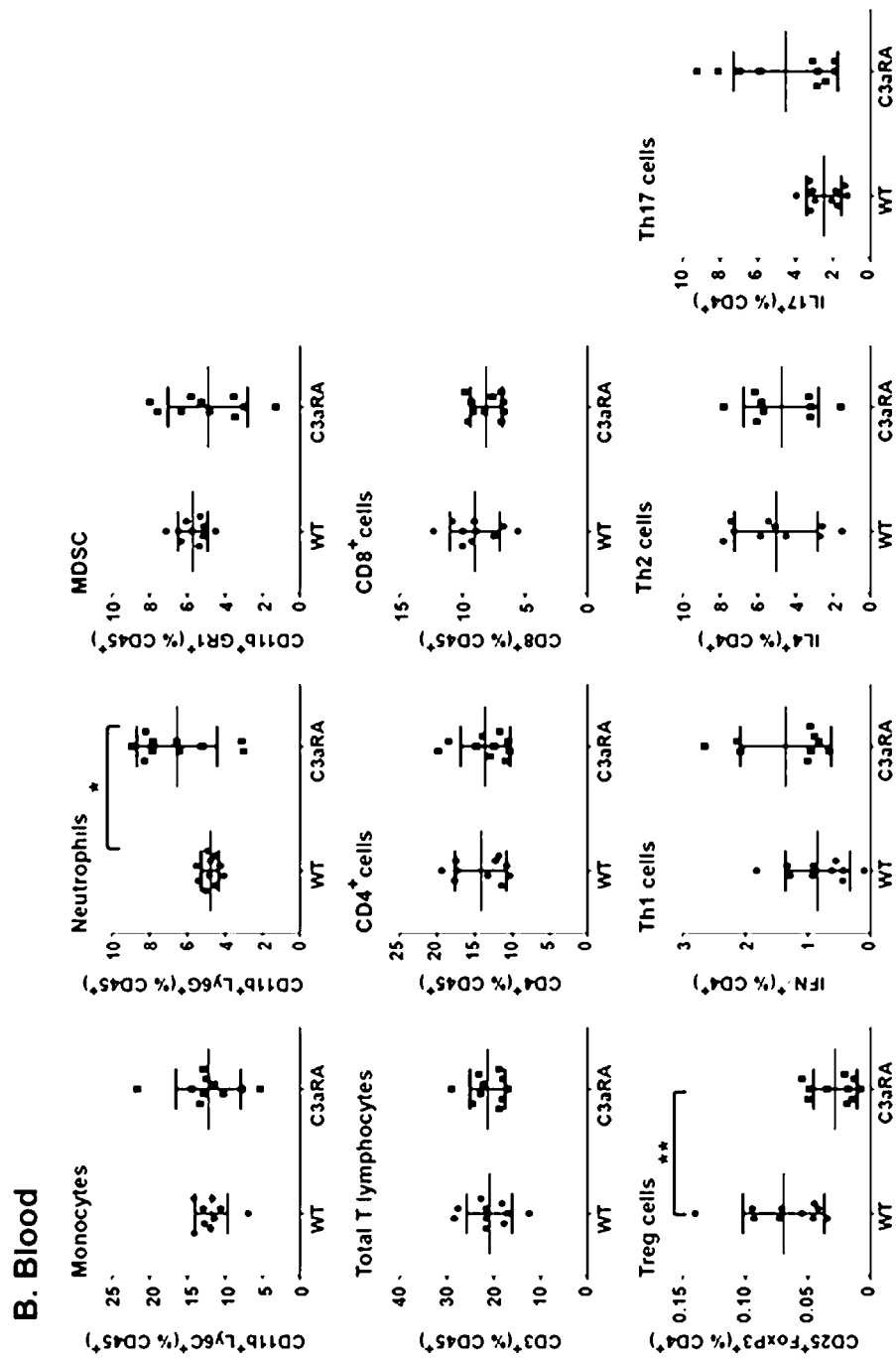

Although no significant differences were observed in bone marrow, myeloid cell populations from C3aR−/− mice (FIG. 6B), monocytes, neutrophils and MDSC were all significantly lower in bone marrow from C3aRA-treated mice (FIG. 8A). Analysis of blood showed a significant increase in neutrophils and reduction in Tregs (FIG. 8B)

Figure 9:
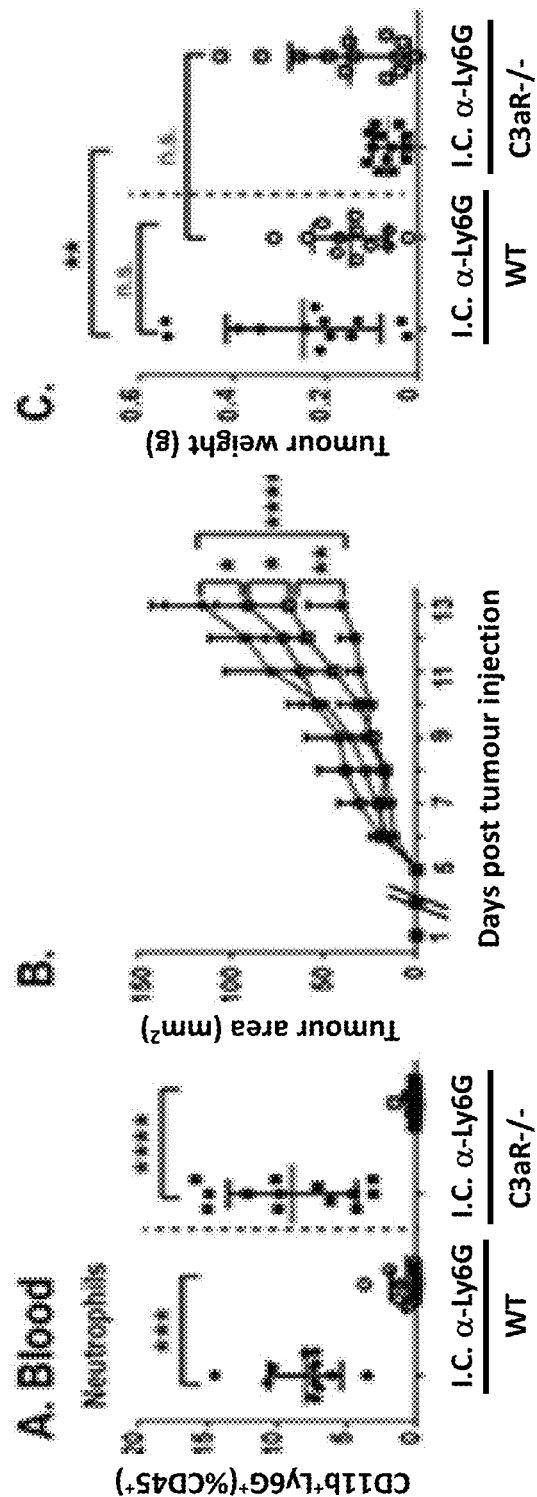
FIGS. 9A to 9D are a graphical representation showing that the tumor inhibitory effect of C3aR deficiency is rescued by neutrophil depletion.
Figure 9:
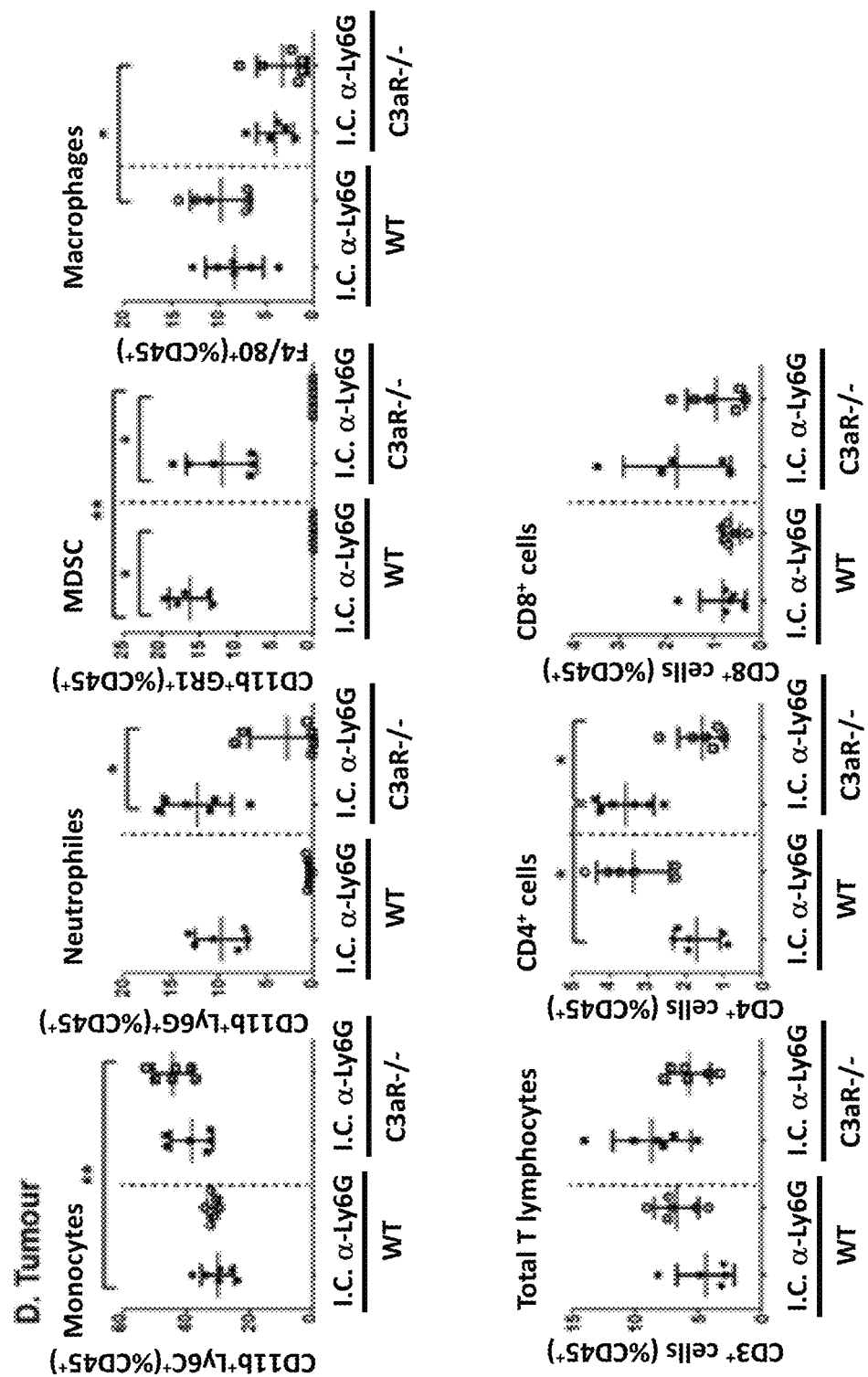

The Tumor Inhibitory Effect of C3AR Deficiency is Rescued by Neutrophil Depletion Given the FACS data showing an increase in tumor-infiltrating neutrophils in C3aR-deficient and antagonist-treated mice, we proposed that the influx of neutrophils into the tumor tips the balance towards an anti-tumor response. To determine whether neutrophils actively contribute to the tumor inhibition observed in the absence of C3aR signaling, we used a monoclonal antibody (α-Ly6G; 1A8) to deplete these cells (Daley et al., 2008). The efficacy of neutrophil depletion from WT and C3aR$^{-/-}$ mice was confirmed by FACS analysis of blood (FIG. 9A). Neutrophil depletion slowed tumor growth in WT mice, although the reduction in excised tumor weight was not significant (FIG. 9B, C). Conversely, the lack of neutrophils reduced the tumor inhibitory effects observed in C3aR$^{-/-}$ mice, such that excised tumor weight was not significantly different from that of WT mice treated with the isotype control antibody (I.C., 2A3; FIG. 9C). FACS analysis showed that neutrophil depletion was associated with a significant reduction in tumor-infiltrating CD4$^+$ T lymphocytes in C3aR$^{-/-}$ mice, with levels not significantly different to those in isotype control-treated mice, thus suggesting that neutrophils may be regulating the T cell response to tumor. Interestingly, α-Ly6G treatment also removed the majority of MDSC in both wild-type and knockout mice, indicating that in this tumor model the majority of MDSC are granulocytic.

C3AR Deficiency Influences Cytokine/Chemokine Expression

Figure 10:
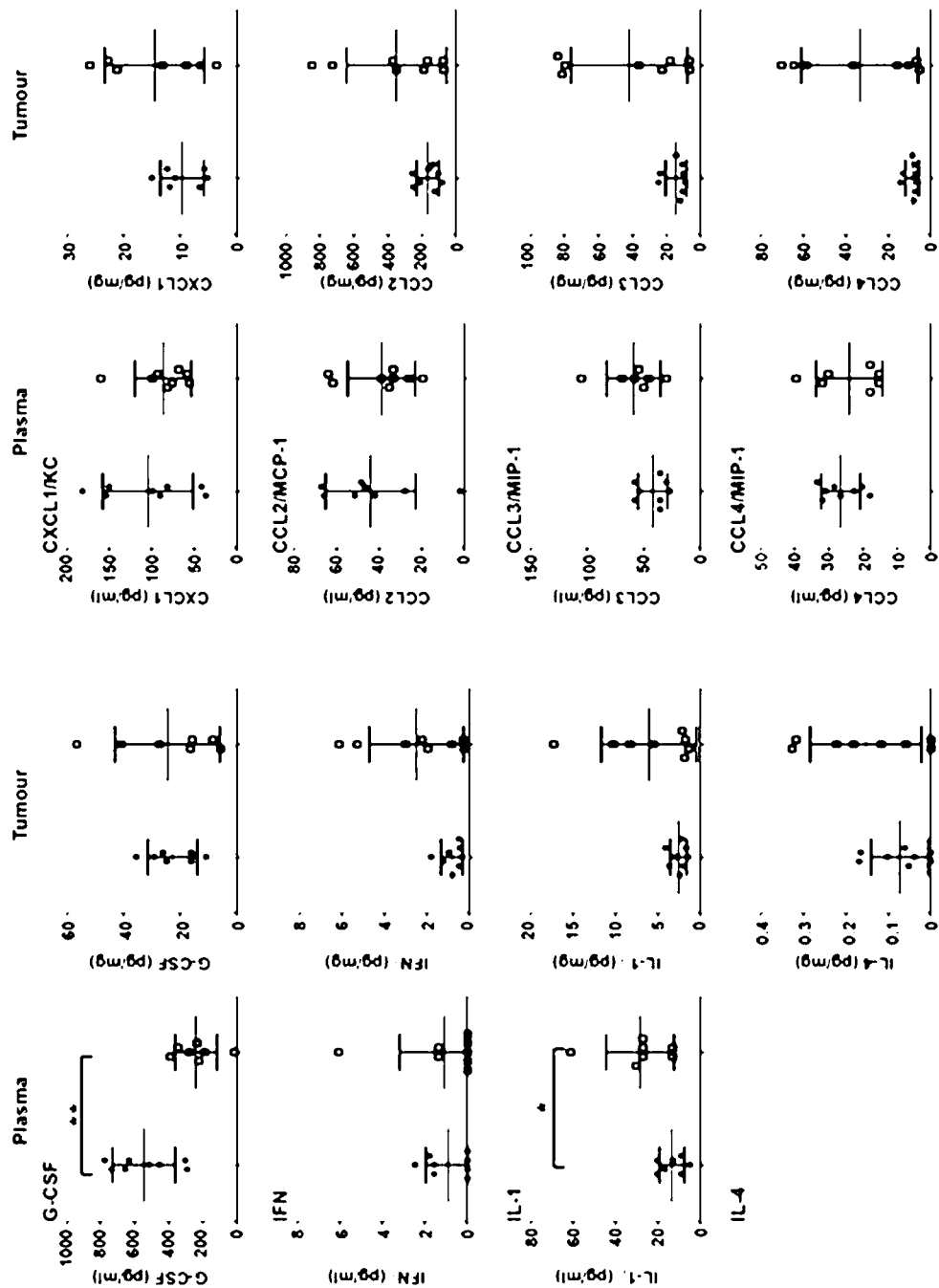
FIG. 10 is a graphical representation showing that C3aR deficiency influences cytokine/chemokine expression. Cytokine/chemokine levels in plasma and tumor tissue from WT (•) and C3aR$^{-/-}$ (☐) mice (n=6-8/group). Data expressed as pg/ml (for plasma) or pg/mg (for tumor tissue), mean±SD; *$p<0.05$, **$p<0.01$, Mann Whitney test.
Figure 10:
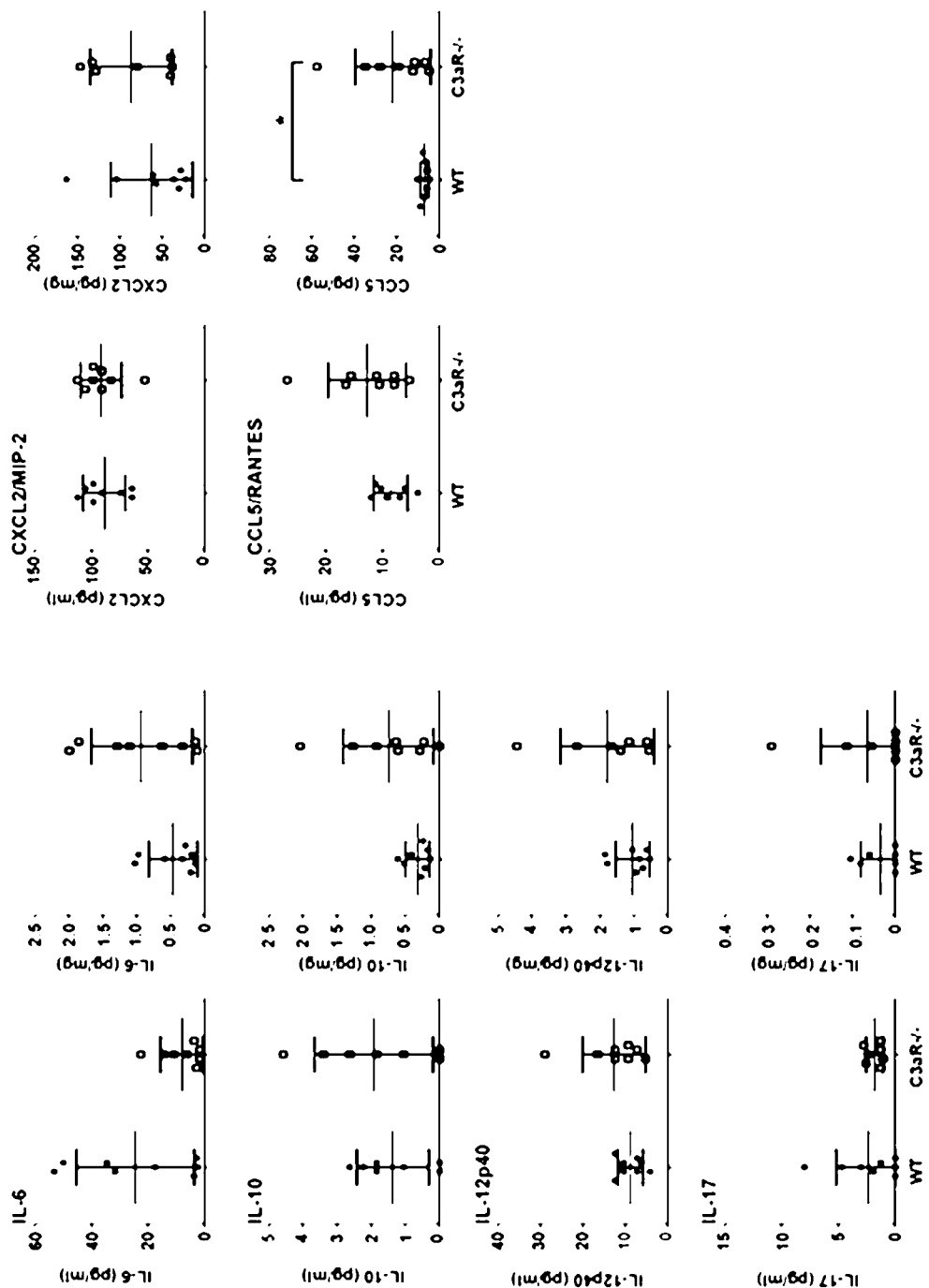

To determine how C3a regulates the inflammatory milieu within the tumor microenvironment, plasma and tumor tissue extracts were analyzed for a panel of cytokines and chemokines previously implicated as regulators of the anti-tumor response. As shown in FIG. 10, plasma G-CSF was significantly reduced in C3aR−/− mice whereas IL-1β was increased. There were no significant differences in plasma chemokine levels in C3aR−/− compared with WT mice, but the T cell chemokine CCLS (RANTES) showed significant up-regulation within tumor tissue extracts from C3aR−/− mice.

C3AR Signaling Contributes to the Growth of Other Tumor Types

Figure 11:
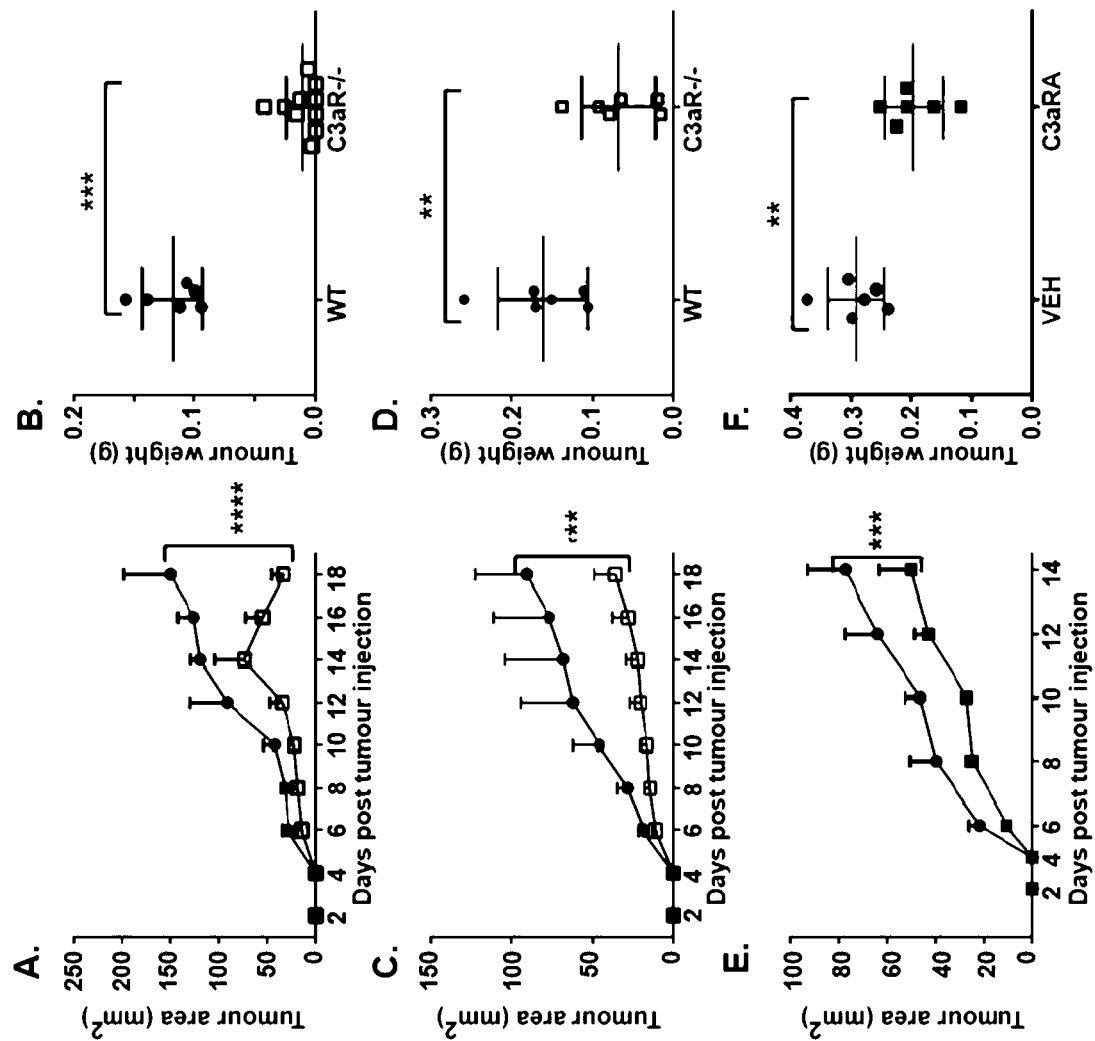
FIGS. 11A to 11F are a graphical representation showing that C3aR signaling contributes to the growth of other tumor types.

Finally, to determine whether or not the tumor promoting effects of C3aR signaling are restricted to the B16 melanoma model, the growth of two other tumor models: the murine melanoma cell line SM1WT1 which bears the BRAF$^{V600E}$ mutation harbored by approximately 50% of human melanomas and the colon cancer cell line MC38 in C3aR$^{-/-}$ mice was investigated. Similar to the results with B16 melanoma, the growth of both tumor types was significantly slowed in C3aR$^{-/-}$ mice compared with WT mice (FIG. 11A, C). Analysis of excised tumor weights at termination confirmed that tumors were smaller in C3aR$^{-/-}$ mice (91% reduction for SM1WT1 and 58% for MC38 tumors; FIGS. 11B, D). C3aR antagonist treatment of BALB/c mice harboring 4T1 mammary carcinomas also demonstrated significant inhibition of tumor growth (FIG. 11E, 11F). Overall, these results suggest the potential of C3aR as a therapeutic target for a range of tumor types.

Effect of C3AR Deficiency on Neutrophil Mobilization by G-CSF

Figure 12:
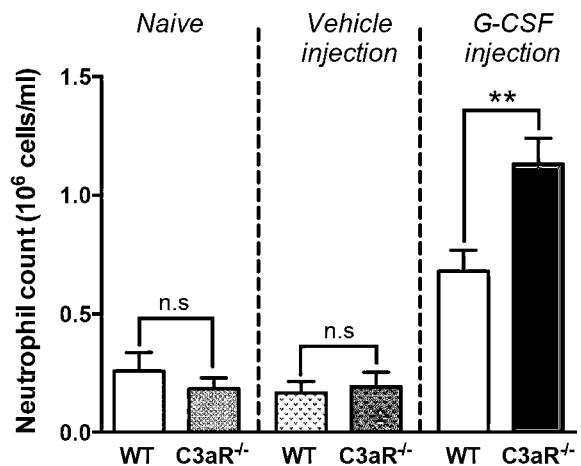
FIG. 12 is a graphical representation showing that C3aR limits G-CSF induced bone-marrow mobilization of neutrophils. Wild-type, or C3aR$^{-/-}$ mice were injected i.v. with G-CSF (Lenograstim; 120 μg/kg), or vehicle (saline). Blood neutrophil counts were determined 2-hours later using flow cytometry combining forward/side scatter gating with CD11b+Ly6G+ labeling. Whereas naïve (non-injected), and saline-injected wild-type and C3aR$^{-/-}$ mice have similar blood neutrophil counts, C3aR$^{-/-}$ mice show significantly (P=0.0056) greater mobilization of neutrophils in response to G-CSF compared with wild-type mice (n=9-11). This demonstrates that C3aR has no baseline influence on natural circulating levels of neutrophils, but specifically inhibits G-CSF neutrophil mobilization.
Figure 13:
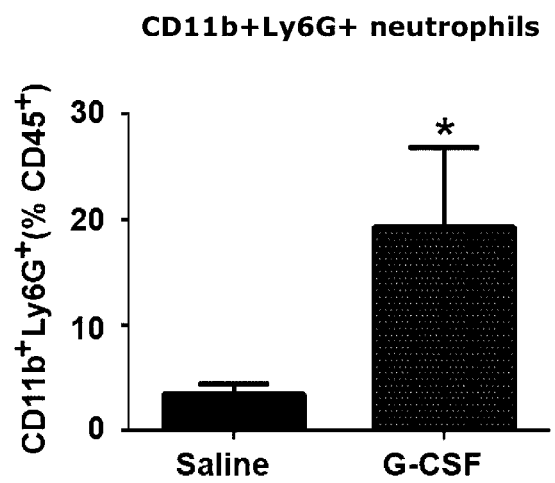
FIG. 13 is a graphical representation showing mobilization of anti-tumor (CD11b+Ly6G+) neutrophils in response to G-CSF. C3aR$^{-/-}$ mice were injected i.v. with G-CSF (Lenograstim; 120 µg/kg), or vehicle (saline). Blood anti-tumor neutrophils were determined 2-hours later using flow cytometry for markers for CD11b and Ly6G. G-CSF injection induced a significant (P=0.0079) increase in blood anti-tumor neutrophils compared with saline injection (n=6). It is proposed that the influx of newly mobilized CD11b+ Ly6G+ neutrophils into the tumor tips the balance from a pro-tumorigenic response (mediated by CD11b+Gr1+ granulocytic myeloid-derived suppressor cells) to an anti-tumor response.

Next, the inventors compared CD11b+Ly6G+ neutrophil mobilization in wild-type and in C3aR-/- mice following G-CSF administration. Results from this study revealed that C3aR has no baseline influence on natural circulating levels of neutrophils but markedly inhibits G-CSF induced mobilization of neutrophils from the bone marrow (FIG. 12). Of interest, in animals with loss of function in C3aR, G-CSF induced mobilization of CD11b+Ly6G+ neutrophils was significantly enhanced (FIG. 13). It is proposed that the influx of newly mobilized CD11b+Ly6G+ neutrophils into the tumor tips the balance from a pro-tumorigenic response (mediated by CD11b+Gr1+ granulocytic myeloid-derived suppressor cells) to an anti-tumor response.

Discussion

The demonstration herein that neutrophil depletion significantly reverses the tumor inhibitory effects observed in C3aR deficient mice implicates neutrophils as major contributors to the anti-tumor effects of C3aR deficiency/antagonism. Neutrophils are generally thought to promote tumor cell proliferation, angiogenesis and metastasis via the production of chemokines, cytokines and reactive oxygen species; they also contribute to MDSC populations which inhibit T cell responses (Gregory and Houghton, 2011). However, there is evidence that under certain conditions neutrophils can exert efficient anti-tumor activity (Souto et al., 2011), and activation of neutrophils by primary tumors has been shown to inhibit metastatic seeding (Granot et al., 2011). These differing roles of neutrophils in tumor growth may be explained by differences in activation status. Fridlender et al (2009) demonstrated in lung cancer models that like macrophages, neutrophils have differential states of activation: a pro-tumorigenic phenotype identified by increased expression of chemokines and growth factors (e.g., CCL2, CCL5, VEGF-A), and an anti-tumor phenotype associated with increased expression of cytokines (e.g., TNF-α), chemokines (CCL3) and adhesion molecules (ICAM-1). They showed that the presence of TGFβ within the tumor environment induces a population of pro-tumorigenic neutrophils, whereas TGFβ blockade resulted in recruitment and activation of anti-tumor neutrophils. More recently this same group has shown that tumor associated neutrophils have a unique transcriptional profile compared to naïve bone marrow neutrophils, and also differ from granulocytic MDSC (Fridlender et al., 2012). Thus the effects of neutrophils on tumor growth may depend on their activation status, such that a shift in cytokine expression within the tumor microenvironment from acute to chronic inflammation converts anti-tumor effector cells to tumor promoting neutrophils (Souto et al., 2011). This is supported by recent studies showing that neutrophils at the early stages of tumor development are more cytotoxic towards tumor cells (Mishalian et al., 2013) and capable of stimulating effective T cell responses (Eruslanov et al., 2014), but at later stages develop a pro-tumor phenotype.

Thus the present inventors propose herein that C3aR inhibition leads to sequestration of naïve neutrophils into the tumor microenvironment, which in turn tip the balance towards an anti-tumor neutrophil response. This may include the recruitment and activation of other anti-tumor effector cells, including T lymphocytes, via neutrophil release of cytokines and chemokines that augment an effector T cell response. This hypothesis is in accord with previous reports, for example by Medina-Echeverz et al (2011) who showed that an efficient anti-tumor response can be generated by altering the myeloid cell population within the tumor microenvironment and facilitating effector T cell infiltration. Indeed the present demonstration that CD4$^+$ T lymphocyte populations are increased in the absence of C3aR signaling, but return to normal (wild-type) levels following neutrophil depletion suggests that these newly mobilized neutrophils may promote effective anti-tumor T cell responses. Similar to Medina-Echeverz and co-workers who reported an up-regulation of Ml-associated cytokines/chemokines in anti-tumor myeloid cell populations, the present inventors show up-regulation of IL-1β and CCL5 in plasma and tumor tissue (respectively) from C3aR-/- mice. Although increased CCL5 levels have been associated with unfavorable outcomes in some cancers (Niwa et al., 2001), it is a predictor of survival in others (Chew et al., 2012; Moran et al., 2002). CCL5 has been implicated for a role in regulating anti-tumor immunity (Johrer et al., 2008; Mule et al., 1996), and shown in a mouse melanoma model to synergize with CXCR3 ligands to attract effector T cells into cutaneous metastases and inhibit tumor growth (Hong et al., 2011).

FACS analysis of tumor-infiltrating T lymphocyte populations showed C3aR-deficiency/inhibition increased Th1, Th2 and Th17 populations, but had no effect on CD8$^+$ T lymphocytes or Tregs. Although effective anti-tumor responses have been traditionally attributed to CD8$^+$ CTL (Fridman et al., 2012) supported by Th1 cells (Fridman et al., 2012; Ye et al., 2013), this is not always the case. Depending on the tumor type, anti-tumor responses can occur independently of cytotoxic CD8$^+$ T cells, mediated directly by Th1 Th2 or Th17 cells (Chu et al., 2006; Corthay et al., 2005; Kim and Cantor, 2014). Th2 cells have been reported to amplify the innate immune response to tumors by directly recruiting tumoricidal myeloid cells into the tumor (Musiani et al., 1996; Pericle et al., 1994). Moreover, the Th2 response has been reported to play a critical role in immunity to B16 melanoma (Mattes et al., 2003). Th17 populations may also be associated with favorable outcomes, for example, in melanoma (Martin-Orozco et al., 2009; Muranski et al., 2008) and esophageal (Lv et al., 2011) cancers.

Th17 cells comprise approximately 0.1-0.5% of circulating CD4$^+$ T cells in humans, but significantly higher densities are observed within tumor tissues, including melanoma (Su et al., 2010), prostate, fibrosarcoma, head and neck cancers (Kryczek et al., 2007). However their role in tumor growth is controversial, with tumor-infiltrating Th17 cells reported to either contribute to an anti-tumor cytotoxic T cell response or promote tumor growth by facilitating angiogenesis and suppressing the anti-tumor response (Hemdan, 2013). In animal models, induction of Th17 cells has been shown to support anti-tumor immunity. For example, up-regulated expression of IL-6 in a pancreatic tumor model was shown to skew the balance towards Th17 cells, delaying tumor growth and improving survival (Gnerlich et al., 2010) while antigen-specific Th17-polarised cells eradicated established B16 melanoma (Muranski et al., 2008) and metastatic prostate tumors (Kottke et al., 2007); Muranski and co-workers showed that the therapeutic effect of Th17 cells is dependent on their production of IFNγ.

Cytokine analysis of tumor bearing C3aR–/– mice also revealed a reduction in plasma G-CSF levels, which was not observed in wild-type mice. Having regard to the hypothesis that C3aR inhibition leads to an anti-tumor neutrophil response and that mobilization of anti-tumor neutrophils in C3aR deficient mice is significantly enhanced by administration of G-CSF, the present inventors propose that co-administration of G-CSF and C3aR antagonist to cancer subjects would mobilize hematopoietic stem cells and progenitor cells (HSPC) from the bone marrow, thereby further increasing the number of anti-tumor neutrophils with consequential increases in $CD4^+$ T lymphocytes, as compared to the administration of C3aR antagonist alone.

In summary, the present study identifies an important role for C3a/C3aR signaling in promoting tumor growth, and provides evidence that these pro-tumor effects are mediated at least partly via the host immune system. The results show that C3aR deficiency/antagonism leads to increased tumor-infiltrating leukocyte populations, including neutrophil and $CD4^+$ T lymphocyte populations. Although neutrophils are generally thought to promote tumor growth, there is considerable evidence in the literature that neutrophils can be manipulated to exert efficient anti-tumor activity. The present inventors propose that by mobilizing mature neutrophils from the bone marrow, C3aR inhibition and preferably through co-administration of stem cell-mobilizing agents such as G-CSF, will change the inflammatory equilibrium within the tumor environment, and thus tip the balance towards an anti-tumor response. The association of C3aR-deficiency with increased tumor-infiltrating $CD4^+$ cells suggests that a positive feedback loop may develop whereby the secretion of chemokines and cytokines by neutrophils sequestered to the tumor microenvironment promotes $CD4^+$ recruitment and expansion; cytokines produced by $CD4^+$ cells may in turn favor neutrophil recruitment and survival.

Materials and Methods

Cell Lines and Culture Medium

The murine melanoma B16-F0 (ATCC® CRL6322™; syngeneic in $C_{57}BL/63$ mice), mammary carcinoma 4T1 (ATCC® CRL-2539™) and macrophage J774A.1 (ATCC® TIB-67TH) cell lines were obtained from the American Type Culture Collection (Manassas, Va.). The murine SM1WT1 ($BRAF^{V600E}$ mutant; Knight et al., 2013) and MC38 colon carcinoma (Rosenberg et al., 1986) cell lines were obtained from Prof Mark Smyth, Queensland Institute for Medical Research.

Animals

Homozygous C3a receptor knockout ($C3aR^{-/-}$) or wild-type (WT; C57BL/6J) mice (6-8 weeks old, and sex-matched) were obtained from University of Queensland Biological Resources and fed a normal chow diet ad libitum. Female BALB/c mice were obtained from Monash Animal Services (Melbourne, Australia). All procedures were approved by the University of Queensland Animal Ethics Committee Guidelines and conformed to the Animal Care and Protection Act Qld (2002) and the Australian Code of Practice for the Care and Use of Animals for Scientific Purposes (8th edition, 2013).

Tumor Induction

WT or $C3aR^{-/-}$ mice were injected subcutaneously (s.c.) with B16-F0 melanoma ($2.5 \times 10^5$ cells/mouse) or MC38 colon carcinoma ($1 \times 10^6$ cells/mouse); female BALB/c mice were injected into the mammary fat pad with 4T1 mammary carcinoma ($5 \times 10^5$ cells/mouse). Tumor growth was monitored daily from day 5 after tumor cell injection. For some experiments, C57BL/63 mice received daily injections of either C3aR antagonist (SB290157; VDM Biochemicals, Bedford Heights, Ohio; diluted in saline, 1 mg/kg/day i.p.,), C5aR antagonist (PMX53; produced in-house; 1 mg/kg/day) or vehicle only (0.9% saline or 5% glucose solution) control, commencing once tumors became palpable (approx. day 7 after tumor cell injection). For most experiments, mice were euthanized at day 14 (or once the largest tumor reached an area of approx. 200 $mm^2$), blood was collected by cardiac puncture, tumors, spleen, draining lymph nodes (inguinal, axillary and brachial) and femurs excised for FACS or immunostaining; tumors were weighed. For 'survival' studies, the time taken for each tumor to reach a pre-determined size (150 $mm^2$) was recorded, then mice euthanized.

Neutrophil Depletion

WT and $C3aR^{-/-}$ mice were injected i.p. with anti-Ly6G antibody (1A8, selective for neutrophils, 0.1 mg/mouse; Bio X Cell (Daley et al., 2008) or isotype control (rat $IgG_{2a}$, 2A3; 24 hours prior to s.c. injection of B16 cells, and then every 3 days until the largest tumor reached 200 $mm^3$. Mice were then euthanized, and blood and tumor tissue removed for FACS analysis.

Immunostaining

B16 and J774 cells (at approx. $2.5 \times 10^4 cells/cm^2$) on cover slips or OCT-embedded tumor sections were incubated with primary antibody to mouse C3aR (Bachem, Bubendorf, Switzerland), followed by secondary antibody, anti-chicken Ig-Alexa 488 (Sigma-Aldrich, St Louis, Mo.). Tissue sections were also incubated with directly conjugated antibodies to CD45, Ly-6G, F4/80 and CD3 (all from BioLegend) (Serotec, Kidlington, UK). Nuclei were stained with Hoechst 33342 (Invitrogen) and visualized using an Olympus BX-61 microscope fitted with a Regita EXi cooled CCD camera. Refer to Supplemental Experimental Procedures for more detailed information.

Flow Cytometric Analysis

Single cell suspensions of blood, tumor, spleen and lymph node and bone marrow cell were prepared for surface staining with antibodies to mouse CD45, F4/80, CD11b, Ly6G, Gr-1, CD3, CD4, CD8a (all from Biolegend, San Diego, Calif.). Staining for Tregs was carried out using a FoxP3 Fix/Perm kit (BioLegend), according to manufacturer's instructions. For Th1, Th2, Th17 staining, cells were stimulated with phorbol 12-myristate 13-acetate (PMA; 50 ng/ml; Sigma) and ionomycin (1 µM; Sigma) in the presence of Brefeldin A (5 µg/ml; BioLegend) for 4 h at 37° C. After surface staining, cells were fixed and permeabilized for staining of intracellular cytokines; IL-4, IL-17A or IFN-γ (all from BioLegend). Flow cytometry was performed using an Accuri C6 flow cytometer (BD Biosciences) and data analysis with FlowJo software (Tree Star, Inc., Ashland, Oreg.). Details are provided in Supplemental Experimental Procedures.

Cytokine Assay

Snap frozen tumor tissue was pulverized with a mortar and pestle, then cytoplasmic extracts prepared according to manufacturers' instructions (Milliplex Cell Lysis Kit; Merck Millipore, Darmstadt, Germany). Tissue extracts and plasma from the same animals were stored at −80° C. until assay. Cytokine levels in tumor tissue extracts (0.25 mg protein/well) and plasma (undiluted) were determined by multiplex ELISA (Mouse Cytokine/Chemokine Panel MPMCYTOMAG70K14; Millipore) according to the manufacturer's instructions.

Western Analysis

B16 cells were treated with recombinant human C3a (10 nM) or the selective mouse C3aR agonist WWGKKYRASKLGLAR [SEQ ID NO: 5] (Proctor et al., 2009; Wu et al., 2013) for the times indicated in the experiment. After treatment, crude protein extracts were obtained by disrupting the cells in RIPA lysis buffer. Samples were subjected to SDS-PAGE (Laemmli, 1970), then separated proteins electrotransferred (Towbin et al., 1979) to a PVDF membrane. Membranes were incubated with antibodies to anti-phospho-AKT, anti-total AKT (Cell Signaling, Danvers, Mass.), mouse anti-diphosphorylated ERK1/2 and rabbit anti-total ERK1/2 (Sigma-Aldrich) followed by fluorescently-labelled secondary antibodies (IR Dye 800CW-goat anti-mouse Ig and IR Dye 680LT anti-rabbit Ig; Li-Cor Biosciences). Immunoreactive bands were visualized by scanning on an Odyssey Imaging System (Li-Cor Biosciences) and the percentage phosphorylated protein relative to total protein determined using Odyssey V3.0 image analysis software.

Cell Migration Assay

Cells were seeded at confluence ($2 \times 10^5$ cells/cm²) into a 24 well plate, adhered overnight and then confluent monolayers scratched with a pipette tip before being treated for 24 hours with C3aR agonist ($10^{-6}$ mol/L); control wells were incubated with medium alone or containing 5% FCS. Migration was quantified by measuring cell-free areas at day 0 and 24 hours using Image-J software (NIH, Bethesda, Md., USA).

Effect of C3AR Deficiency on Neutrophil Mobilization by G-CSF

Wild-type, or C3aR$^{-/-}$ mice were injected i.v. with G-CSF (Lenograstim; 120 µg/kg), or vehicle (saline). Blood was collected after 2 hours, and CD11b+Ly6G+ neutrophils analyzed using flow cytometry for CD11b+ and Ly6G+.

Statistical Analysis

Each experiment was performed a minimum of 3 times and statistical analyses were performed using the statistical software package GraphPad Prism® v5.04. Results are expressed as mean±SD. Tumor growth curves were analyzed by Permutation test and survival studies by log-rank Mantel-Cox test. All other data were analyzed by Mann-Whitney test or Kruskal Wallis test followed by Dunn's multiple comparisons test. For all tests, a P value of <0.05 was considered statistically significant.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Ajona, D., Pajares, Corrales, L., Perez-Gracia, J. L., Agorreta, J., Lozano, M. D., Torre, W., Massion, P. P., de-Torres, J. P., Jantus-Lewintre, E., et al. (2013). Investigation of complement activation product c4d as a diagnostic and prognostic biomarker for lung cancer. J Natl Cancer Inst 105, 1385-1393.

Bugl, S., Wirths, S., Radsak, M. P., Schild, H., Stein, P., Andre, M. C., Muller, M. R., Malenke, E., Wiesner, T., Marklin, M., et al. (2013). Steady-state neutrophil homeostasis is dependent on TLR4/TRIF signaling. Blood 121, 723-733.

Chew, V., Chen, J., Lee, D., Loh, E., Lee, J., Lim, K. H., Weber, A., Slankamenac, K., Poon, R. T., Yang, H., et al. (2012). Chemokine-driven lymphocyte infiltration: an early intratumoral event determining long-term survival in resectable hepatocellular carcinoma. Gut 61, 427-438.

Cho, M. S., Vasquez, H. G., Rupaimoole, R., Pradeep, S., Wu, S., Zand, B., Han, H. D., Rodriguez-Aguayo, C., Bottsford-Miller, J., Huang, J., et al. (2014). Autocrine effects of tumor-derived complement. Cell Rep 6, 1085-1095.

Chu, Y., Xia, M., Lin, Y., Li, A., Wang, Y., Liu, R., and Xiang, S. (2006). Th2-dominated antitumor immunity induced by DNA immunization with the genes coding for a basal core peptide PDTRP and GM-CSF. Cancer Gene Ther 13, 510-519.

Corrales, L., Ajona, D., Rafail, S., Lasarte, J. J., Riezu-Boj, Lambris, J. D., Rouzaut, A., Pajares, M. J., Montuenga, L. M., and Pio, R. (2012). Anaphylatoxin C5a creates a favorable microenvironment for lung cancer progression. J Immunol 189, 4674-4683.

Corthay, A., Skovseth, D. K., Lundin, K. U., Rosjo, E., Omholt, H., Hofgaard, P. O., Haraldsen, G., and Bogen, B. (2005). Primary antitumor immune response mediated by CD4+ T cells. Immunity 22, 371-383.

Coulthard, L. G., and Woodruff, T. M. (2015). Is the Complement Activation Product C3a a Proinflammatory Molecule? Re-evaluating the Evidence and the Myth. J Immunol 194, 3542-3548.

Cua, D. J., and Tato, C. M. (2010). Innate IL-17-producing cells: the sentinels of the immune system. Nat Rev Immunol 10, 479-489.

Daley, J. M., Thomay, A. A., Connolly, M. D., Reichner, J. S., and Albina, J. E. (2008). Use of Ly6G-specific monoclonal antibody to deplete neutrophils in mice. J Leukoc Biol 83, 64-70.

Eggermont, A. M., Spatz, A., and Robert, C. (2014). Cutaneous melanoma. Lancet 383, 816-827.

Eruslanov, E. B., Bhojnagarwala, P. S., Quatromoni, J. G., Stephen, T. L., Ranganathan, A., Deshpande, C., Akimova, T., Vachani, A., Litzky, L., Hancock, W. W., et al. (2014). Tumor-associated neutrophils stimulate T cell responses in early-stage human lung cancer. J Clin Invest 124, 5466-5480.

Fridlender, Z. G., Sun, J., Kim, S., Kapoor, V., Cheng, G., Ling, L., Worthen, G. S., and Albelda, S. M. (2009). Polarization of tumor-associated neutrophil phenotype by TGF-beta: "N1" versus "N2" TAN. Cancer Cell 16, 183-194.

Fridlender, Z. G., Sun, J., Mishalian, I., Singhal, S., Cheng, G., Kapoor, V., Horng, W., Fridlender, G., Bayuh, R., Worthen, G. S., and Albelda, S. M. (2012). Transcriptomic analysis comparing tumor-associated neutrophils with granulocytic myeloid-derived suppressor cells and normal neutrophils. PLoS One 7, e31524.

Fridman, W. H., Pages, F., Sautes-Fridman, C., and Galan, J. (2012). The immune contexture in human tumors: impact on clinical outcome. Nat Rev Cancer 12, 298-306.

Galdiero, M. R., Bonavita, E., Barajon, I., Garlanda, C., Mantovani, A., and Jaillon, S. (2013). Tumor associated macrophages and neutrophils in cancer. Immunobiology 218, 1402-1410.

Gnerlich, Mitchem, J. B., Weir, J. S., Sankpal, N. V., Kashiwagi, H., Belt, B. A., Porembka, M. R., Herndon, J. M., Eberlein, T. J., Goedegebuure, P., and Linehan, D. C. (2010). Induction of Th17 cells in the tumor microenvironment improves survival in a murine model of pancreatic cancer. J Immunol 185, 4063-4071.

Garter, A., and Meri, S. (1999). Immune evasion of tumor cells using membrane-bound complement regulatory proteins. Immunol Today 20, 576-582.

Granot, Z., Henke, E., Comen, E. A., King, T. A., Norton, L., and Benezra, R. (2011). Tumor entrained neutrophils inhibit seeding in the premetastatic lung. Cancer Cell 20, 300-314.

Gregory, A. D., and Houghton, A. M. (2011). Tumor-associated neutrophils: new targets for cancer therapy. Cancer Res 71, 2411-2416.

Gunn, L., Ding, C., Liu, M., Ma, Y., Qi, C., Cai, Y., Hu, X., Aggarwal, D., Zhang, H. G., and Yan, J. (2012). Opposing roles for complement component C5a in tumor progression and the tumor microenvironment. J Immunol 189, 2985-2994.

Hemdan, N. Y. (2013). Anti-cancer versus cancer-promoting effects of the interleukin-17-producing T helper cells. Immunol Lett 149, 123-133.

Hong, M., Puaux, A. L., Huang, C., Loumagne, L., Tow, C., Mackay, C., Kato, M., Prevost-Blondel, A., Avril, M. F., Nardin, A., and Abastado, J. P. (2011). Chemotherapy induces intratumoral expression of chemokines in cutaneous melanoma, favoring T-cell infiltration and tumor control. Cancer Res 71, 6997-7009.

Johrer, K., Pleyer, L., Olivier, A., Maizner, E., Zelle-Rieser, C., and Greil, R. (2008). Tumor-immune cell interactions modulated by chemokines. Expert Opin Biol Ther 8, 269-290.

Kim, D. Y., Martin, C. B., Lee, S. N., and Martin, B. K. (2005). Expression of complement protein C5a in a murine mammary cancer model: tumor regression by interference with the cell cycle. Cancer Immunol Immunother 54, 1026-1037.

Kim, H. J., and Cantor, H. (2014). CD4 T-cell subsets and tumor immunity: the helpful and the not-so-helpful. Cancer Immunol Res 2, 91-98.

Klos, A., Tenner, A. J., Johswich, K. O., Ager, R. R., Reis, E. S., and Kohl, J. (2009). The role of the anaphylatoxins in health and disease. Mol Immunol 46, 2753-2766.

Klos, A., Wende, E., Wareham, K. J., and Monk, P. N. (2013). International Union of Pharmacology. LXXXVII. Complement peptide C5a, C4a, and C3a receptors. Pharmacol Rev 65, 500-543.

Knight, D. A., Ngiow, S. F., Li, M., Parmenter, T., Mok, S., Cass, A., Haynes, N. M., Kinross, K., Yagita, H., Koya, R. C., et al. (2013). Host immunity contributes to the antimelanoma activity of BRAF inhibitors. J Clin Invest 123, 1371-1381.

Kottke, T., Sanchez-Perez, L., Diaz, R. M., Thompson, J., Chong, H., Harrington, K., Calderwood, S. K., Pulido, J., Georgopoulos, N., Selby, P., et al. (2007). Induction of hsp70-mediated Th17 autoimmunity can be exploited as immunotherapy for metastatic prostate cancer. Cancer Res 67, 11970-11979.

Kryczek, I., Wei, S., Zou, L., Altuwaijri, S., Szeliga, W., Kolls, J., Chang, A., and Zou, W. (2007). Cutting edge: Th17 and regulatory T cell dynamics and the regulation by IL-2 in the tumor microenvironment. J Immunol 178, 6730-6733.

Laemmli, U.K. (1970). Cleavage of structural proteins during the assembly of the head of bacteriophage T4. Nature 227, 680-685.

Li, L., Huang, L., Vergis, A. L., Ye, H., Bajwa, A., Narayan, V., Strieter, R. M., Rosin, D. L., and Okusa, M. D. (2010). IL-17 produced by neutrophils regulates IFN-gamma-mediated neutrophil migration in mouse kidney ischemia-reperfusion injury. J Clin Invest 120, 331-342.

Lim, H., Kim, Y. U., Drouin, S. M., Mueller-Ortiz, S., Yun, K., Morschl, E., Wetsel, R. A., and Chung, Y. (2012). Negative regulation of pulmonary Th17 responses by C3a anaphylatoxin during allergic inflammation in mice. PLoS One 7, e52666.

Lv, L., Pan, K., Li, X. D., She, K. L., Zhao, J. J., Wang, W., Chen, J. G., Chen, Y. B., Yun, J. P., and Xia, J. C. (2011). The accumulation and prognosis value of tumor infiltrating IL-17 producing cells in esophageal squamous cell carcinoma. PLoS One 6, e18219.

Maher, S. G., McDowell, D. T., Collins, B. C., Muldoon, C., Gallagher, W. M., and Reynolds, J. V. (2011). Serum proteomic profiling reveals that pretreatment complement protein levels are predictive of esophageal cancer patient response to neoadjuvant chemoradiation. Ann Surg 254, 809-816; discussion 816-807.

Markiewski, M. M., DeAngelis, R. A., Benencia, F., Ricklin-Lichtsteiner, S. K., Koutoulaki, A., Gerard, C., Coukos, G., and Lambris, J. D. (2008). Modulation of the antitumor immune response by complement. Nat Immunol 9, 1225-1235.

Martin-Orozco, N., Muranski, P., Chung, Y., Yang, X. O., Yamazaki, T., Lu, S., Hwu, P., Restifo, N. P., Overwijk, W. W., and Dong, C. (2009). T helper 17 cells promote cytotoxic T cell activation in tumor immunity. Immunity 31, 787-798.

Mattes, J., Hulett, M., Xie, W., Hogan, S., Rothenberg, M. E., Foster, P., and Parish, C. (2003). Immunotherapy of cytotoxic T cell-resistant tumors by T helper 2 cells: an eotaxin and STAT6-dependent process. J Exp Med 197, 387-393.

Medina-Echeverz, J., Aranda, F., and Berraondo, P. (2014). Myeloid-derived cells are key targets of tumor immunotherapy. Oncoimmunology 3, e28398.

Medina-Echeverz, J., Fioravanti, J., Zabala, M., Ardaiz, N., Prieto, J., and Berraondo, P. (2011). Successful colon cancer eradication after chemoimmunotherapy is associated with profound phenotypic change of intratumoral myeloid cells. J Immunol 186, 807-815.

Mishalian, I., Bayuh, R., Levy, L., Zolotarov, L., Michaeli, J., and Fridlender, Z. G. (2013). Tumor-associated neutrophils (TAN) develop pro-tumorigenic properties during tumor progression. Cancer Immunol Immunother 62, 1745-1756.

Moran, C. J., Arenberg, D. A., Huang, C. C., Giordano, T. J., Thomas, D. G., Misek, D. E., Chen, G., Iannettoni, M. D., Orringer, M. B., Hanash, S., and Beer, D. G. (2002). RANTES expression is a predictor of survival in stage I lung adenocarcinoma. Clin Cancer Res 8, 3803-3812.

Mule, J. J., Custer, M., Averbook, B., Yang, J. C., Weber, J. S., Goeddel, D. V., Rosenberg, S. A., and Schall, T. J. (1996). RANTES secretion by gene-modified tumor cells results in loss of tumorigenicity in vivo: role of immune cell subpopulations. Hum Gene Ther 7, 1545-1553.

Muranski, P., Boni, A., Antony, P. A., Cassard, L., Irvine, K. R., Kaiser, A., Paulos, C. M., Palmer, D. C., Touloukian, C. E., Ptak, K., et al. (2008). Tumor-specific Th17-polarized cells eradicate large established melanoma. Blood 112, 362-373.

Musiani, P., Allione, A., Modica, A., Lollini, P. L., Giovarelli, M., Cavallo, F., Belardelli, F., Forni, G., and Modesti, A. (1996). Role of neutrophils and lymphocytes in inhibition of a mouse mammary adenocarcinoma engineered to release IL-2, IL-4, IL-7, IL-10, IFN-alpha, IFN-gamma, and TNF-alpha. Lab Invest 74, 146-157.

Niculescu, F., Rus, H. G., Retegan, M., and Vlaicu, R. (1992). Persistent complement activation on tumor cells in breast cancer. Am J Pathol 140, 1039-1043.

Niwa, Y., Akamatsu, H., Niwa, H., Sumi, H., Ozaki, Y., and Abe, A. (2001). Correlation of tissue and plasma RANTES levels with disease course in patients with breast or cervical cancer. Clin Cancer Res 7, 285-289.

Nunez-Cruz, S., Gimotty, P. A., Guerra, M. W., Connolly, D. C., Wu, Y. Q., DeAngelis, R. A., Lambris, J. D., Coukos, G., and Schaller, N. (2012). Genetic and pharmacologic inhibition of complement impairs endothelial cell function and ablates ovarian cancer neovascularization. Neoplasia 14, 994-1004.

Pelletier, M., Maggi, L., Micheletti, A., Lazzeri, E., Tamassia, N., Costantini, C., Cosmi, L., Lunardi, C., Annunziato, F., Romagnani, S., and Cassatella, M. A. (2010). Evidence for a cross-talk between human neutrophils and Th17 cells. Blood 115, 335-343.

Pericle, F., Giovarelli, M., Colombo, M. P., Ferrari, G., Musiani, P., Modesti, A., Cavallo, F., Di Pierro, F., Novelli, F., and Forni, G. (1994). An efficient Th2-type memory follows CD8+ lymphocyte-driven and eosinophil-mediated rejection of a spontaneous mouse mammary adenocarcinoma engineered to release IL-4. J Immunol 153, 5659-5673.

Proctor, L. M., Moore, T. A., Monk, P. N., Sanderson, S. D., Taylor, S. M., and Woodruff, T. M. (2009). Complement factors C3a and C5a have distinct hemodynamic effects in the rat. Int Immunopharmacol 9, 800-806.

Ricklin, D., Hajishengallis, G., Yang, K., and Lambris, J. D. (2010). Complement: a key system for immune surveillance and homeostasis. Nat Immunol 11, 785-797.

Rosenberg, S. A., Spiess, P., and Lafreniere, R. (1986). A new approach to the adoptive immunotherapy of cancer with tumor-infiltrating lymphocytes. Science 233, 1318-1321.

Souto, J. C., Vila, L., and Bru, A. (2011). Polymorphonuclear neutrophils and cancer: intense and sustained neutrophilia as a treatment against solid tumors. Med Res Rev 31, 311-363.

Su, X., Ye, J., Hsueh, E. C., Zhang, Y., Hoft, D. F., and Peng, G. (2010). Tumor microenvironments direct the recruitment and expansion of human Th17 cells. J Immunol 184, 1630-1641.

Towbin, H., Staehelin, T., and Gordon, J. (1979). Electrophoretic transfer of proteins from polyacrylamide gels to nitrocellulose sheets: procedure and some applications. Proc Natl Acad Sci USA 76, 4350-4354.

Woodruff, T. M., Tenner, A. (2015). A Commentary on: NF-KB-Activated Astroglial Release of Complement C3 Compromises Neuronal Morphology and Function Associated with Alzheimer's Disease. A Cautionary Note Regarding C3aR. Front. Immunol.

Wu, M. C., Brennan, F. H., Lynch, J. P., Mantovani, S., Phipps, S., Wetsel, R. A., Ruitenberg, Taylor, S. M., and Woodruff, T. M. (2013). The receptor for complement component C3a mediates protection from intestinal ischemia-reperfusion injuries by inhibiting neutrophil mobilization. Proc Natl Acad Sci USA 110, 9439-9444.

Xu, L., Shen, S. S., Hoshida, Y., Subramanian, A., Ross, K., Brunet, J. P., Wagner, S. N., Ramaswamy, S., Mesirov, J. P., and Hynes, R. O. (2008). Gene expression changes in an animal melanoma model correlate with aggressiveness of human melanoma metastases. Mol Cancer Res 6, 760-769.

Ye, J., Livergood, R. S., and Peng, G. (2013). The role and regulation of human Th17 cells in tumor immunity. Am J Pathol 182, 10-20.

Zhang, S., Bernard, D., Khan, W. I., Kaplan, M. H., Bramson, J. L., and Wan, Y. (2009). CD4+ T-cell-mediated anti-tumor immunity can be uncoupled from autoimmunity via the STAT4/STAT6 signaling axis. Eur J Immunol 39, 1252-1259.

What is claimed is:

1. A method for treating a cancer in a subject, the method comprising: concurrently administering to the subject (1) a C3aR antagonist and (2) a mobilizer of hematopoietic stem cells and/or progenitor cells in effective amounts to treat the cancer.

2. The method according to claim 1, wherein the cancer is a metastatic cancer.

3. The method according to claim 1, further comprising administering to the subject (3) an ancillary therapy or agent that inhibits proliferation, survival, or viability of the tumor.

4. The method according to claim 3, wherein the ancillary therapy or agent is selected from the group consisting of radiotherapy, surgery, chemotherapy, hormone ablation therapy, pro-apoptosis therapy, and immunotherapy.

5. The method according to claim 3, wherein the ancillary therapy or agent targets rapidly dividing cells or disrupts the cell cycle or cell division.

6. The method according to claim 1, further comprising administering an E-selectin antagonist for delaying hematopoietic stem cell turnover and/or for protecting hematopoietic stem cells and/or progenitor cells from medical treatments that target rapidly dividing cells and/or for enhancing mobilization of hematopoietic stem cells and/or progenitor cells by the mobilizer.

7. The method according to claim 3, further comprising administering a medicament that treats, prevents, or otherwise ameliorates an immunocompromised condition resulting from the ancillary therapy or agent.

8. The method according to claim 1, wherein the mobilizer of hematopoietic stem cells and/or progenitor cells is selected from among granulocyte colony stimulating factor (G-CSF), granulocyte-macrophage colony stimulating factor (GM-CSF), macrophage colony stimulating factor (M-CSF), stem cell factor, FLT-3 ligand, erythropoietin, interleukin-1 (IL-1), interleukin-3 (IL-3), interleukin-6 (IL-6), interleukin-11 (IL-11), interleukin-7 (IL-7), interleukin-7 (IL-8), interleukin-12 (IL12), MMP2, MMP9, cathepsin G, elastase, cathepsin K, dipeptidyl peptidase-1 (DDP-1), MIP-1α and Gro-β, vascular endothelial growth factor (VEGF), plerixafor, AMD-070, BKT140, KRH-2731/CS-3955, AVR 118, POL5551, and CTCE-0214.

* * * * *

SEQUENCE LISTING

<160> NUMBER OF SEQ ID NOS: 5

<210> SEQ ID NO 1
<211> LENGTH: 257
<212> TYPE: PRT
<213> ORGANISM: Homo sapiens

<400> SEQUENCE: 1

```
Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Asn Tyr
            20                  25                  30

Gly Ile Thr Trp Val Arg Gln Ala Pro Gly Gln Gly Leu Glu Trp Met
            35                  40                  45

Gly Trp Ile Ser Gly Tyr Asn Gly Asp Thr Asn Tyr Ala Gln Lys Leu
50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Ile Tyr Tyr Cys
                85                  90                  95

Thr Arg Asp Leu Pro Gly Leu Asn Trp Ala Tyr Ser Tyr Asp Tyr Met
            100                 105                 110

Asp Val Trp Gly Arg Gly Thr Leu Val Thr Val Ser Ser Gly Gly Gly
            115                 120                 125

Gly Ser Gly Gly Gly Gly Ser Gly Gly Gly Gly Ser Ala Gln Ala Val
        130                 135                 140

Leu Thr Gln Pro Ser Ser Leu Ser Ala Ser Pro Gly Thr Ser Ala Ser
145                 150                 155                 160

Leu Thr Cys Thr Leu Arg Ser Gly Ile Asn Val Gly Thr Tyr Arg Ile
            165                 170                 175

Tyr Trp Tyr Gln Gln Lys Pro Gly Ser Pro Pro His Phe Leu Leu Arg
            180                 185                 190

Tyr Lys Ser Asp Ser Asp Lys Gln Gln Gly Ser Gly Val Pro Ser Arg
            195                 200                 205

Phe Ser Gly Ser Lys Asp Ala Ser Ala Asn Ala Gly Ile Leu Leu Ile
            210                 215                 220

Ser Gly Leu Gln Ser Asp Asp Glu Ala Asp Tyr Tyr Cys Met Ile Trp
225                 230                 235                 240

His Ser Ser Ala Trp Val Phe Gly Gly Gly Thr Lys Val Thr Val Leu
                245                 250                 255

Gly

<210> SEQ ID NO 2
<211> LENGTH: 247
<212> TYPE: PRT
<213> ORGANISM: Homo sapiens

<400> SEQUENCE: 2

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Ser Ser Tyr Thr Asn Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Asp Tyr Asp Ser Tyr Asp Ala Phe Asp Ile Trp Gly
            100                 105                 110
```

```
Lys Gly Thr Leu Val Thr Val Ser Leu Gly Gly Gly Ser Gly Gly
        115                 120                 125

Gly Gly Ser Gly Gly Gly Ser Gln Ser Val Leu Thr Gln Pro Pro
        130                 135                 140

Ser Val Ser Ala Ala Pro Gly Gln Lys Val Thr Ile Ser Cys Ser Gly
145                 150                 155                 160

Ser Thr Ser Asn Ile Gly Asn Asn Tyr Val Ser Trp Tyr Gln Gln His
                165                 170                 175

Pro Gly Lys Ala Pro Lys Leu Met Ile Tyr Asp Val Ser Lys Arg Pro
                180                 185                 190

Ser Gly Val Pro Asp Arg Phe Ser Gly Ser Lys Ser Gly Asn Ser Val
                195                 200                 205

Ser Leu Asp Ile Ser Gly Leu Gln Ser Glu Asp Glu Ala Asp Tyr Tyr
        210                 215                 220

Cys Ala Ala Trp Asp Asp Ser Leu Ser Glu Phe Leu Phe Gly Thr Gly
225                 230                 235                 240

Thr Lys Leu Thr Val Leu Gly
                245
```

```
<210> SEQ ID NO 3
<211> LENGTH: 93
<212> TYPE: PRT
<213> ORGANISM: Artificial Sequence
<220> FEATURE:
<223> OTHER INFORMATION: CXCL12

<400> SEQUENCE: 3
```

```
Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90
```

```
<210> SEQ ID NO 4
<211> LENGTH: 360
<212> TYPE: PRT
<213> ORGANISM: Artificial Sequence
<220> FEATURE:
<223> OTHER INFORMATION: CXCR4

<400> SEQUENCE: 4
```

```
Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
                20                  25                  30

Lys Glu Pro Cys Phe Arg Glu Glu Asn Ala Asn Phe Asn Lys Ile Phe
            35                  40                  45

Leu Pro Thr Ile Tyr Ser Ile Ile Phe Leu Thr Gly Ile Val Gly Asn
        50                  55                  60

Gly Leu Val Ile Leu Val Met Gly Tyr Gln Lys Lys Leu Arg Ser Met
```

```
                65                  70                  75                  80
Thr Asp Lys Tyr Arg Leu His Leu Ser Val Ala Asp Leu Leu Phe Val
                    85                  90                  95

Ile Thr Leu Pro Phe Trp Ala Val Asp Ala Val Ala Asn Trp Tyr Phe
                    100                 105                 110

Gly Asn Phe Leu Cys Lys Ala Val His Val Ile Tyr Thr Val Asn Leu
                    115                 120                 125

Tyr Ser Ser Val Leu Ile Leu Ala Phe Ile Ser Leu Asp Arg Tyr Leu
                    130                 135                 140

Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                    165                 170                 175

Ile Pro Asp Phe Ile Phe Ala Asn Val Ser Glu Ala Asp Asp Arg Tyr
                    180                 185                 190

Ile Cys Asp Arg Phe Tyr Pro Asn Asp Leu Trp Val Val Val Phe Gln
                    195                 200                 205

Phe Gln His Ile Met Val Gly Leu Ile Leu Pro Gly Ile Val Ile Leu
                    210                 215                 220

Ser Cys Tyr Cys Ile Ile Ile Ser Lys Leu Ser His Ser Lys Gly His
225                 230                 235                 240

Gln Lys Arg Lys Ala Leu Lys Thr Thr Val Ile Leu Ile Leu Ala Phe
                    245                 250                 255

Phe Ala Cys Trp Leu Pro Tyr Tyr Ile Gly Ile Ser Ile Asp Ser Phe
                    260                 265                 270

Ile Leu Leu Glu Ile Ile Lys Gln Gly Cys Glu Phe Glu Asn Thr Val
                    275                 280                 285

His Lys Trp Ile Ser Ile Thr Glu Ala Leu Ala Phe Phe His Cys Cys
                    290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                    325                 330                 335

Leu Ser Lys Gly Lys Arg Gly Gly His Ser Ser Val Ser Thr Glu Ser
                    340                 345                 350

Glu Ser Ser Ser Phe His Ser Ser
                    355                 360

<210> SEQ ID NO 5
<211> LENGTH: 15
<212> TYPE: PRT
<213> ORGANISM: Homo sapiens

<400> SEQUENCE: 5

Trp Trp Gly Lys Lys Tyr Arg Ala Ser Lys Leu Gly Leu Ala Arg
```